(12) United States Patent
Wolff et al.

(10) Patent No.: US 12,264,369 B2
(45) Date of Patent: *Apr. 1, 2025

(54) REAL-TIME PCR FOR THE DETECTION OF PATHOGENS

(71) Applicant: The Government of the USA as represented by the Secretary of the Dept. of Health and Human Services, Atlanta, GA (US)

(72) Inventors: Bernard J. Wolff, Roswell, GA (US); Jonas M. Winchell, Lilburn, GA (US); Maureen Diaz, Atlanta, GA (US)

(73) Assignee: The Government of the United States of America as represented by the Secretary of the Deptartment of Health and Human Services, Bethesda, MD (US)

( * ) Notice: Subject to any disclaimer, the term of this patent is extended or adjusted under 35 U.S.C. 154(b) by 506 days.

This patent is subject to a terminal disclaimer.

(21) Appl. No.: 17/485,953

(22) Filed: Sep. 27, 2021

(65) Prior Publication Data

US 2022/0010365 A1 Jan. 13, 2022

Related U.S. Application Data

(62) Division of application No. 16/056,147, filed on Aug. 6, 2018, now Pat. No. 11,162,144, which is a division of application No. 14/398,390, filed as application No. PCT/US2013/028034 on Feb. 27, 2013, now Pat. No. 10,072,305.

(60) Provisional application No. 61/642,091, filed on May 3, 2012.

(51) Int. Cl.
*C12Q 1/689* (2018.01)
*C12Q 1/6895* (2018.01)

(52) U.S. Cl.
CPC ............ *C12Q 1/689* (2013.01); *C12Q 1/6895* (2013.01); *C12Q 2600/158* (2013.01); *C12Q 2600/16* (2013.01)

(58) Field of Classification Search
CPC .................................................... C12Q 1/689
See application file for complete search history.

(56) References Cited

U.S. PATENT DOCUMENTS

| 6,531,583 | B1* | 3/2003 | Cassell | .............. | C12Q 1/689 |
| | | | | | 435/7.1 |
| 6,610,836 | B1* | 8/2003 | Breton | .............. | C07K 14/26 |
| | | | | | 435/6.15 |
| 10,072,305 | B2 | 9/2018 | Wolff et al. | | |
| 11,162,144 | B2* | 11/2021 | Wolff | .............. | C12Q 1/689 |
| 2002/0019007 | A1 | 2/2002 | Jensen | | |
| 2004/0043409 | A1 | 3/2004 | Kovacs et al. | | |
| 2014/0336082 | A1* | 11/2014 | Park | .............. | C12Q 1/6883 |
| | | | | | 506/16 |

FOREIGN PATENT DOCUMENTS

| CN | 101748192 | 6/2010 |
| WO | WO 98/23738 | 6/1998 |
| WO | WO 1999/047706 | 9/1999 |
| WO | WO 2011/133433 | 10/2011 |

OTHER PUBLICATIONS

Ahern, "Biochemical, Reagents Kits Offer Scientists Good Return on Investment," *The Scientist*, vol. 9, No. 15, pp. 20, 1995.
Al-Marzooq et al., "Development of multiplex real-time PCR for the rapid detection of five bacterial causes of community acquired pneumonia," *Tropical Biomedicine*, vol. 28, No. 3, pp. 545-556, 2011.
Alvarez-Martinez et al. "Sensitivity and specificity of nested and real-time PCR for the detection of *Pneumocystis jirovecii* in clinical specimens," *Diagnostic Microbiology and Infectious Disease*, vol. 56, pp. 153-160, 2006.
Anbazhagan et al., "Multiplex polymerase chain reaction (PCR) assays for the detection of *Enterobacteriaceae* in clinical samples," *African Journal of Microbiology Research*, vol. 4, No. 11, pp. 1186-1191, 2010.
Babrowski et al., "Pseudomonas aeruginosa virulence expression is directly activated by morphine and is capable of causing lethal gut derived sepsis in mice during chronic morphine administration," *Annals of Surgery*, vol. 255, No. 2, pp. 386-393, 2012 (NIH Public Access Author Manuscript, 17 pages).
Bai et al., "*Bartonella vinsonii* susp. *Arupensis* in Humans, Thailand," *Emerging Inf. Dis.* 18:989-991, 2012.
Chuang et al., "High and Increasing Oxa-51 DNA Load Predict Mortality in *Acinetobacter baumannii* Bacteremia: Implication for Pathogenesis and Evaluation of Therapy," *PLoS ONE* 5(11):e14133, 2010 (10 pages).
Deschaght et al., "Comparison of the sensitivity of culture, PCR and quantitative real-time PCR for the detection of Pseudomonas aeruginosa in sputum of cystic fibrosis patients," *BMC Microbiology*, 9:244, 2009 (7 pages).

(Continued)

*Primary Examiner* — Diana B Johannsen
(74) *Attorney, Agent, or Firm* — Klarquist Sparkman, LLP

(57) ABSTRACT

Methods for detecting presence of one or more of *Acinetobacter baumannii, Pseudomonas aeruginosa, Klebsiella pneumooniae, Toxoplasma gondii, Moraxella catarrhalis, Escherichia coli, Shigella, Staphylococcus aureus, Pneumocystis jirovecii, Chlamydia trachomatis, Ureaplasma urealyticum, Ureaplasma parvum, Ureaplasma* spp., *Bartonella* spp., *Streptococcus agalactiae*, and *Neisseria meningitidis* nucleic acids in a sample, such as a biological sample obtained from a subject, or an environmental sample, are provided. This disclosure also provides probes, primers, and kits for detecting one or more of *Acinetobacter baumannii, Pseudomonas aeruginosa, Klebsiella pneumoniae, Toxoplasma gondii, Moraxella catarrhalis, Escherichia coli, Shigella, Staphylococcus aureus, Pneumocystis jirovecii, Chlamydia trachomatis, Ureaplasma urealyticum, Ureaplasma parvum, Ureaplasma* spp., *Bartonella* spp., *Streptococcus agalactiae*, and *Neisseria meningitidis* in a sample.

23 Claims, 3 Drawing Sheets

Specification includes a Sequence Listing.

(56) References Cited

OTHER PUBLICATIONS iaz et al., "Development of a Novel Genus-Specific Real-Time PCR Assay for Detection and Differentiation of *Bartonella* Species and Genotypes," *Journal of Clinical Microbiology*, vol. 50, No. 5, pp. 1645-1649, 2012.

Dini et al., "High Prevalence of Dihydropteroate Synthase Mutations in *Pneumocystis jirovecii* Isolated from Patients with *Pneumocystis* Pneumonia in South Africa," *Journal of Clinical Microbiology*, vol. 48, No. 6, pp. 2016-2021, 2010.

Elizaquivel et al., "A multiplex RTi-PCR reaction for simultaneous detection of *Escherichia coli* 0157:H7, *Salmonella* spp. and *Staphylococcus aureus* on fresh, minimally processed vegetables," Food Microbiology, vol. 25, No. 5, pp. 705-713, 2008.

Galluzzi et al., "Current molecular techniques for the detection of microbial pathogens," *Science Progress*, vol. 90, No. 1, pp. 29-50, 2007.

Genbank Accession No. AF139132.1, Dec. 1, 1999, (3 pages).

Kodani et al., "Application of TaqMan Low-Density Arrays for Simultaneous Detection of Multiple Respiratory Pathogens," Journal of Clinical Microbiology, vol. 49, No. 6, pp. 2175-2185, 2011.

Kodani et al., Engineered Combined-Positive-Control Template for Real-Time Reverse Transcription-PCR in Multiple-Pathogen-Detection Assays, *Journal of Clinical Microbiology* vol. 50, No. 3, pp. 1057-1060, 2012.

Kong et al., "Species Identification of Ureaplasma parvum and *Ureaplasma urealyticum* Using PCR-Based Assays," *Journal of Clinical Microbiology*, vol. 38, No. 3, pp. 1175-1179, 2000.

Lee et al., "Development and application of an oligonucleotide microarray and real-time quantitative PCR for detection of wastewater bacterial pathogens," *Science of the Total Environment*, vol. 398, pp. 203-211, 2008.

Lehmann et al., "A multiplex real-time PCR assay for rapid detection and differentiation of 25 bacterial and fungal pathogens from whole blood samples," *Medical Microbiology and Immunology*, vol. 197, No. 3, pp. 313-324, 2008.

Mitsuhashi, "Technical Report: Part 2. Basic Requirements for Designing Optimal PCR Primers," *Journal of Clinical Laboratory Analysis*, vol. 10, pp. 285-293, 1996.

Ndam et al., "Development of a Real-Time PCR-Based Fluorescence Assay for Rapid Detection of Point Mutations in *Pneumocystis jirovecii* Dihydropteroate Synthase Gene," *J. Eukaryot. Microbiol.*, vol. 50, pp. 658-660, 2003.

Qin et al., "Use of Real-Time PCR with Multiple Targets to Identify *Pseudomonas aeruginosa* and Other Nonfermenting Gram-Negative Bacilli from Patients with Cystic Fibrosis," *Journal of Clinical Microbiology6*, vol. 41, No. 9, pp. 4312-4317, 2003.

Shapiro et al., "Detection of *Toxoplasma gondii* oocysts and surrogate microspheres in water using ultrafiltration and capsule filtration," *Water Research*, vol. 44, pp. 893-903, 2010.

Sigma Life Science, "qPCR Technical Guide," Sigma-Aldrich Co., 2008 (42 pages).

Thomas et al., "sodC-Based Real-Time PCR for Detection of *Neisseria meningitidis*," *PLoS ONE* 6(5): e19361, 2011 (8 pages).

Volkmann et al., "Evaluation of inhibition and cross-reaction effects on real-time PCR applied to the total DNA of wastewater samples for the quantification of bacterial antibiotic resistance genes and taxon-specific targets," *Molecular and Cellular Probes*, vol. 21, No. 2, pp. 125-133, 2007.

Xiao et al., "Detection and Characterization of Human *Ureaplasma* Species and Serovars by Real-Time PCR," *Journal of Clinical Microbiology*, Vo. 48, No. 8, pp. 2715-2723, 2010.

* cited by examiner

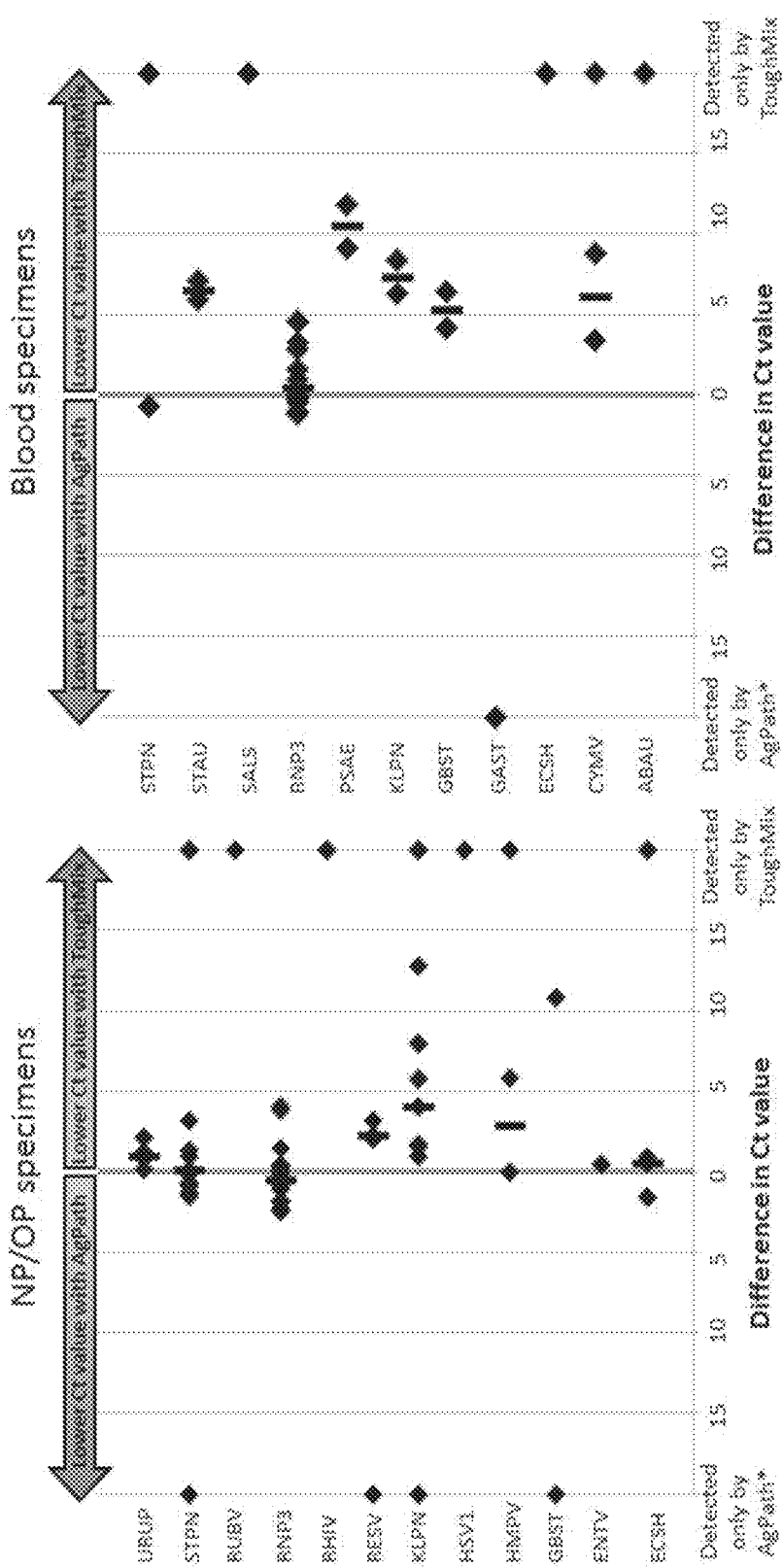

SEQUENCE LISTING

```
<160> NUMBER OF SEQ ID NOS: 67

<210> SEQ ID NO 1
<211> LENGTH: 825
<212> TYPE: DNA
<213> ORGANISM: Acinetobacter baumannii

<400> SEQUENCE: 1
atgaacatta aaacactctt acttataaca agcgctattt ttatttcagc ctgctcacct      60
tatatagtga ctgctaatcc aaatcacagc gcttcaaaat ctgatgaaaa agcagagaaa     120
attaaaaatt tatttaacga agtacacact acgggtgttt tagttatcca acaaggccaa     180
actcaacaaa gctatggtaa tgatcttgct cgtgcttcga ccgagtatgt acctgcttcg     240
accttcaaaa tgcttaatgc tttgatcggc cttgagcacc ataaggcaac caccacagaa     300
gtatttaagt gggacgggca aaaaaggcta ttcccagaat gggaaaagga catgacccta     360
ggcgatgcta tgaaagcttc cgctattccg gtttatcaag atttagctcg tcgtattgga     420
cttgaactca tgtctaagga agtgaagcgt gttggttatg gcaatgcaga tatcggtacc     480
caagtcgata atttttggct ggtgggtcct ttaaaaatta ctcctcagca agaggcacag     540
tttgcttaca agctagctaa taaaacgctt ccatttagcc caaaagtcca agatgaagtg     600
```

| | |
|---|---|
| caatccatgt tattcataga agaaaagaat ggaaataaaa tatacgcaaa aagtggttgg | 660 |
| ggatgggatg tagacccaca agtaggctgg ttaactggat gggttgttca gcctcaagga | 720 |
| aatattgtag cgttctccct taacttagaa atgaaaaaag gaatacctag ctctgttcga | 780 |
| aaagagatta cttataaaag tttagaacaa ttaggtattt tatag | 825 |

```
<210> SEQ ID NO 2
<211> LENGTH: 420
<212> TYPE: DNA
<213> ORGANISM: Chlamydia trachomatis

<400> SEQUENCE: 2
```

| | |
|---|---|
| ctatggaggt ggagagagtc gaactctcgt ccttagtaaa ctccccgcta acctctacat | 60 |
| gcttagttcc taggtactat acgttatgtc tcctcagcta gaaaccccta tagagactaa | 120 |
| cgactctcat taaatttcaa actcatttcc tcgagaatta aaggacctaa gttctaacca | 180 |
| gatacatgac ggtgtttcga aaacctctgg tggagctcgc gaacaccggg tcacccgtat | 240 |
| ttaggtaaca actttgctaa ttaagcagct actcttagat cttcgagatc agcgaagctg | 300 |
| ataatttcgc attcagcctt aggttcggca tttattgttt tgtcggcttt ttaggaggcc | 360 |
| agccaacgcc ctccgcatgc aattaacgct tcatttctaa gtcgaaacct ttacaccccc | 420 |

```
<210> SEQ ID NO 3
<211> LENGTH: 1812
<212> TYPE: DNA
<213> ORGANISM: Escherichia coli

<400> SEQUENCE: 3
```

| | |
|---|---|
| tcattgtttg cctccctgct gcggttttc accgaagttc atgccagtcc agcgtttttg | 60 |
| cagcagaaaa gccgccgact tcggtttgcg gtcgcgagtg aagatccctt tcttgttacc | 120 |
| gccaacgcgc aatatgcctt gcgaggtcgc aaaatcggcg aaattccata cctgttcacc | 180 |
| gacgacggcg ctgacgcgat caaagacgcg gtgatacata tccagccatg cacactgata | 240 |
| ctcttcactc cacatgtcgg tgtacattga gtgcagcccg gctaacgtat ccacgccgta | 300 |
| ttcggtgatg ataatcggct gatgcagttt ctcctgccag gccagaagtt ctttttccag | 360 |
| taccttctct gccgtttcca aatcgccgct ttggacatac catccgtaat aacggttcag | 420 |
| gcacagcaca tcaaagagat cgctgatggt atcggtgtga cgtcgcaga acattacatt | 480 |
| gacgcaggtg atcggacgcg tcgggtcgag tttacgcgtt gcttccgcca gtggcgcgaa | 540 |
| atattcccgt gcaccttgcg gacgggtatc cggttcgttg gcaatactcc acatcaccac | 600 |
| gcttgggtgg ttttttgtcac gcgctatcag ctctttaatc gcctgtaagt gcgcttgctg | 660 |
| agtttccccg ttgactgcct cttcgctgta cagttctttc ggcttgttgc ccgcttcgaa | 720 |
| accaatgcct aaagagaggt taaagccgac agcagcagtt tcatcaatca ccacgatgcc | 780 |
| atgttcatct gcccagtcga gcatctcttc agcgtaaggg taatgcgagg tacggtagga | 840 |
| gttggcccca atccagtcca ttaatgcgtg gtcgtgcacc atcagcacgt tatcgaatcc | 900 |
| tttgccacgc aagtccgcat cttcatgacg accaaagcca gtaaagtaga acggtttgtg | 960 |
| gttaatcagg aactgttcgc ccttcactgc cactgaccgg atgccgacgc gaagcgggta | 1020 |
| gatatcacac tctgtctggc ttttggctgt gacgcacagt tcatagagat aaccttcacc | 1080 |
| cggttgccag aggtgcggat tcaccacttg caaagtcccg ctagtgcctt gtccagttgc | 1140 |
| aaccacctgt tgatccgcat cacgcagttc aacgctgaca tcaccattgg ccaccacctg | 1200 |
| ccagtcaaca gacgcgtggt tacagtcttg cgcgacatgc gtcaccacgg tgatatcgtc | 1260 |

```
cacccaggtg ttcggcgtgg tgtagagcat tacgctgcga tggatcccgg catagttaaa      1320
gaaatcatgg aagtaagact gcttttcctt gccgttttcg tcggtaatca ccattcccgg      1380
cgggatagtc tgccagttca gttcgttgtt cacacaaacg gtgatacgta cacttttccc      1440
ggcaataaca tacggcgtga catcggcttc aaatggcgta tagccgccct gatgctccat      1500
cacttcctga ttattgaccc acactttgcc gtaatgagtg accgcatcga acgcagcac       1560 gatacgctgg cctgcccaac ctttcggtat aaagacttcg cgctgatacc agacgttgcc      1620
cgcataatta cgaatatctg catcggcgaa ctgatcgtta aaactgcctg cacagcaat       1680 tgcccggctt tcttgtaacg cgcttttccca ccaacgctga tcaattccac agttttcgcg    1740
atccagactg aatgcccaca ggccgtcgag ttttttgatt tcacggggttg gggtttctac    1800 aggacgtaac at                                                         1812

<210> SEQ ID NO 4
<211> LENGTH: 1575
<212> TYPE: DNA
<213> ORGANISM: Klebsiella pneumoniae

<400> SEQUENCE: 4
ctacagacgc ggcagggtga tatccatgat ctggatccgg taagcgacct ggcgcggcgt       60 catcccagc agccgtgccg ccttggcctg cacccagccg gctttttcca gcgcggcgat       120
cagtcgctga cgttcgtcca ggctgttgtc cagccagctg tcttccgctg gcccgctggc      180
aggcagggct ttggcgggac gatcctggtg agtgaagagg atcacgtcgc gatcgatcag      240
gccactctcc gacatcaccg ccgagcgttc gaggcagttc tccagttcgc gaacgttacc      300
cggccagctg tactccatca gcaggcggat cgcgccctcg ctgatccgca gcgtgcgccc      360
ctgatgctgg ccgattttgc gcaccaggaa gtgcgccagc tcggcgatgt cctcctgacg      420
ctcgcgcagc gggggcaggg cgatgggcat cacgttcaga cgataataga gatcctcgcg      480
gaaatggccc agccggacct cctcctccag gtgacggttg gtggcggcga tgatgcggac      540
attcacccgc agggtctcat cgccgccgac ccgctccatc tcccctcct ggaggatacg       600 cagcagcttg gcctggaacg aggcgctgct ttcaccaatc tcatcgagga acagggtgcc      660
gccatccgcc agctcaaaac gtcctttacg ctgacgcacc gccccggtaa aggcgccttt      720
ctcatggccg aacagttcgc tttccagcag ggtgtccggc agcgccgcgc agttaaattt      780
gacgaaggcg cgccagccc gtggcgaatg gtgatggatg cgttggcga ttagctcttt        840 cccggtgccg ctttcgccgc gtaccagcac ggtggtgtcc cagcgcgaga cctgacggat      900
cacctccacg atctggcgca tcgccgggct cttgccgacc atattgtcaa ggcccacgcc      960
gcgcgacgac gagcaggccg gcggccgttc caccttcggc ggctggcggc tcgacagggc     1020
gggtgaggcc ggaaggatca tcagccggat ggtctgggcg acgaggttgg cgacggtttc     1080
gagaaaacgg gtgcaggccg gcagccgctc ttcctggcgc gccatcggct gggctgccag     1140 caccccctatt ggccgggcgt taggcccat caacggtacg gcgataaacg gcagatcgta     1200
atcgtagagg ctcaggcggt cgagaaaacg ctgatcgtcg gcgacccggg gcagcaccag    1260
cgactgcccc tgggccagca cggtccccac cagtccctcg ccggggcgat gcggatctg     1320 cgtgctgccg gggagggggct gctggccggt ttgctgcagc gcttcgatac tgaggatctc    1380
ctgctcgctg tcgtacaggc agatcatccc gtgctgcata aaggcatcgt tgtgcaatac    1440
gctgagcacc tcctgcaacg ttttgctggc ctcggtggcc cggctcagca ccacgcttat    1500
```

```
ccgctgcatg gcggtgaact gctgagagag gtcgaagcgt ctgacggtgg tgtccgggtc    1560
ggattcaggg atcat                                                     1575

<210> SEQ ID NO 5
<211> LENGTH: 1599
<212> TYPE: DNA
<213> ORGANISM: Moraxella catarrhalis

<400> SEQUENCE: 5
tcaatggcgg aaatgacgca tacctgtaaa gaccatggcg ataccatgct cattagcagc      60
ggcaatcacc tctgcatcac gcattgagcc acctggctga atgatgcatt tgatgccagc     120
agcagcggca ttatcaatac catcacggaa ggggaagaat gcatcagagg ccatcactgc     180
accctcaaca caagccctg catgttctgc tttaattgca gcaatgcgtg ctgaattaac      240
acggctcatt tgacctgcac ccacgccaat ggtttgatga ttttttggcat aaacaatggc    300 attggatttg acatatttgg caactttcca agcaaagagc aaatcatcaa gctcggcatc     360
tgatggcaca cgctcggtga caacttttag gtctgattta tcaatcatgc ccaaatcttg     420
attttggaca gtagaccgc cattgactcg ttttaggtca aattgagctg cccgctgtgt      480
cggctgtggc aactcaccac ataccaagat gcgtacattt tttttactgc ttgtaatttc     540
tagaacacct tcagcgatgc ttggtgcgat gatgacttca acaaattgac gctcaacgat     600
ggtacgggcg gtatcactgt ctaattctcg gttaaaggca ataatgccac caaaggcaga     660
ttcagggtcg gttgcatacg ctaaatgata agcatctaaa ataccgtttt ctgatgttgc     720
aacaccacaa ggattggcat gtttgacaat cacacaagca ggcgtggtaa agatttgac     780 acactcaagt gccgcatcgg tatcagcaat attattataa gacaacgctt taccttgtaa     840
ttgctgtgca gtcgcaacag acgcttctgt tgcatgatca tctacataaa aggctgctga     900
ctgatgtggg tttttcgccat atctaagctc ttgtgctttg gtgaattggt gattaaaagt    960
gcgtgaaaat tgagtggttg cagtggcatc atcactgggt gccgtctctt tatccactgg    1020
taagcgtgca cctagccagc tggcaatcat accatcatag gcggcagtgt gttcaaatgc    1080
tttgactgcc aaatcaaaac gagtgttgtg gcttaaatga ccttggtttt ttagttcatc    1140
taggatgcgt gagtagtcat ttgggctggt gataatacca acatgggcat gattttggc     1200 ggctgagcgt accatagcag gcccaccaat atcaatattt tcaatcgcat cagacataac    1260
aacaccgtct ttggcgaccg tgttggcaaa tggatataaa ttcacgacaa cgatatcaat    1320
gcgatcaatg ccatgttcat tcataatggc atcatcaatg ccacgacggc ccaaaatacc    1380
accgtgaatt ttgggatgta gggtcttaac acgaccatcc atcatttcag caaaacctgt    1440
atgtgcagaa acctcaatgg cgtcaatccc atgttctttt aagagtttaa agtaccacc     1500 tgtggataaa ataccaaagc cggattctac caaaccttgg gcaaattcaa cgatttgcgt    1560
tttatctgag acggataata atgcataatt ttttgtcat                           1599

<210> SEQ ID NO 6
<211> LENGTH: 1099
<212> TYPE: DNA
<213> ORGANISM: Pneumocystis jirovecii

<400> SEQUENCE: 6
aaaccacttt gcgagtaagt atatataaat agaataatta ttttttaatt acaaattagc      60
gtatcgaatg accttgttca tcctattact ggattaccta tagtttctta tcttaagaaa    120
attgttaatc ctggtattaa accagttttg ccatttttat ataaaaatag aagtataaat    180
```

| | |
|---|---|
| tttagttctg aatttttataa agcgcctaca catattatgg ccattttaaa tcttactcct | 240 |
| gattctttt tcgatggggg tgttcattca tatgattcta tattaatgga tgtggagaat | 300 |
| tttataaatg caggggcgac gataattgat attggtgggc agtctacacg gcctggttca | 360 |
| catgttgttt ctatagagga agagatttct cgagttattc ctgctataaa atatctctta | 420 |
| aaagtatatc ctgatatttt agtaagtgta gatactttc gttctgaggt tgcagaacaa | 480 |
| gcaattaagg ctggtgctag tcttgttaat gatataagtg ggggaaggta tgatccaaaa | 540 |
| atgcttaatg tggttgccaa gttgaaagtt ccaatatgta taatgcatat gagaggtgat | 600 |
| ttttaacta tggacaattt aactgattat ggtaccgata ttataaaaca aattactaaa | 660 |
| gaattagaag aattgcttgt ttttgctgaa agttcaggta tttttaggtg aatattatt | 720 |
| ttagatcctg ggtaggatt tgctaaaact tcctatcaaa atatagaatt gttaagaaga | 780 |
| tttaatgaat taaaatctca gcattgcttt aatggtttgc cttggttgct tggtccaagt | 840 |
| cgcaaaagat ttacagggtg tcttacaggt gatgttatgc caaaagatag gatttggggc | 900 |
| actgctgctt cggttgccgc atctgtttta ggaggctgtg atattatacg ggttcatgat | 960 |
| gtttatgaaa tgtataaagt ttcaagaact ttggatgcta tttggaaagg agtttattga | 1020 |
| attgttatta tttatttgta aactataata tacataatac tttggttgat tgtaattttg | 1080 |
| caatttatat ttaaatatt | 1099 |

<210> SEQ ID NO 7
<211> LENGTH: 4109
<212> TYPE: DNA
<213> ORGANISM: Pseudomonas aeruginosa

<400> SEQUENCE: 7

| | |
|---|---|
| gaattcacct tcacttcgaa gctggtggac ggcaagttcc cggactacga gcgtgtactg | 60 |
| ccgcgcggtg gcgacaagct ggtggtcggt gaccgccagc aactgcgcga agccttcagc | 120 |
| cgtaccgcga tcctctccaa cgagaagtac cgcggcattc gcctgcagct ttccaacggt | 180 |
| ttgctgaaaa tccaggcgaa caacccggag caggaagagg ccgaggaaga agtgcaggtc | 240 |
| gagtacaacg gcggcaacct ggagataggc ttcaacgtca gttacctgct cgacgtgctg | 300 |
| ggtgtgatcg gtaccgagca ggtccgcttc atcctttccg attccaacag cagcgccctg | 360 |
| gtccacgagg ccgacaatga cgattctgcc tatgtcgtca tgccgatgcg cctctaaaca | 420 |
| tactgaatgt ccctgacccg cgtttcggtc accgcggtgc gcaacctgca cccggtgacc | 480 |
| ctctcccct cccccgcat caacatcctc tacggcgaca acggcagcgg caagaccagc | 540 |
| gtgctcgaag ccatccacct gctgggcctg gcgcgttcat tccgcagtgc gcgcttgcag | 600 |
| ccggtgatcc agtatgagga agcggcctgc accgtattcg ccaggtgat gttggccaac | 660 |
| ggcatcgcca gcaacctggg gatttcccgt gagcgccagg gcgagttcac catccgcatc | 720 |
| gatgggcaga acgccggag tgcggctcaa ttggcggaaa ctctcccact gcaactgatc | 780 |
| aacccggaca gctttcggtt gctcgaggga gcgccgaaga tccggcgaca gttcctcgat | 840 |
| tggggagtgt tccacgtgga acctcggttt ctgcccgtct ggcagcgcct gcagaaggcg | 900 |
| ctgcgccagc ggaactcctg gctccggcat ggtaaactgg accccgcgtc gcaagcggcc | 960 |
| tgggaccggg aattgagcct ggccagcgat gagatcgatg cctaccgcag aagctatatc | 1020 |
| caggcgttga aaccggtatt cgaggaaaca ctcgccgaat tggtttcact ggatgacctg | 1080 |
| acccttagct actaccgagg ctgggacaag gaccgggacc tcctggaggt tctggcttcc | 1140 |

```
agcctgttgc gcgaccagca gatgggccac acccaggcgg gaccgcagcg tgcggatctt      1200
cgcatacggt tggcaggtca taacgccgcg gagattctct cgcgcggtca gcagaagctg      1260
gtggtatgcg ccctgccgat cgcccaaggc catctgatca atcgcgccaa gcgcggacag      1320
tgcgtctacc tggtggacga cctgccctcg gaactggatg agcagcatcg aatggctctt      1380
tgccgttgct tgaagatttg ggttgccagg tattcatcac ctgcggtgga cccgcaacta      1440
ttgaaagacg gctggcgcac ggatacgccg gtatccatgt tccacgtgga acatggaaaa      1500
gtctctcaga ccacgaccat cgggagtgaa gcatgagcga gaacaacacg tacgactctt      1560
ccagcatcaa ggtgctgaag gggctggatg ccgtacgcaa gcgccccggc atgtacatcg      1620
gcgacaccga cgatggcacc ggtctgcacc acatggtgtt cgaggtggtg ataactcca       1680 tcgacgaagc gctggccggt tactgcagcg aaatcagcat caccatccat acggatgagt      1740
cgatcactgt ccgcgacaat ggacgcggta ttccggtgga tatccacaag gaagaagggg      1800
tttctgcggc ggaagtgatc atgaccgtcc tccacgccgg cggcaagttc gacgacaaca      1860
cctacaaggt gtccggcggc ttgcacgtgt gggcgtctc ggtggtgaac gcgctgtccc       1920
atgaactacg cctgaccatc cgtcgccaca caaggtctg gaacaggtc taccaccacg        1980 gcggttccgc agttcccact gcgcgaagtg ggcggaggac cgatggctcc ggcaccgaag      2040
ttcacttcaa gccgtccccg gagaccttca gcaacatcca cttcagttgg gacatcctgg      2100
ccaagcgcat ccgcgagctg tccttcctca actccggcgt cggcatcctg ctgcgcgacg      2160
agcgtaccgg caaggaggag ctgttcaagt acgaaggcgg tctgaaggcc ttcgtcgagt      2220
acctgaacac caacaagacc gcggtgaacg aggtattcca cttcaacgtc cagcgtgaag      2280
aggacggcgt gggtgtggaa gtcgccttgc agtggaacga cagcttcaac gagaacctgc      2340
tctgcttcac caacaacatc ccgcagcgtg acggcggcac ccacctggcc ggtttccgtt      2400
cggcgctgac gcgtaacctg aacaactaca tcgaggccga aggcctggcg aagaagttca      2460
agatcgccac caccggcgac gatgcccgcg aaggcctcac cgcgatcatc tcggtgaagg      2520
taccggaccc gaagttcagc tcgcagacca aggacaagct ggtctcctcc gaggtgaaga      2580
ctgcggtgga acaggagatg ggcaagtact tcgccgactt cctgctggag aatcccaacg      2640
aagccaaggc cgtggtcggc aagatgatcg acgccgcccg tgcccgcgag gccgcgcgca      2700
aggcgcgcga gatgacccgc cgcaagggcg cgctggacat cgccggcctg cccggcaaac      2760
tggccgattg ccaggaaaag gacccggcgc tctccgaact gtacatcgtg gagggtgact      2820
ccgcgggcgg ttccgccaag cagggccgca atcgccggac ccaggcgatc ctgccgctca      2880
agggcaagat cctcaacgtc gaaaaggcgc gcttcgacaa gatgctctcc tcccaggagg      2940
tcggtacgct gatcaccgcc ctgggctgtg gcatcggccg cgaggaatac aacatcgaca      3000
agctgcgcta ccacaacatc atcatcatga ccgatgctga cgtcgacggt tcgcacatcc      3060
gcaccctgct gttgaccttc ttcttccgcc agatgcccga gctgatcgag cgtggctaca      3120
tctacatcgc ccagccccg ttgtacaagg tcaagcgcgg caagcaggag cagtacatca       3180
aggacgacca ggccatggaa gagtacatga cccagtcggc cctggaagac gccagcctgc      3240
acgtcaacga gcacgctccg ggcctgtccg ggcggcgct ggagaaactg gtcaacgagt       3300 atcgcgggt gatcgccacc ctcaagcgcc tgtcgcgcct gtaccccag gagctgaccg        3360 agcacttcat ctacctgcct accgtgtcgg tggacgacct ggctaacgag tcggccatgc      3420
agggctggtt ggagaagttc caggcgcgcc tgaccgccgc cgagagtcc ggcctgacct       3480 acaaggccag cctgcgcgaa gaccgcgagc gccacctgtg gctgcccgag gtggaactgg      3540
```

```
tggcccacgg cctgtccagc tacgtcacct tcaaccgtga cttcttcgcc agcaatgact    3600
accgctcggt gtcgctgctc ggcgaccagc tgaacagcct gctggaagac ggcgcctacg    3660
tgcagaaggg tgagcgcaag cgcccgatca gcgccttcaa ggacggcctg gactggctga    3720
tggccgaagg taccaagcgc cacagcatcc agcgatacaa ggggctgggc gagatgaacc    3780
ctgagcagct gtgggaaacc accatggatc cgaacgtccg gcgcatgctg aaggtgacca    3840
tcgaggatgc catcgccgcc gaccagatct tcaacaccct gatgggcgat gccgtggagc    3900
cgcgccgcga cttcatcgaa agcaacgcgc tggcggtgtc gaacctggac gtgtgacagg    3960
tcggcagacg accctcatgg aaaccccggc ctggcgccgg ttttctttt tgcgccaggt    4020 agcctggata cggcgccagg ggtgcttgca aggtgtggcg agccggttac tcggccggca    4080
ttggacctgg accggctctg cggctgcac                                      4109

<210> SEQ ID NO 8
<211> LENGTH: 1578
<212> TYPE: DNA
<213> ORGANISM: Staphylococcus aureus

<400> SEQUENCE: 8
ttaactaatg agtttaatt tataatcatg tatcgtttgc aattcaccat cgacttttcg      60
atatacaata tgatcagcag taatttctgt aggactggat acgccaacag ctgctgcaat    120
attgaataag ccttcatgca aacttgttac atagtttgtg acacgatatt gcttttctcc    180
aacaatcaat gcttttctt ttttcgcatc tgtcgttgca acacctacag gacatgtatt    240
catatgacat tgttgactca taatacaacc gacactaatc atcatgccac gtgcaatatt    300
aacaaaatct gcacctaaac ctagtgcaat cgcaatttta tctggtgtca ctaacttacc    360
agatgccgcc aatttcactt tatctcgaat accatatttt tctaacatgc cagacacaat    420
aggtagagct gtaaatagcg gtaagccaac accatcttgt aattcttgga atgttgcacc    480
agtaccacct tcaccaccat caatcgtaat aaagcttgga tacttatcta gttccaccat    540
cgtacgtaca agtgtttcaa tttctgaaac tttgcttact acaattttga atcctactgg    600 ttttgacct aattgctgca actgatcgac gaaacgaatc aaatcttcag cattatgaat    660
aaattcgtaa cggttaggtg aattgattgt tttataaggt tcaacatttc ggattttagc    720
aatttcttcg tttacctttt cagcttccat atgaccacca cgagtcttag caccttgtgc    780
caacttcagc tcaaatgcgc gtacgttaga taactgtgcg acctctttaa ataaaccttc    840
actaaaatta ccttctttat cacgaacacc aaataaaccg ggaccaattt ggaaaatgat    900
atccccatta cctttaaat gatattctga taagccacct tcacctgtat tcatccaagt    960
gcccgcttta gctagccctt tagataaagc tgtaatggca tttttttccta aagcgccata   1020 actcatacca gattgtccta cgatacgttt taaaataaat ggatgttttta aatgttcacc   1080 taatttatt gcatggtcat cacttaagta atacggatca atctttgtcg gtacacgata   1140
ttcttcacga ctaaatagac gctcattcgc gattttataa atgaatgttg ataacaatgt   1200
tgtattatct actgaaatct cattacgttg catcggaaac attgtgttct gtatgtaaaa   1260
gccgtcttga taatctttag tagtaccgaa gctggtcata cgagagttat attttccagc   1320
caaaacgata ttttatatt cattacgtga aaaggtttc ccttcattat ccccagaaaa   1380
taaatactga cgtaattccg gtcccatttt ttctgaaata tatctaatac gtgctagtaa   1440
aggataattc cttaatacac tatgttgtga ttgtctttta tctttaatta accaaataag   1500
```

```
cccgataaca ataaccgtaa gcatgaagcc tacaacgata atgttaacta taaattgcat    1560
gactgtaaga aacgtcat                                                  1578

<210> SEQ ID NO 9
<211> LENGTH: 1785
<212> TYPE: DNA
<213> ORGANISM: Toxoplasma gondii

<400> SEQUENCE: 9
acctggttga tcctgccagt agtcatatgc ttgtcttaaa gattaagcca tgcatgtcta      60
agtataagtt tttatacggc taaactgcga atggctcatt aaaacagtta tagtttattt     120
gatggtcttt actacatgga taaccgtggt aattctatgg ctaatacatg cgcacatgcc     180
tcttcccctg gaagggcagt gtttattaga tacagaacca acccaccttc cggtggtcct     240
caggtgattc atagtaaccg aacggatcgc gttgacttcg gtctgcgacg gatcattcaa     300
gtttctgacc tatcagcttt cgacggtact gtattggact accgtggcag tgacgggtaa     360
cggggaatta gggttcgatt ccggagaggg agcctgagaa acggctacca catctaagga     420
aggcagcagg cgcgcaaatt acccaatcct gattcaggga ggtagtgaca agaaataaca     480
acactggaaa tttcatttct agtgattgga atgataggaa tccaaacccc tttcagagta     540
acaattggag ggcaagtctg gtgccagcag ccgcggtaat tccagctcca atagcgtata     600
ttaaagttgt tgcagttaaa aagctcgtag ttggatttct gctggaagca gccagtccgc     660 cctcagggt gtgcacttgg tgaattctag catccttctg gatttctcca cacttcattg      720
tgtggagttt tttccaggac ttttactttg agaaaattag agtgtttcaa gcaggcttgt     780
cgccttgaat actgcagcat ggaataataa gataggattt cggccctatt tgttggtttt     840
ctaggactga agtaatgatt aatagggacg gttgggggca ttcgtattta actgtcagag     900
gtgaaattct tagatttgtt aaagacgaac tactgcgaaa gcatttgcca agatgttttt     960
cattaatcaa gaacgaaagt taggggctcg aagacgatca gataccgtcg tagtcttaac    1020
cataaactat gccgactaga gataggaaaa cgtcatgctt gacttctcct gcaccttatg    1080
agaaatcaaa gtctttgggt tctggggga gtatggtcgc aaggctgaaa cttaaaggaa     1140
ttgacggaag ggcaccacca ggcgtggagc ctgcggctta atttgactca cacggggaa     1200 actcaccagg tccagacata ggaaggattg acagattgat agctctttct tgattctatg    1260
ggtggtggtg catggccgtt cttagttggt ggagtgattt gtctggttaa ttccgttaac    1320
gaacgagacc ttaacctgct aaataggatc aggaacttcg tgttcttgta tcacttctta    1380
gagggacttt gcgtgtctaa cgcaaggaag tttgaggcaa taacaggtct gtgatgccct    1440
tagatgttct gggctgcacg cgcgctacac tgatgcatcc aacgagttta taaccttggc    1500
cgataggtct aggtaatctt gtgagtatgc atcgtgatgg ggatagatta ttgcaattat    1560
taatcttcaa cgaggaatgc ctagtaggcg caagtcagca gcttgcgccg attacgtccc    1620 tgcccttgt acacaccgcc cgtcgctcct accgattgag tgttccggtg aattattcgg     1680
accgttttgt ggcgcgttcg tgcccgaaat gggaagtttt gtgaacctta acacttagag    1740
gaaggagaag tcgtaacaag gtttccgtag gtgaacctgc ggaag                    1785

<210> SEQ ID NO 10
<211> LENGTH: 1797
<212> TYPE: DNA
<213> ORGANISM: Ureaplasma parvum
```

<400> SEQUENCE: 10

```
atgtttaaaa tttcaagaaa aaattattca gatttatacg gtattacaac tggtgatagc      60
gttagattag gagatacaaa tctttgagtt aaagttgaaa aagacttaac tacttatggt     120
gaagaatctg tttttggtgg tggaaaaacc ctacgtgaag gtatgggaat gaattctact     180
atgaagttag atgataaatt aggtaatgct gaagtaatgg atttagttat tacaaatgca     240
ctaattgttg attatacagg tatttataaa gcagatattg gtattaaaaa tggaaaaatt     300
gctgcgattg gtaaatctgg aaatccacat ttaacagata tgttgatat gattgtgggt      360
atctcaactg aaatttcagc tggtgagggt aaaatttata cagctggtgg tttagatact     420
cacgttcact gactagaacc agaaatagtt cctgttgcat tagatggtgg tattacaact     480
gttattgctg gtggtacagg tatgaatgat ggtacaaaag ccacaactgt ttcacctggt     540
aaattttgag ttaaatcagc tttacaagca gctgatggat tatcaattaa tgccggtttt     600
ttagctaaag gtcaaggtat ggaagatcca atttttgagc aaattgctgc tggagcttgt     660
ggacttaaaa tccatgaaga ctgaggggca acaggaaatg cgattgattt agcattaaca     720
gttgctgata aaactgatgt agctgttgct attcatacag atacattaaa tgaagctgga     780
tttgtagaac atacaattgc agctatgaaa gggcgaacaa ttcatgctta tcatacagaa     840
ggtgctggtg agggcatgc tccagatatt ctagaaactg ttaaatatgc ccatatttta      900
ccagcttcta caaacccaac aattccttat acagtaaata caattgctga acatttagat     960
atgttaatgg tatgtcacca cttaaatcct aaggttccag aagatgttgc ttttgctgat    1020
tcacgtattc gtagccaaac aattgcagct gaagacttat tgcacgatat gggtgcaatt    1080
tcaattatgt catcagatac attagctatg ggacgtattg gcgaagttgc aactcgtaca    1140
tgacaaatgg ctcacaaaat gaaagcacaa tttggatcat taaaggtga tagtgaattc     1200
agtgataaca tcgtgtaaa acgttatatt tctaaatata caattaaccc agctattgca    1260
catggtgttg attcttatat tggttcacta gaagttggta aattagctga tattgttgct    1320
tgagaaccta aattctttgg tgcaaaacct tattatgttg taaaaatggg tgtaatcgct    1380
cgttgtgtag caggtgatcc aaatgcttca attccaacat gcgaacctgt aattatgcgt    1440
gaccaatttg gaacttatgg acgtttgtta actaatacat cagtaagttt tgtttcaaaa    1500
attgggttag aaaatggcat taagaggaa tataaattag aaaaagaatt attaccagtt     1560
aaaaattgcc gttcagtaaa taaaaagagt atgaaatgaa actctgcgac tccaaattta    1620
gaagttgatc cgcaaacttt tgatgctgct gttgattta atgatttaga aaattgacta     1680
gaacaatcag cttctgaatt agctaaaaaa ttaaaaaga cttcaagtgg caaatatata    1740
cttgatgctg aacctttaac agaagcgcca ttagcacaaa gatatttctt attttaa       1797
```

<210> SEQ ID NO 11
<211> LENGTH: 1025
<212> TYPE: DNA
<213> ORGANISM: Ureaplasma urealyticum

<400> SEQUENCE: 11

```
gtatttgcaa tctttatatg ttttcgttaa aattaaaatt cctataaaaa caacatgaga      60
ttaaacaaaa tcttaatgtt gttattatct atacattcta agaaaaata tatttgcaaa     120
actataaata gacacaaaaa acaatagaat aataaaacta aatttcatat ttagtttatt     180
aggagatcgt tataaatgaa attattaaaa aataagaaat tttgagcaat tacactaggg     240
```

| | |
|---|---|
| gtaactttag tgggagcagg ggtagttgct gtggcagctt catgttctag ctcaaatgtt | 300 |
| aaatctaaat taagtagtca acttgttaaa tcaaaagacg aaaagagctt ttacgctgtt | 360 |
| tacgacattg aaaatttcga tgatttaact gaaaatgata aaaaagcatt aaacgaagct | 420 |
| gaattcaatg ttgcaattac atcagctgaa aataaaacag aaaacgcaac aacaaaaggt | 480 |
| cacttactta acaaaaaaat ctatgttaaa ttaccacgtg aaccaaaagc taagaacaa | 540 |
| ttaactatta ttaataaagg tggcttacta aaaactgcat ctttagtatt acctgataat | 600 |
| tttaattatc aaacagaaaa agtagacttt gaaaatgcgc ctacaccaac tccagaacct | 660 |
| actccaacac ctacaccaaa agaagataaa gcaattgtaa gtaatgttga gtttagcgaa | 720 |
| gttaatgcac aaacaaaaac agcaaaagtt aaattaacat ttgcctcagc agttcaacta | 780 |
| aaagacgaaa gccaaaaatc attgaaatta actttaacta agatagtga aacaaaagaa | 840 |
| gttgacttag tattaagtca agataaatta agtgcaacag ctgatttaaa tgtgttaaat | 900 |
| gaaggaactt ataagtaac taaattaact ttaaatggta atgaagttag tttaaatgac | 960 |
| gaaattaaaa ataagaatt aaaagtagaa gcttctaaaa acctgaaac aggtagcaca | 1020 |
| gaagg | 1025 |

<210> SEQ ID NO 12
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 12
tatttttatt tcagcctgct cacctt    26

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 13
aaatacttct gtggtggttg cctta    25

<210> SEQ ID NO 14
<211> LENGTH: 29
<212> TYPE: DNA
<213> ORGANISM: Artificial Sequence
<220> FEATURE:
<223> OTHER INFORMATION: Synthetic oligonucleotide probe

<400> SEQUENCE: 14
tgactgctaa tccaaatcac agcgcttca    29

<210> SEQ ID NO 15
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 15
gtctcggtgg tgaacg    16

<210> SEQ ID NO 16
<211> LENGTH: 20

<212> TYPE: DNA
<213> ORGANISM: Artificial Sequence
<220> FEATURE:
<223> OTHER INFORMATION: Synthetic oligonucleotide primer

<400> SEQUENCE: 16
tggatgttgc tgaaggtctc                                          20

<210> SEQ ID NO 17
<211> LENGTH: 26
<212> TYPE: DNA
<213> ORGANISM: Artificial Sequence
<220> FEATURE:
<223> OTHER INFORMATION: Synthetic oligonucleotide probe

<400> SEQUENCE: 17
tccgtcgcca caacaaggtc tgggaa                                   26

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 18
tgctgcataa aggcatcgtt                                          20

<210> SEQ ID NO 19
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 19
ccaccgaggc cagcaa                                              16

<210> SEQ ID NO 20
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 20
acgctgagca cctcctgcaa cgt                                      23

<210> SEQ ID NO 21
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 21
ggtggtcctc aggtgat                                             17

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide primer

```
<400> SEQUENCE: 22
ccacggtagt ccaatacagt a                                              21

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide probe

<400> SEQUENCE: 23
atcgcgttga cttcggtctg cgac                                           24

<210> SEQ ID NO 24
<211> LENGTH: 16
<212> TYPE: DNA
<213> ORGANISM: Artificial Sequence
<220> FEATURE:
<223> OTHER INFORMATION: Synthetic olignucleotide primer

<400> SEQUENCE: 24
ggtgagttgc cacagc                                                    16

<210> SEQ ID NO 25
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 25
agtagaccgc cattgactc                                                 19

<210> SEQ ID NO 26
<211> LENGTH: 26
<212> TYPE: DNA
<213> ORGANISM: Artificial Sequence
<220> FEATURE:
<223> OTHER INFORMATION: Synthetic oligonucleotide probe

<400> SEQUENCE: 26
cacagcgggc agctcaattt gaccta                                         26

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 27
gagcatcagg gtggctatac g                                              21

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 28
atagtctgcc agttcagttc                                                20

<210> SEQ ID NO 29
```

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide probe

<400> SEQUENCE: 29
tacggcgtga catcggcttc aaatg                                              25

<210> SEQ ID NO 30
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 30
cgggttaggt gaattgattg ttttat                                             26

<210> SEQ ID NO 31
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 31
cgcatttgag ctgaagttg                                                     19

<210> SEQ ID NO 32
<211> LENGTH: 30
<212> TYPE: DNA
<213> ORGANISM: Artificial Sequence
<220> FEATURE:
<223> OTHER INFORMATION: Synthetic oligonucleotide probe

<400> SEQUENCE: 32
ttccatatga ccaccacgag tcttagcacc                                         30

<210> SEQ ID NO 33
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 33
taatggtttg ccttggttgc tt                                                 22

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 34
cacagcctcc taaaacagat                                                    20

<210> SEQ ID NO 35
<211> LENGTH: 34
<212> TYPE: DNA
<213> ORGANISM: Artificial Sequence
<220> FEATURE:
<223> OTHER INFORMATION: Synthetic oligonucleotide probe

```
<400> SEQUENCE: 35
acagggtgtc ttacaggtga tgttatgcca aaag                              34

<210> SEQ ID NO 36
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 36
ggtgtaaagg tttcgactta gaa                                          23

<210> SEQ ID NO 37
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 37
cgaacaccgg gtcacc                                                  16

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 38
atgcggaggg cgttggctgg                                              20

<210> SEQ ID NO 39
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 39
atttcatatt tagtttatta ggagatcgtt at                                32

<210> SEQ ID NO 40
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 40
agatttaaca tttgagctag aacat                                        25

<210> SEQ ID NO 41
<211> LENGTH: 27
<212> TYPE: DNA
<213> ORGANISM: Artificial Sequence
<220> FEATURE:
<223> OTHER INFORMATION: Synthetic oligonucleotide probe

<400> SEQUENCE: 41
cacagcaact acccctgctc ccactaa                                      27

<210> SEQ ID NO 42
```

```
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 42
acagataatg ttgatatgat tgtgggtat                                    29

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 43
ctaatgcaac aggaactatt tctg                                         24

<210> SEQ ID NO 44
<211> LENGTH: 30
<212> TYPE: DNA
<213> ORGANISM: Artificial Sequence
<220> FEATURE:
<223> OTHER INFORMATION: Synthetic oligonucleotide probe

<400> SEQUENCE: 44
tcagtgaacg tgagtatcta aaccaccagc                                   30

<210> SEQ ID NO 45
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 45
ggtttagata ctcacgttca ctga                                         24

<210> SEQ ID NO 46
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 46
gcttttgtac catcattcat acctgt                                       26

<210> SEQ ID NO 47
<211> LENGTH: 32
<212> TYPE: DNA
<213> ORGANISM: Artificial Sequence
<220> FEATURE:
<223> OTHER INFORMATION: Synthetic oligonucleotide probe

<400> SEQUENCE: 47
ccaccagcaa taacagttgt aataccacca tc                                32

<210> SEQ ID NO 48
<211> LENGTH: 29
<212> TYPE: DNA
<213> ORGANISM: Artificial Sequence
<220> FEATURE:
<223> OTHER INFORMATION: Synthetic oligonucleotide primer
```

<400> SEQUENCE: 48
gctatggtaa taaatggaca atgaaataa					29

<210> SEQ ID NO 49
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 49
gcttctgttg ccaggtg					17

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 50
accccgctta aacctgcgac g					21

<210> SEQ ID NO 51
<211> LENGTH: 26
<212> TYPE: DNA
<213> ORGANISM: Artificial Sequence
<220> FEATURE:
<223> OTHER INFORMATION: Synthetic oligonucleotide probe

<400> SEQUENCE: 51
ctaaatgagt agttgcaaat gacaac					26

<210> SEQ ID NO 52
<211> LENGTH: 616
<212> TYPE: DNA
<213> ORGANISM: Bartonella spp.

<400> SEQUENCE: 52
tctgcgccat ctcctctcca agaattagcg gctgtacttt aaaaccgcat catatagctt					60 cataaataat tagagaattt aaaatattaa caaccccccct tttccaaaga ctgttcttca					120 tctatattta gagagctggc ttaccagcta tggtaataaa tggacaatga aataaactca					180 ttggacccgg gggcggtacc cggcgcctcc accaaaatat aacaaaaatt atattttggt					240 gggggcgaaa taggatcgac aagggtgtaa agattgctct tttactcggc atagtaccac					300 cgtcatcgga ctaaatgagt agttgcaaat gacaactatg cggaagcacg tctcgctgct					360 taatgtagtg tgaatgtttc aaactaagcc ttaaatcgtc gcagatttaa gcggggttcg					420 aaggcacctg gcaacagaag ccttcacttt gtacgtatta ttaattgatt tttcagacac					480 tatttgtcat aaatttcgtg tttttctcga ttaatgaaat gcattgtaaa taaatatttt					540 ctagcttaaa gaaacattgc attgcatgat atcatttatg ctcagctgct gtataaaata					600 aaaggaataa gctttg					616

<210> SEQ ID NO 53
<211> LENGTH: 768
<212> TYPE: DNA
<213> ORGANISM: Streptococcus agalactiae

<400> SEQUENCE: 53

```
ttatttaat gctgtttgaa gtgctgcttg taatgttaca atctcttgat caacttgttg        60
taccgtaaca tttggattca actgaactcc aacagcatgt gtgattgctt tatttaaagt       120
attgtaaact ttaaattctt tgacgttaag tactttttta tctctagtaa agcgtgtatt       180
ccagatttcc ttatcaagtt ttgattttgt atagattgta gctctatcag ttggttttaa      240
atcaggataa gttaaaacct tttgttctaa tgccttaca tcgttaactt gagctttaat       300
tgaatcaact gaagcaaatg gatctaaaat gcgaataacc agcttagtta tcccaaatcc      360
catatcaata tttgcttgac taaccttatt tgctaaatgt tgagttgaaa aagtgattgc      420
ttcaatcaca tctgttaagg cttctacacg actaccaata gaattcaaat cataaactgt      480
ctcagggttg gcacgcaatg aagtctttaa tttttcaaca ctagtaatag cctcattaac      540
cgttttttca taatctgttc cctgaacatt atctttgata tttctcaact gaatgctatc      600
ttgatcaagc ttttgagcca tttgctgggc ttgattatta ctgtttacat gatttaccac      660
ttgtggagtt gtcacttgat cagcatgtac ttctaataca gctggtgaaa ataacaatgc      720
accagccact agagttccag atagatacat catatgttta acgttcat                   768
```

<210> SEQ ID NO 54
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 54

```
gggaacagat tatgaaaaac cg                                                22
```

<210> SEQ ID NO 55
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 55

```
aaggcttcta cacgactacc aa                                                22
```

<210> SEQ ID NO 56
<211> LENGTH: 28
<212> TYPE: DNA
<213> ORGANISM: Artificial Sequence
<220> FEATURE:
<223> OTHER INFORMATION: Synthetic oligonucleotide probe

<400> SEQUENCE: 56

```
agacttcatt gcgtgccaac cctgagac                                          28
```

<210> SEQ ID NO 57
<211> LENGTH: 2172
<212> TYPE: DNA
<213> ORGANISM: Klebsiella pneumoniae

<400> SEQUENCE: 57

```
atgcttgata aaattaacat taatatcaaa aaaactctgt tggcctttct cgtcagttta        60
gtcgctattc cgctggctcg tttatttca ccgcaaacgg ttattgatgg caatcttatt       120
tatattgcct ggctgccaat cagcgtgatg ttttctgtta tttttatctt tggccgctat      180
```

```
gcgatcgcac cattaattct cgcgtttgcc attaccaata gctttctcat tgaattaacg    240
ctgtcacagg cgcttattct gctcttttgt cagctgtttg ctgtgtttgt ctcctgcgct    300
gttttacgcc tgatggtggg caagcgctgg cggtgtggcc ccacggcgaa acatatgggg    360
gcgcggatct tctggggcgg cttcttcgcg ccggtactgt tgaaaatcac catgtacctt    420
gccgggcaat attttgcgtt tccattatct attaccagtt actttggtag tatgccgttg    480
atttataccg taatagatat ccaaagttta atcagcgcgg cattaatttt tacgacgttt    540
ctttattatc caatgcggat gattatcagt ccgcactatg cccgacgttt ctggcgtcag    600
gaatgtttac catggctagc acccaaacat cgttcttta cctatattg gtttatctcg      660 ctggcgcttt tattaacttt actgtgtgcg ccgtatcagt ctgaatttat tgccggttat    720
ttagttccgg tgatatttat tgtctacttt atcgggatta gtcggattgg tcatgcgctg    780
ctgcgtattt catggtctgt ctcagccttt ttactggtgg tgtataataa aaactttctc    840
cagggcgtcc agagcgagta ttcattatcc tttgtgctgt cagtcctgat ctccttcact    900
atctgtttgt tttatatggc agacacctat gcccgcagcg atcgcaataa acgccgctgg    960
cgtagccagg cggaagagga tccgctgacg ggcttaccta atctgcgcgc gctggtgagc   1020
catttacaga gcagtcctct gcaggctatc tgcagcttgc gtatcgataa tctcgatttt   1080
cttagccgac attatgggct aatgatgggc gtggactgta aacggcaaat catccgggcg   1140
cttcagccgc tgttggggc aacggataaa gtcttccagg ttcccggcag cgaattgatc    1200
ctcgtgcttg acgggccgga ccctgcggcg cggctaaacc atatggtcgc catcctcaac   1260
cacaaaaagt tcagctggca taatcagccg ctggatcttg agtttggcgc ggcatggagc   1320
cgtgatgacg gtcagggtga gacgctgcac cagatgctgg gccagctcag ctggcttttcc   1380 gaacaggcgg gcagtgaacg ccgggtactg gcgttggatg aggagcagga gctggtggtg   1440
gatcaaacca ccgagcaggt acgcctcctg atgcgcgtca gcaggttct caaagagcgg    1500 gcgctggtgc tctatgcgca accgattcaa aacgcggagg gggagggcta tcatgagatc   1560
ctcacgcgca tgcgctgtgg tgacggcgtc attatgccgg atcagtttat tccgctgatt   1620
gtgcagttta acctcagcca gcgttttgac atgctggtgc ttgagaccct gttcagttcg   1680
ctccatcagc atcccggcca gcggttctcg gtcaatctgc tgccttcaac cctgatgcaa   1740
aaggacagcg cggcgcagat tatcgcgctg tttcaacgct atcgcatttc gccagatctt   1800
atcaccattg aggtgaccga agagcaggct ttctccaatg ccgacaccag ccagcaaaat   1860
ctcgacgcgc tgcgcgcgtt tggctgcgct atcgccattg atgactttgg caccggttat   1920
gcgaactatg aacgactgaa gcatctgcag gccgatatca ttaagattga cggctgcttc   1980
gtccgcgaca ttctgacgga cccgctggac gccattatgg tgaaatcgat tgtcgaaatg   2040
gcgcgggcga acagatgag cgtggtggcg gaatatgtcg aaagcgaatc gcaaaaagcg    2100
cgcctgctgg aactgggcgt gaattatctg cagggttacc tggtcggtaa gcctcagccg   2160
ttgggcgaat ga                                                       2172
```

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 58
tgcagataat tcacgcccag                                                 20

<210> SEQ ID NO 59
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 59
acccgctgga cgccat                                                  16

<210> SEQ ID NO 60
<211> LENGTH: 23
<212> TYPE: DNA
<213> ORGANISM: Artificial Sequence
<220> FEATURE:
<223> OTHER INFORMATION: Synthetic oligonucleotide probe

<400> SEQUENCE: 60
ccaccacgct catctgtttc gcc                                          23

<210> SEQ ID NO 61
<211> LENGTH: 561
<212> TYPE: DNA
<213> ORGANISM: Neisseria meningitidis

<400> SEQUENCE: 61
ttatttaatc acgccacatg ccatacgtgg gccgccaccg ccaagtggag ctggatgatc    60
ggagtgatta tcaccacccg tgtggatcat aatagagtga ccgcgaacat catctaaatg   120
tttaagacgt ggtgctaaaa caggatttgt tgctgtgcca tcatgcaata cagttaatgc   180
aggtaaatca cctaagtgtg catcatcttg ccatgggtaa ccatgttgtt ttgcaccttt   240
aggatcccag tgaccgcctg cgcctaaacc agctgtcaat ttaccttctt tttcttttgg   300
ctcacagctt gggttttcat ggatgtggaa accatgtaag ccttcgctta atccttgtaa   360
atcaggggta aacacaagac catagttaga ttcagtaata gtcactgtac ccacatcttt   420
gttaccgttt actggatcaa gttgttcac tttcacttca atagaagcac ctttaggtat   480
cgtattatgc tcgtgtgctt gcgcaacacc aactgaacat actgcactaa ccgctagtgc   540
taataaggtt ttcatattca t                                            561

<210> SEQ ID NO 62
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 62
ctgtgagcca aagaaaaag aag                                           23

<210> SEQ ID NO 63
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 63
gatttgttgc tgtgccatca t                                            21

<210> SEQ ID NO 64

```
<211> LENGTH: 20
<212> TYPE: DNA
<213> ORGANISM: Artificial Sequence
<220> FEATURE:
<223> OTHER INFORMATION: Synthetic oligonucleotide probe

<400> SEQUENCE: 64
cgcaggcggt cactgggatc                                               20

<210> SEQ ID NO 65
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 65
ctcaccagga gattacaaca tgg                                           23

<210> SEQ ID NO 66
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 66
agctcagacc aaaagtgacc atc                                           23

<210> SEQ ID NO 67
<211> LENGTH: 22
<212> TYPE: DNA
<213> ORGANISM: Artificial Sequence
<220> FEATURE:
<223> OTHER INFORMATION: Synthetic oligonucleotide probe

<400> SEQUENCE: 67
caccgacggc gagaccgact tt                                            22
```

REAL-TIME PCR FOR THE DETECTION OF PATHOGENS

CROSS REFERENCE TO RELATED APPLICATIONS

This is a divisional of co-pending U.S. application Ser. No. 16/056,147, filed Aug. 6, 2018, which is a divisional of U.S. application Ser. No. 14/398,390, filed Oct. 31, 2014, now U.S. Pat. No. 10,072,305, issued Sep. 11, 2018, which is the § 371 U.S. National Stage of International Application No. PCT/US2013/028034, filed Feb. 27, 2013, which was published in English under PCT Article 21(2), which in turn claims the benefit of U.S. Provisional Application No. 61/642,091, filed May 3, 2012, each of which is incorporated herein by reference in its entirety.

FIELD

This disclosure concerns methods and compositions related to the detection of pathogens, particularly utilizing real-time PCR.

BACKGROUND

Many pathogens have major public health and economic impact. Pathogens may be spread in the community or in a clinic or hospital setting, and multidrug resistance is a growing problem in many pathogens. Furthermore, although a presumptive clinical diagnosis can often be made through symptomology, a laboratory identification determining the etiology of a disease is critical to establish the correct course of treatment. Current tests for many pathogens are neither highly sensitive nor specific, and in some cases require an acute and convalescent patient serum (paired serum) for clear identification. Thus, a need remains for rapid, cost-effective, sensitive, and specific assays for many pathogens. In particular, there is a need for assays for diagnosing and differentiating major pathogens of childhood and neonatal infection, which cause significant neonatal mortality throughout the world.

SUMMARY

Disclosed herein are methods for detecting presence of one or more of *Acinetobacter baumannii*, *Pseudomonas aeruginosa*, *Klebsiella pneumoniae*, *Toxoplasma gondii*, *Moraxella catarrhalis*, *Escherichia coli*, *Shigella*, *Staphylococcus aureus*, *Pneumocystis jirovecii*, *Chlamydia trachomatis*, *Ureaplasma urealyticum*, *Ureaplasma parvum*, *Ureaplasma* spp., *Bartonella* spp., *Streptococcus agalactiae* (Group B *Streptococcus*; GBS), and/or *Neisseria meningitidis* nucleic acids in a sample, such as a biological sample obtained from a subject, or an environmental sample. In particular, these pathogens are some of the most common causes of infection in neonates and young children, and are major causes of mortality in children under the age of five. The methods provided herein include simultaneous multipathogen detection assays, which can be used to diagnose and differentiate causes of neonatal infection. In addition, since all of these assays target infectious agents, all population groups may benefit from the advancements described herein. Depending on the specific circumstances and epidemiological data associated with sporadic and/or outbreak-linked cases, the disclosed methods can provide a valuable diagnostic tool for the clinician and medical epidemiologist charged with determining the etiology of a disease.

The disclosed methods can be used to detect presence of one or more (or any combination of two or more thereof) of *Acinetobacter baumannii*, *Pseudomonas aeruginosa*, *Klebsiella pneumoniae*, *Toxoplasma gondii*, *Moraxella catarrhalis*, *Escherichia coli*, *Shigella*, *Staphylococcus aureus*, *Pneumocystis jirovecii*, *Chlamydia trachomatis*, *Ureaplasma urealyticum*, *Ureaplasma parvum*, *Ureaplasma* spp., *Bartonella* spp., *Streptococcus agalactiae*, and/or *Neisseria meningitidis* nucleic acids in a sample, for example, by contacting a sample with one or more of the probes disclosed herein (such as one or more of SEQ ID NOs: 14, 17, 20, 23, 26, 29, 32, 35, 38, 41, 44, 47, 50, 56, 60, and 64) and detecting hybridization of one or more of the probes with a nucleic acid in the sample. The disclosed methods provide rapid, sensitive, and specific detection of these organisms, for example, utilizing real-time simultaneous multipathogen detection or a multiplex real-time PCR assay.

In some embodiments, the disclosed methods further include amplifying one or more (or any combination of two or more thereof) of an *Acinetobacter baumannii*, *Pseudomonas aeruginosa*, *Klebsiella pneumoniae*, *Toxoplasma gondii*, *Moraxella catarrhalis*, *Escherichia coli*, *Shigella*, *Staphylococcus aureus*, *Pneumocystis jirovecii*, *Chlamydia trachomatis*, *Ureaplasma urealyticum*, *Ureaplasma parvum*, *Ureaplasma* spp., *Bartonella* spp., *Streptococcus agalactiae*, and/or *Neisseria meningitidis* nucleic acid, for example utilizing one or more primers (such as one or more of SEQ ID NOs: 12, 13, 15, 16, 18, 19, 21, 22, 24, 25, 27, 28, 30, 31, 33, 34, 36, 37, 39, 40, 42, 43, 45, 46, 48, 49, 51, 54, 55, 58, 59, 62, and/or 63).

This disclosure also provides kits for detecting one or more of *Acinetobacter baumannii*, *Pseudomonas aeruginosa*, *Klebsiella pneumooniae*, *Toxoplasma gondii*, *Moraxella catarrhalis*, *Escherichia coli*, *Shigella*, *Staphylococcus aureus*, *Pneumocystis jirovecii*, *Chlamydia trachomatis*, *Ureaplasma urealyticum*, *Ureaplasma parvum*, *Ureaplasma* spp., *Bartonella* spp., *Streptococcus agalactiae*, and/or *Neisseria meningitidis* in a sample, for example, including one or more of the probes and primers disclosed herein.

The foregoing and other features, of the disclosure will become more apparent from the following detailed description, which proceeds with reference to the accompanying figures.

BRIEF DESCRIPTION OF THE DRAWINGS

FIG. 1C shows Ct values of serial dilutions of *K. pneumoniae* spiked into saline (to mimic NP/OP swab) or blood. Error bars display standard deviation. * $p<0.0001$ compared to no treatment. #$p<0.05$ compared to same concentration of organisms in saline.

FIGS. 3A and 3B are a pair of diagrams showing effect of enzyme system on detection of pathogen targets in primary clinical specimens. Data shown are difference in Ct value between reactions using Quanta One-step RT-PCR TOUGH-MIX® and AGPATH-ID™ One-step RT-PCR kit when testing TNA extracted from NP/OP swabs (FIG. 3A) or blood (FIG. 3B). Each data point represents the difference in Ct value between the two reactions for an individual clinical specimen. Median difference is indicated (–) for assays with ≥2 positive results. *Targets that were only detected using AGPATH-ID™ always occurred when Ct values were >33.

SEQUENCE LISTING

Figure 1A:
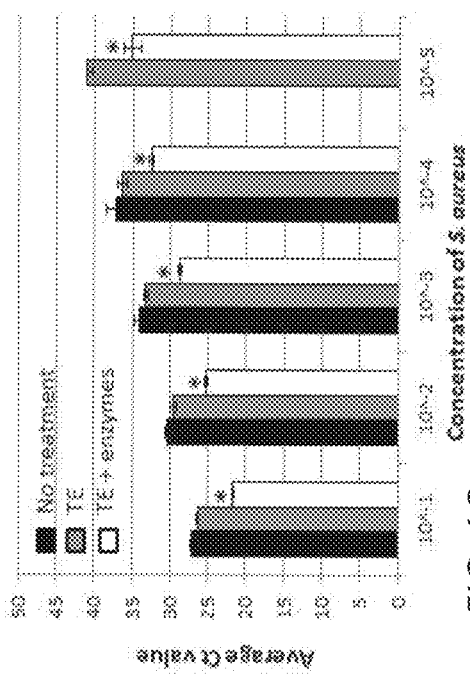
FIGS. 1A-1C are a series of graphs showing the effect of lytic enzyme treatment on extraction of nucleic acid from blood specimens. Average Ct value of individual real-time PCR reactions (n=4) containing TNA extracted from healthy donor blood spiked with serial dilutions of *S. aureus* (FIG. 1A) or *K. pneumoniae* (FIG. 1B) without treatment, after incubation with TE buffer alone, or after treatment with TE buffer with lytic enzymes (lysozyme, lysostaphin, and mutanolysin) at 37° C. for 30 minutes.

Any nucleic acid and amino acid sequences listed herein or in the accompanying sequence listing are shown using standard letter abbreviations for nucleotide bases, and three letter code for amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Sep. 27, 2021, and is 41,259 bytes, which is incorporated by reference herein.

SEQ ID NO: 1 is an exemplary *Acinetobacter baumannii* oxa-51 nucleic acid sequence.

SEQ ID NO: 2 is an exemplary *Chlamydia trachomatis* tmRNA nucleic acid sequence.

SEQ ID NO: 3 is an exemplary *Escherichia coli* uidA nucleic acid sequence.

SEQ ID NO: 4 is an exemplary *Klebsiella pneumoniae* nifA nucleic acid sequence.

SEQ ID NO: 5 is an exemplary *Moraxella catarrhalis* purH nucleic acid sequence.

SEQ ID NO: 6 is an exemplary *Pneumocystis jirovecii* dhps nucleic acid sequence.

SEQ ID NO: 7 is an exemplary *Pseudomonas aeruginosa* gyrB nucleic acid sequence.

SEQ ID NO: 8 is an exemplary *Staphylococcus aureus* gsf nucleic acid sequence.

SEQ ID NO: 9 is an exemplary *Toxoplasma gondii* ssrRNA nucleic acid sequence.

SEQ ID NO: 10 is an exemplary *Ureaplasma parvum* ure nucleic acid sequence.

SEQ ID NO: 11 is an exemplary *Ureaplasma urealyticum* mba nucleic acid sequence.

SEQ ID NOs: 12-14 are exemplary *Acinetobacter baumannii* oxa-51 primer and probe nucleic acid sequences.

SEQ ID NOs: 15-17 are exemplary *Pseudomonas aeruginosa* gyrB primer and probe nucleic acid sequences.

SEQ ID NOs: 18-20 are exemplary *Klebsiella pneumoniae* nifA primer and probe nucleic acid sequences.

SEQ ID NOs: 21-23 are exemplary *Toxoplasma gondii* ssrRNA primer and probe nucleic acid sequences.

SEQ ID NOs: 24-26 are exemplary *Moraxella catarrhalis* purH primer and probe nucleic acid sequences.

SEQ ID NOs: 27-29 are exemplary *Escherichia coli/Shigella* spp. primer and probe nucleic acid sequences.

SEQ ID NOs: 30-32 are exemplary *Staphylococcus aureus* gsf primer and probe nucleic acid sequences.

SEQ ID NOs: 33-35 are exemplary *Pneumocystis jirovecii* dhps primer and probe nucleic acid sequences.

SEQ ID NOs: 36-38 are exemplary *Chlamydia trachomatis* tmRNA primer and probe nucleic acid sequences.

SEQ ID NOs: 39-41 are exemplary *Ureaplasma urealyticum* mba primer and probe nucleic acid sequences.

SEQ ID NOs: 42-44 are exemplary *Ureaplasma parvum* ure primer and probe nucleic acid sequences.

SEQ ID NOs: 45-47 are exemplary *Ureaplasma* spp. ure primer and probe nucleic acid sequences.

SEQ ID NOs: 48-51 are exemplary *Bartonella* spp. ssrA primer and probe nucleic acid sequences.

SEQ ID NO: 52 is an exemplary *Bartonella* ssrA nucleic acid sequence.

SEQ ID NO: 53 is an exemplary Group B *Streptococcus* cfb nucleic acid sequence.

SEQ ID NOs: 54-56 are exemplary Group *Streptococcus* cfb primer and probe nucleic acid sequences.

SEQ ID NO: 57 is an exemplary *Klebsiella pneumoniae* diguanylate cyclase nucleic acid sequence.

SEQ ID NOs: 58-60 are exemplary *Klebsiella pneumoniae* diguanylate cyclase primer and probe nucleic acid sequences.

SEQ ID NO: 61 is an exemplary *Neisseria meningitidis* sodC nucleic acid sequence.

SEQ ID NOs: 62-64 are exemplary *Neisseria meningitidis* sodC primer and probe nucleic acid sequences.

SEQ ID NOs: 65-67 are exemplary *Salmonella* spp. ttrRsBCA primer and probe nucleic acid sequences.

DETAILED DESCRIPTION

I. Abbreviations
 BAL: bronchoalveolar lavage
 GBS: Group B *Streptococcus*
 NP: nasopharyngeal
 NTC: no template control
 OP: oropharyngeal
 TAC: TAQMAN array card
 TNA: total nucleic acids
 UTM: universal transport medium
II. Terms Unless otherwise noted, technical terms are used according to conventional usage. Definitions of common terms in molecular biology may be found in Benjamin Lewin, *Genes V,* published by Oxford University Press, 1994 (ISBN 0-19-854287-9); Kendrew et al. (eds.), *The Encyclopedia of Molecular Biology,* published by Blackwell Science Ltd., 1994 (ISBN 0-632-02182-9); and Robert A. Meyers (ed.), *Molecular Biology and Biotechnology: a Comprehensive Desk Reference,* published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. As used herein, "comprises" means "includes." Thus, "comprising A or B," means "including A, B, or A and B," without excluding additional elements. It is further to be understood that all base sizes or amino acid sizes, and all molecular weight or molecular mass values, given for nucleic acids or polypeptides are approximate, and are provided for description. All publications, patent applications, patents, and other references mentioned herein are incorporated by reference in their entirety for all purposes.

Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

*Acinetobacter baumannii:* An aerobic gram-negative bacterium which can cause pneumonia, urinary tract infection, and necrotizing fasciitis. Many strains of *A. baumannii* are antibiotic resistant and it is an increasingly common nosocomial infection, for example, in intensive care units (such as neonatal intensive care units). *A. baumannii* can also colonize solutions (such as irrigating or intravenous solutions). Nucleic acid and protein sequences for *A. baumannii* are publicly available. For example, GenBank Accession Nos. NC_011586, NC_011595, NC_010611, NC_009085, and NC_010410 provide exemplary *A. baumannii* genome sequences, all of which are incorporated by reference as provided by GenBank on Apr. 30, 2012.

The *A. baumannii* oxa-51 gene encodes a beta-lactamase. Exemplary *A. baumannii* oxa-51 nucleic acid sequences include GenBank Accession Nos. AJ309734 and DQ385606, both of which are incorporated by reference as present in GenBank on Apr. 30, 2012. An exemplary *Acinetobacter baumannii* nucleotide sequence of oxa-51 is found at GenBank Accession No. AJ309734 (SEQ ID NO: 1).

*Bartonella* spp.: A genus of gram-negative bacteria that infect a wide variety of mammalian hosts, including humans. *Bartonella* are transmitted by blood-sucking insects (for example, ticks, fleas, and lice). High prevalence of *Bartonella* bacteremia has been reported in populations of rodents, cats, and ruminants worldwide. There are at least 30 known species and subspecies of *Bartonella*. Nucleic acid and protein sequences for *Bartonella* spp. are publicly available. For example, GenBank Accession Nos. NC_005955 (*B. quintana*), NC_005956 (*B. henselae*), NC_010161 (*B. tribocorum*), NC_012846 (*B. grahamii*), and NC_008783 (*B. bacilliformis*) provide exemplary *Bartonella* genome sequences, all of which are incorporated by reference as provided by GenBank on Apr. 30, 2012. One of ordinary skill in the art can identify additional *Bartonella* spp., for example utilizing the NCBI Taxonomy Browser (e.g., www.ncbi.nlm.nih.gov/Taxonomy/).

The *Bartonella* ssrA RNA (also known as transfer-messenger RNA; tmRNA) is a single-copy prokaryotic-specific molecule involved in processing of incomplete peptides and resolution of stalled ribosomes during translation. Exemplary *Bartonella* ssrA nucleic acid sequences include GenBank Accession Nos. JN029766, BX897700 (1020848 . . . 1021176), JN029785, BX87699 (1215947 . . . 1216279), JN029796, AM260525 (1675346 . . . 1675682), JN029795, NC_012846.1 (1542284 . . . 1542620), JN029794, and NC_008783.1 (955069 . . . 955373), all of which are incorporated herein by reference as provided by GenBank on Apr. 30, 2012. An exemplary *Bartonella* nucleotide sequence of ssrA is found at GenBank Accession No. NC_005955 (1020727-1021342) (SEQ ID NO: 52).

*Chlamydia trachomatis:* A gram-negative bacterium that is a common sexually transmitted disease. *C. trachomatis* can also be transmitted from an infected mother, resulting in a potentially life-threatening respiratory infection in neonates. Nucleic acid and protein sequences for *C. trachomatis* are publicly available. For example, GenBank Accession Nos. NC_012687, NC_000117, NC_007429, NC_010280, and NC_015744 provide exemplary *C. trachomatis* genome sequences, all of which are incorporated by reference as provided by GenBank on Apr. 30, 2012.

The *C. trachomatis* tmRNA is an RNA with both tRNA and mRNA characteristics. Exemplary *C. trachomatis* tmRNA nucleic acid sequences include GenBank Accession Nos. NC_000117 (20663-21082) and NC_007429 (21258-21677; complement), both of which are incorporated herein by reference as present in GenBank on Apr. 30, 2012. An exemplary *Chlamydia trachomatis* nucleotide sequence of tmRNA is found at GenBank Accession No. NC_000117 (20663-21082) (SEQ ID NO: 2).

*Escherichia coli:* A Gram-negative, rod-shaped bacterium that is commonly found in the lower intestine of warm-blooded organisms, where it (and related bacteria) constitute about 0.1% of gut flora. Most *E. coli* strains are harmless, but some serotypes (for example O157:H7 and O104:H4) can cause serious disease in humans. Pathogenic *E. coli* is frequently contracted via contaminated food or water. The harmless strains are part of the normal flora of the gut, and can benefit their hosts by producing vitamin $K_2$ and by preventing the establishment of pathogenic bacteria within the intestine.

Nucleic acid and protein sequences for *E. coli* are publicly available. For example, GenBank Accession Nos. NC_011751, NC_011742, NC_011415, NC_011601, and NC_011353 provide exemplary *E. coli* genome sequences, all of which are incorporated by reference as provided by GenBank on Apr. 30, 2012.

The *E. coli* uidA gene encodes a β-D-glucuronidase. Exemplary *E. coli* uidA nucleic acid sequences include GenBank Accession Nos. NC_011601 (1769353-1771164, complement), NC_000913 (1692284-1694095), and NC_011751 (192037-1930848, complement), all of which are incorporated herein by reference as present in GenBank on Apr. 30, 2012. An exemplary *E. coli* nucleotide sequence of uidA is found at GenBank Accession No. NC_000913 (1692284-1694095) (SEQ ID NO: 3).

Fluorophore: A chemical compound, which when excited by exposure to a particular stimulus, such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the probes and primers disclosed herein are known to those of ordinary skill in the art and include those provided in U.S. Pat. No. 5,866,366 to Nazarenko et al., such as 4-acetamido- 4'-isothiocyanatostilbene-2,2'disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcoulaurin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), 6-carboxy-fluorescein (HEX), and TET (tetramethyl fluorescein); fluorescamine; IR144; IR1446; Malachite Green isothiocyanate; 4-methylumbelliferone; ortho-cresolphthalein; nitrotyrosine; pararosaniline; Phenol Red; B-phycoerythrin; o-phthaldialdehyde; pyrene and derivatives such as pyrene, pyrene butyrate, and succinimidyl 1-pyrene butyrate; Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; LightCycler Red 640; Cy5.5; and Cy56-carboxyfluorescein; boron dipyrromethene difluoride (BODIPY); acridine; stilbene; Cy3; Cy5, VIC® (Applied Biosystems); LC Red 640; LC Red 705; and Yakima yellow amongst others. Additional examples of fluorophores include Quasar® 670, Quasar® 570, CAL Fluor® Red 590, CAL Fluor® Red 610, CAL Fluor® 615, CAL Fluor® Red 635, CAL Fluor® Green 520, CAL Fluor® Gold 540, and CAL Fluor® Orange 560 (Biosearch Technologies, Novato, CA).

Other suitable fluorophores include those known to those of ordinary skill in the art, for example those available from Molecular Probes/Life Technologies (Carlsbad, CA). In particular examples, a fluorophore is used as a donor fluorophore or as an acceptor fluorophore.

"Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum that overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as Dabcyl, QSY7 (Molecular Probes), QSY33 (Molecular Probes), BLACK HOLE QUENCHERS™ (Biosearch Technologies; such as BHQO, BHQ1, BHQ2, and BHQ3), ECLIPSE™ Dark Quencher (Epoch Biosciences), or IOWA BLACK™ (Integrated DNA Technologies). A quencher can reduce or quench the emission of a donor fluorophore. In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore).

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, NY (chapters 9 and 11). The following is an exemplary set of hybridization conditions and is not limiting:

Very High Stringency (detects sequences that share at least 90% identity)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (detects sequences that share at least 80% identity)
  Hybridization: 5x-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (detects sequences that share at least 60% identity)
  Hybridization: 6×SSC at RT to 55° C. for 16-20 hours
  Wash at least twice: 2x-3×SSC at RT to 55° C. for 20-30 minutes each.

*Klebsiella pneumoniae:* A gram-negative facultative anaerobic bacterium commonly found in the normal flora of the mouth, skin, and intestine. *K. pneumoniae* can cause respiratory disease, typically as a result of a colonized subject aspirating oropharyngeal bacteria into the lower respiratory tract. It is one of the most common causes of neonatal sepsis, especially in developing countries. Many strains of *K. pneumoniae* are antibiotic resistant and it is an increasingly common nosocomial infection. Nucleic acid and protein sequences for *K. pneumoniae* are publicly available. For example, GenBank Accession Nos. CP000964, NC_011283, NC_009648, and NC_012731 provide exemplary *K. pneumoniae* genome sequences, all of which are incorporated by reference as provided by GenBank on Apr. 30, 2012.

The *K. pneumoniae* nifA gene encodes a transcriptional activator involved in the regulation of expression of the nif genes. An exemplary *K. pneumoniae* nifA nucleic acid sequence includes GenBank Accession No. CP000964 (1752865-1754439), which is incorporated herein by reference as present in GenBank on Apr. 30, 2012. An exemplary *Klebsiella pneumoniae* nucleotide sequence of nifA is found at GenBank Accession No. CP000964 (1752865-1754439) (SEQ ID NO: 4).

The *K. pneumoniae* diguanylate cyclase gene encodes an enzyme which catalyzes the formation of cyclic di-GMP from GTP. An exemplary *K. pneumoniae* diguanylate cyclase nucleic acid sequence includes GenBank Accession No. CP000964 (1413543-1415714), which is incorporated herein by reference as present in GenBank on Feb. 15, 2013. An exemplary *Klebsiella pneumoniae* nucleotide sequence of diguanylate cyclase is found at GenBank Accession No. CP000964 (1413543-1415714) (SEQ ID NO: 57).

*Moraxella catarrhalis:* A gram-negative bacterium (previously known as *Branhamella catarrhalis*) which can cause otitis media, respiratory infections, endocarditis, and meningitis, particularly in newborns and young children. Nucleic acid and protein sequences for *K. pneumoniae* are publicly available. For example, GenBank Accession No. NC_014147 provides an exemplary *M. catarrhalis* genome sequence, which is incorporated by reference as provided by GenBank on Apr. 30, 2012.

The *M. catarrhalis* purH gene encodes a bifunctional phosphoribosylaminoimidazolecarboxamide formyltransferase/IMP cyclohydrolase. An exemplary *M. catarrhalis* purH nucleic acid sequence includes GenBank Accession No. NC_014147 (620865-622463), which is incorporated herein by reference as present in GenBank on Apr. 30, 2012. An exemplary *Moraxella catarrhalis* nucleotide sequence of purH is found at GenBank Accession No. NC_014147 (620865-622463) (SEQ ID NO: 5).

*Neisseria meningitidis:* A gram-negative bacterium that is a leading cause of septicemia and life-threatening meningitis in children. There are at least five serogroups based on capsular polysaccharides (A, B, C, Y, and W135) Nucleic acid and protein sequences for *N. meningitidis* are publicly available. For example, GenBank Accession Nos. CP_002419-CP_002424 provide exemplary *N. meningitidis* genome sequences, all of which are incorporated by reference as provided by GenBank on Feb. 15, 2013.

The *Neisseria meningitidis* sodC gene encodes a Cu,Zn superoxide dismutase. Exemplary *Neisseria meningitidis* sodC nucleic acid sequences include GenBank Accession Nos. CP_002423 (862943-493503) and CP_002422 (1411887-1412447), both of which are incorporated by reference herein as provided by GenBank on Feb. 15, 2013. An exemplary *N. meningitidis* sodC nucleotide sequence is found at GenBank Accession No. CP_002423 (862943-493503) (SEQ ID NO: 61).

*Pneumocystis jirovecii:* Formerly classified as *Pneumocystis carinii*. A nonfilamentous fungus that can cause severe pneumonia in immunocompromised patients and neonates. *P. jirovecii* may also colonize the lungs of healthy individuals without causing disease. Nucleic acid and protein sequences for *P. jirovecii* are publicly available.

The *P. jirovecii* dhps gene encodes a diydropteroate synthase. An exemplary *P. jirovecii* dhps nucleic acid sequence includes GenBank Accession No. AF139132, which is incorporated herein by reference as present in GenBank on Apr. 30, 2012. An exemplary *Pneumocystis jirovecii* nucleotide sequence of dhps is found at GenBank Accession No. AF139132 (SEQ ID NO: 6).

*Pseudomonas aeruginosa:* A gram-negative bacterium that is a leading cause of hospital-acquired infections, including bacteremia, burn/wound infections, and severe pneumonia, including in neonatal intensive care units. This organism is also a common cause of community-acquired skin, ear, and eye infections, often associated with swimming in contaminated recreational facilities. Nucleic acid and protein sequences for *P. aeruginosa* are publicly available. For example, GenBank Accession Nos. NC_011770, NC_009656, NC_002516, and NC_008463 provide exemplary *P. aeruginosa* genome sequences, all of which are incorporated by reference as provided by GenBank on Apr. 30, 2012.

The *P. aeruginosa* gyrb gene encodes a dna gyrase subunit B. Exemplary *P. aeruginosa* gyrb nucleic acid sequences include GenBank Accession Nos. AB005881, NC_002516 (4275-6695), NC_009656 (4274-6694), and NC_008463 (4275-6695), which are incorporated herein by reference as present in GenBank on Apr. 30, 2012. An exemplary *Pseudomonas aeruginosa* nucleotide sequence of gyrb is found at GenBank Accession No. AB005881 (SEQ ID NO: 7).

*Shigella:* A genus of Gram-negative, nonspore forming, non-motile, rod-shaped bacteria closely related to *Escherichia coli* and *Salmonella*. The causative agent of human shigellosis, *Shigella* causes disease in primates, but not in other mammals. It can cause infection in neonates as a result of maternal transmission during delivery. During infection, it typically causes dysentery. Phylogenetic studies indicate that *Shigella* may be more appropriately treated as subgenus of *Escherichia*.

*Staphylococcus aureus:* A gram-positive bacterium which can cause diseases including skin infection, respiratory infection, meningitis, endocarditis, toxic shock syndrome, and sepsis. It is one of the most common nosocomial infections and is increasing in frequency in neonatal intensive care units. Multi-drug resistant strains (including methicillin-resistant *S. aureus;* MRSA) are increasingly common. Nucleic acid and protein sequences for *S. aureus* are publicly available. For example, GenBank Accession Nos. NC_007622, NC_002951, NC_013450, and NC_009632 provide exemplary *S. aureus* genome sequences, all of which are incorporated by reference as provided by GenBank on Apr. 30, 2012.

The *S. aureus* gsf gene encodes a conserved region in glutamate synthase family protein. An exemplary *S. aureus* gsf nucleic acid sequence includes GenBank Accession No. CP003194 (2567647-2569224), which is incorporated by reference as provided by GenBank on Apr. 30, 2012. An exemplary *Staphylococcus aureus* nucleotide sequence of gsf is found at GenBank Accession No. CP003194 (2567647-2569224) (SEQ ID NO: 8). *Streptococcus agalactiae* (Group B *Streptococcus;* GBS): A gram-positive bacterium that is a major cause of meningitis and sepsis in neonates. GBS can also asymptomatically colonize skin and mucous membranes. Nucleic acid and protein sequences for GBS are publicly available. For example, GenBank Accession Nos. NC_007432, NC_004166, and NC_019048 provide exemplary GBS genome sequences, all of which are incorporated by reference as provided by GenBank on Feb. 15, 2013.

The GBS cfb gene encodes the CAMP factor. Exemplary GBS cfb nucleic acid sequences include GenBank Accession Nos. NC_004116 (2016473-2017240), NC_007432 (1969227-1969994), and NC_019048 (1695124-1695891), all of which are incorporated by reference herein as provided by GenBank on Feb. 15, 2013. An exemplary GBS nucleotide sequence of cfb is found at GenBank Accession No. NC_004116 (2016473-2017240) (SEQ ID NO: 53).

*Toxoplasma gondii:* A parasite of many animal species. Cats are the only host capable of passing infective *T. gondii* oocysts to subsequent hosts. Humans may become infected by exposure to contaminated undercooked meat or exposure to water, soil, or other material contaminated with *T. gondii* laden feline feces. Infection may be asymptomatic or elicit mild symptoms; however serious neurologic or ocular disease may result in the fetus of an exposed pregnant women. Nucleic acid and protein sequences for *T. gondii* are publicly available. For example, GenBank Accession No. NZ_ABPA00000000 provides an exemplary *T. gondii* genome sequence, which is incorporated by reference as provided by GenBank on Apr. 30, 2012.

The *T. gondii* ssrRNA gene is a small subunit ribosomal RNA. An exemplary *T. gondii* ssrRNA nucleic acid sequence includes GenBank Accession No. EF472967, which is incorporated herein by reference as present in GenBank on Apr. 30, 2012. An exemplary *Toxoplasma gondii* nucleotide sequence of ssrRNA is found at GenBank Accession No. EF472967 (SEQ ID NO: 9).

*Ureaplasma parvum:* Previously classified as *Ureaplasma urealyticum* biovar 1. A mycoplasma which can cause genito-urinary infection and infertility. It can also cause respiratory infection in neonates as a result of maternal transmission during delivery. Nucleic acid and protein sequences for *U. parvum* are publicly available. For example, GenBank Accession Nos. NC_010503 and NC_002162 provide exemplary *U. parvum* genome sequences, both of which are incorporated by reference as provided by GenBank on Apr. 30, 2012.

The *U. parvum* ure gene encodes the urease complex. An exemplary *U. parvum* ure nucleic acid sequence includes GenBank Accession No. AF085733, which is incorporated by reference as provided by GenBank on Apr. 30, 2012. An exemplary *Ureaplasma parvum* nucleotide sequence of ureC is found at GenBank Accession No. AF085733 (912-2708) (SEQ ID NO: 10).

*Ureaplasma* spp.: A genus of gram-negative bacteria which is urease positive. *Ureaplasma* spp. refers to any species in the genus *Ureaplasma*. In some embodiments, *Ureaplasma* spp. includes *Ureaplasma parvum* and *Ureaplasma urealyticum*. One of ordinary skill in the art can identify additional *Ureaplasma* spp. (such as *U. canigenitalium, U. cati, U. diversum, U. felinum, U. gallorale,* and *U. loridis*), for example utilizing the NCBI Taxonomy Browser (e.g., www.ncbi.nlm.nih.gov/Taxonomy/).

*Ureaplasma urealyticum:* A mycoplasma which can cause genito-urinary infection, infertility, and meningitis. It can also cause respiratory disease in neonates as a result of maternal transmission during delivery. Nucleic acid and protein sequences for *U. urealyticum* are publicly available. For example, GenBank Accession No. NC_011374 provides an exemplary *U. urealyticum* genome sequence, which is incorporated by reference as provided by GenBank on Apr. 30, 2012.

The *U. urealyticum* mba gene encodes the multiple banded antigen. An exemplary *U. urealyticum* mba nucleic acid sequence includes GenBank Accession No. AF055367, which is incorporated by reference as provided by GenBank on Apr. 30, 2012. An exemplary *Ureaplasma urealyticum* nucleotide sequence of mba is found at GenBank Accession No. AF055367 (SEQ ID NO: 11).

III. Methods for Detection of Pathogens

Methods for detecting the presence of a pathogen such as *Acinetobacter baumannii, Pseudomonas aeruginosa, Klebsiella pneumooniae, Toxoplasma gondii, Moraxella catarrhalis, Escherichia coli, Shigella, Staphylococcus aureus, Pneumocystis jirovecii, Chlamydia trachomatis, Ureaplasma urealyticum, Ureaplasma parvum, Ureaplasma* spp., *Bartonella* spp. *Streptococcus agalactiae,* and/or *Neisseria meningitidis* in a sample are disclosed, for example, utilizing the probes and/or primers disclosed herein. In some embodiments, the methods include detection of a single selected pathogen. In other embodiments, the methods include detection of one or more of *Acinetobacter baumannii, Pseudomonas aeruginosa, Klebsiella pneumoniae, Toxoplasma gondii, Moraxella catarrhalis, Escherichia coli, Shigella, Staphylococcus aureus, Pneumocystis jirovecii, Chlamydia trachomatis, Ureaplasma urealyticum, Ureaplasma parvum, Ureaplasma* spp., *Bartonella* spp., *Streptococcus agalactiae, Neisseria meningitidis* or any combination of two or more thereof (for example, utilizing a simultaneous multipathogen detection assay (such as an array or card assay) or a multiplex assay).

The methods described herein may be used for any purpose for which detection of *Acinetobacter baumannii, Pseudomonas aeruginosa, Klebsiella pneumoniae, Toxoplasma gondii, Moraxella catarrhalis, Escherichia coli, Shigella, Staphylococcus aureus, Pneumocystis jirovecii, Chlamydia trachomatis, Ureaplasma urealyticum, Ureaplasma parvum, Ureaplasma* spp., *Bartonella* spp., *Streptococcus agalactiae,* and/or *Neisseria meningitidis* is desirable, including diagnostic or prognostic applications, such as in laboratory or clinical settings.

Appropriate samples include any conventional environmental or biological samples, including clinical samples obtained from a human or veterinary subject. Suitable samples include all biological samples useful for detection of infection in subjects, including, but not limited to, cells, tissues (for example, lung, liver, or kidney), autopsy samples, bone marrow aspirates, bodily fluids (for example, blood, serum, urine, cerebrospinal fluid, middle ear fluids, bronchoalveolar lavage, tracheal aspirates, sputum, nasopharyngeal swabs or aspirates, oropharyngeal swabs or aspirates, or saliva), eye swabs, cervical swabs, vaginal swabs, rectal swabs, stool, and stool suspensions. Suitable samples also include all samples useful for detection of a pathogen in an environment (such as a clinic or hospital), including but not limited to a water or fluid sample, a food sample, or a surface swab (for example, a swab of a counter, bed, floor, wall, or other surface). Standard techniques for acquisition of such samples are available. See for example, Schluger et al., *J. Exp. Med.* 176:1327-1333, 1992; Bigby et al., *Am. Rev. Respir. Dis.* 133:515-518, 1986; Kovacs et al., *N. Engl. J. Med.* 318:589-593, 1988; and Ognibene et al., *Am. Rev. Respir. Dis.* 129:929-932, 1984.

In some embodiments, the nucleic acids detected using the methods provided herein include nucleic acid molecules from *Acinetobacter baumannii, Pseudomonas aeruginosa, Klebsiella pneumooniae, Toxoplasma gondii, Moraxella catarrhalis, Escherichia coli, Shigella, Staphylococcus aureus, Pneumocystis jirovecii, Chlamydia trachomatis,*

*Ureaplasma urealyticum, Ureaplasma parvum, Ureaplasma* spp., *Bartonella* spp., *Streptococcus agalactiae,* or *Neisseria meningitidis.* In at least some embodiments, the disclosed methods can detect multiple strains or serotypes of a pathogen species. In some examples, the nucleic acids detected include nucleic acids from multidrug-resistant strains of *Acinetobacter baumannii, Pseudomonas aeruginosa, Klebsiella pneumooniae, Toxoplasma gondii, Moraxella catarrhalis, Escherichia coli, Shigella, Staphylococcus aureus, Pneumocystis jirovecii, Chlamydia trachomatis, Ureaplasma urealyticum, Ureaplasma parvum, Ureaplasma* spp., *Bartonella* spp., *Streptococcus agalactiae,* and/or *Neisseria meningitidis.* Strains of particular pathogens may be obtained from patient or environmental samples or laboratory or reference collections, for example, the American Type Culture Collection (Manassas, VA). In one non-limiting example, the disclosed methods detect nucleic acids from methicillin-resistant *S. aureus* (MRSA), including hospital-acquired MRSA (HA-MRSA) or community-acquired MRSA (CA-MRSA). In other non-limiting examples, the disclosed methods detect nucleic acids from *E. coli* virotypes including enterotoxigenic *E. coli* (ETEC), enteroinvasive *E. coli* (EIEC), enterohemorrhagic *E. coli* (EHEC), enteropathogenic *E. coli* (EPEC), or enteroaggregative *E. coli* (EAEC).

One of ordinary skill in the art will know suitable methods for extracting nucleic acids such as RNA and/or DNA from a sample; such methods will depend upon, for example, the type of sample in which the pathogen nucleic acid is found. Nucleic acids can be extracted using standard methods. For instance, rapid nucleic acid preparation can be performed using a commercially available kit (such as kits and/or instruments from Qiagen (such as DNEASY® or RNEASY® kits), Roche Applied Science (such as MAGNA PURE® kits and instruments), Thermo Scientific (KingFisher mL), bioMérieux (NUCLISENS® NASBA Diagnostics), or Epicentre (MASTERPURE™ kits)). In other examples, the nucleic acids may be extracted using guanidinium isothiocyanate, such as single-step isolation by acid guanidinium isothiocyanate-phenol-chloroform extraction (Chomczynski et al. *Anal. Biochem.* 162:156-159, 1987). The sample can be used directly or can be processed, such as by adding solvents, preservatives, buffers, or other compounds or substances.

Detecting presence of at least one of an *Acinetobacter baumannii, Pseudomonas aeruginosa, Klebsiella pneumooniae, Toxoplasma gondii, Moraxella catarrhalis, Escherichia coli, Shigella, Staphylococcus aureus, Pneumocystis jirovecii, Chlamydia trachomatis, Ureaplasma urealyticum, Ureaplasma parvum, Ureaplasma* spp., *Bartonella* spp., *Streptococcus agalactiae,* or *Neisseria meningitidis* nucleic acid in a sample involves contacting the sample with at least one of the probes (such as 1, 2, 3, 4, 5, 6, 7, 8, 9, 10, 11, 12, 13, 14, or 15 probes) disclosed herein that is capable of hybridizing to an *Acinetobacter baumannii* oxa-51 nucleic acid, a *Pseudomonas aeruginosa* gyrB nucleic acid, a *Klebsiella pneumoniae* nifA nucleic acid, a *Toxoplasma gondii* ssrRNA nucleic acid, a *Moraxella catarrhalis* purH nucleic acid, an *Escherichia coli* and/or *Shigella* uidA nucleic acid, a *Staphylococcus aureus* gsf nucleic acid, a *Pneumocystis jirovecii* dhps nucleic acid, a *Chlamydia trachomatis* tmRNA nucleic acid, a *Ureaplasma urealyticum* mba nucleic acid, a *Ureaplasma parvum* ure nucleic acid, a *Ureaplasma* spp. ure nucleic acid, a *Bartonella* spp. ssrA nucleic acid, a *Streptococcus agalactiae* cfb nucleic acid, or a *Neisseria meningitidis* sodC nucleic acid, for example, under conditions of high or very high stringency.

One of ordinary skill in the art can determine low, high, or very high stringency conditions for hybridization of a primer or probe (such as a probe or primer disclosed herein) to a nucleic acid sequence (for example to one of SEQ ID NOs: 1-11, 52, 53, 57, or 61). In some examples, the conditions are for hybridization of a primer or probe to a nucleic acid attached to a solid support (such as the conditions provided above). In other examples, the conditions are for hybridization of a primer or probe to a nucleic acid in solution, such as a PCR reaction mixture. In some non-limiting examples, low stringency conditions include hybridization (such as an annealing step in PCR) at a temperature of about 45-50° C. In other examples, high stringency conditions include hybridization (such as an annealing step in PCR) at a temperature of about 50-60° C. In further examples, very high stringency conditions include hybridization (such as an annealing step in PCR) at a temperature of greater than 60° C. One of skill in the art can determine appropriate hybridization or annealing conditions (including the degree of hybridization) based on the particular primers or probes and target nucleic acids to be amplified or detected.

In some embodiments, the methods include contacting the sample with at least one probe comprising a nucleic acid molecule between 10 and 40 nucleotides in length and detecting hybridization between the one or more probes and a nucleic acid in the sample, wherein detection of hybridization indicates the presence of one or more of said pathogens in the sample. In some examples, the probe is capable of hybridizing (such as under high stringency or very high stringency conditions) to an *Acinetobacter baumannii* nucleic acid sequence set forth as SEQ ID NO: 1, a *Chlamydia trachomatis* nucleic acid sequence set forth as SEQ ID NO: 2, an *Escherichia coli* nucleic acid sequence set forth as SEQ ID NO: 3, a *Klebsiella pneumoniae* nucleic acid sequence set forth as SEQ ID NO: 4 or SEQ ID NO: 57, a *Moraxella catarrhalis* nucleic acid sequence set forth as SEQ ID NO: 5, a *Pneumocystis jirovecii* nucleic acid sequence set forth as SEQ ID NO: 6, a *Pseudomonas aeruginosa* nucleic acid sequence set forth as SEQ ID NO: 7, a *Staphylococcus aureus* nucleic acid sequence set forth as SEQ ID NO: 8, a *Toxoplasma gondii* nucleic acid sequence set forth as SEQ ID NO: 9, a *Ureaplasma parvum* nucleic acid sequence set forth as SEQ ID NO: 10, a *Ureaplasma urealyticum* nucleic acid sequence set forth as SEQ ID NO: 11, a *Bartonella* spp. nucleic acid set forth as SEQ ID NO: 52, a *Streptococcus agalactiae* nucleic acid sequence set forth as SEQ ID NO: 53, a *Neisseria meningitidis* nucleic acid set forth as SEQ ID NO: 61, or a nucleic acid sequence at least 90% identical (for example 91%, 92%, 93%, 94%, 95%, 96%, 97%, 98%, 99%, or even 100% identical) to one of SEQ ID NOs: 1-11 52-53, 57, or 61. In some examples, the sample is contacted with one or more nucleic acid probes between 20 and 40 nucleotides in length comprising or consisting of a nucleic acid sequence set forth as any one of SEQ ID NOs: 14, 17, 20, 23, 26, 29, 32, 35, 38, 41, 44, 47, 50, 56, 60, 64, or the reverse complement thereof.

In particular examples, the probes are detectably labeled (for example, as described in section IV, below). In some examples, the probes are at least 10, 15, 20, 25, 30, 35, or 40 nucleotides in length. In other examples, the probes may be no more than 10, 15, 20, 25, 30, 35, or 40 nucleotides in length. In further examples, the probes are 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

Detection of hybridization between an *Acinetobacter baumannii* probe (for example SEQ ID NO: 14) and a nucleic acid indicates the presence of *Acinetobacter baumannii* nucleic acid in the sample, detection of hybridization between a *Chlamydia trachomatis* probe (for example SEQ ID NO: 38) and a nucleic acid indicates the presence of *Chlamydia trachomatis* nucleic acid in the sample, detection of hybridization between an *Escherichia coli/Shigella* probe (for example SEQ ID NO: 29) and a nucleic acid indicates the presence of *E. coli* and/or *Shigella* nucleic acid in the sample, detection of hybridization between a *Klebsiella pneumoniae* probe (for example SEQ ID NO: 20 or SEQ ID NO: 60) and a nucleic acid indicates the presence of *Klebsiella pneumoniae* nucleic acid in the sample, detection of hybridization between a *Moraxella catarrhalis* probe (for example SEQ ID NO: 26) and a nucleic acid indicates the presence of *Moraxella catarrhalis* nucleic acid in the sample, detection of hybridization between a *Pneumocystis jirovecii* probe (for example SEQ ID NO: 35) and a nucleic acid indicates the presence of *Pneumocystis jirovecii* nucleic acid in the sample, detection of hybridization between a *Pseudomonas aeruginosa* probe (for example SEQ ID NO: 17) and a nucleic acid indicates the presence of *Pseudomonas aeruginosa* nucleic acid in the sample, detection of hybridization between a *Staphylococcus aureus* probe (for example SEQ ID NO: 32) and a nucleic acid indicates the presence of *Staphylococcus aureus* nucleic acid in the sample, detection of hybridization between a *Toxoplasma gondii* probe (for example SEQ ID NO: 23) and a nucleic acid indicates the presence of *Toxoplasma gondii* nucleic acid in the sample, detection of hybridization between a *Ureaplasma parvum* probe (for example SEQ ID NO: 44) and a nucleic acid indicates the presence of *Ureaplasma parvum* nucleic acid in the sample, detection of hybridization between a *Ureaplasma urealyticum* probe (for example SEQ ID NO: 41) and a nucleic acid indicates the presence of *Ureaplasma urealyticum* nucleic acid in the sample, detection of hybridization between a *Ureaplasma* spp. probe (for example SEQ ID NO: 47) and a nucleic acid indicates the presence of *Ureaplasma* spp. nucleic acid in the sample, detection of hybridization between a *Bartonella* spp. probe (for example SEQ ID NO: 50) and a nucleic acid indicates the presence of *Bartonella* spp. nucleic acid in the sample, detection of hybridization between a *Streptococcus agalactiae* probe (for example SEQ ID NO: 56) and a nucleic acid indicates the presence of *Streptococcus agalactiae* nucleic acid in the sample, and detection of hybridization between a *Neisseria meningitidis* probe (for example SEQ ID NO: 64) and a nucleic acid indicates the presence of a *Neisseria meningitidis* nucleic acid in the sample.

In some embodiments, the methods disclosed herein further include positive and/or negative controls. One of ordinary skill in the art can select suitable controls. In some examples, a negative control is a no template control (such as a reaction that includes all components except the nucleic acid sample). In other examples, a positive control includes a sample known to include nucleic acid from a particular pathogen. In further examples, a positive control includes an internal positive control, such as a human nucleic acid (for example, RNase P) when the sample is from a human subject. In other examples, a positive control includes a synthetic positive control (such as a combined positive control), for example, a nucleic acid molecule including forward primer, probe, and reverse primer sequences for one or more primer/probe sets included in the assay. A combined positive control may also include additional positive or negative controls, such as a human nucleic acid control (for example, RNase P), and/or a control for laboratory contamination (such as a primer/probe that is not included in the assay). See, e.g., Kodani and Winchell (*J. Clin. Microbiol.* 50:1057-1060, 2011; incorporated herein by reference) for exemplary methods for constructing a combined positive control.

In some embodiments, nucleic acids present in a sample (for example, one or more of *Acinetobacter baumannii*, *Pseudomonas aeruginosa*, *Klebsiella pneumoniae*, *Toxoplasma gondii*, *Moraxella catarrhalis*, *Escherichia coli*, *Shigella*, *Staphylococcus aureus*, *Pneumocystis jirovecii*, *Chlamydia trachomatis*, *Ureaplasma urealyticum*, *Ureaplasma parvum*, *Ureaplasma* spp., *Bartonella* spp., *Streptococcus agalactiae*, or *Neisseria meningitidis* nucleic acids) are amplified prior to using a probe for detection. For instance, it can be advantageous to amplify a portion of one of more of the disclosed nucleic acids, and then detect the presence of the amplified nucleic acid, for example, to increase the number of nucleic acids that can be detected, thereby increasing the signal obtained. Specific nucleic acid primers can be used to amplify a region that is at least about 50, at least about 60, at least about 70, at least about 80 at least about 90, at least about 100, at least about 200, at least about 250, at least about 300, at least about 400, at least about 500, at least about 1000, at least about 2000, or more base pairs in length to produce amplified nucleic acids (such as amplified *Acinetobacter baumannii*, *Pseudomonas aeruginosa*, *Klebsiella pneumoniae*, *Toxoplasma gondii*, *Moraxella catarrhalis*, *Escherichia coli*, *Shigella*, *Staphylococcus aureus*, *Pneumocystis jirovecii*, *Chlamydia trachomatis*, *Ureaplasma urealyticum*, *Ureaplasma parvum*, *Ureaplasma* spp., *Bartonella* spp., *Streptococcus agalactiae*, or *Neisseria meningitidis* nucleic acids). In other examples, specific nucleic acid primers can be used to amplify a region that is about 50-3000 base pairs in length (for example, about 70-2000 base pairs, about 100-1000 base pairs, about 50-300 base pairs, about 300-500 base pairs, or about 1000-3000 base pairs in length).

Detecting the amplified product typically includes the use of labeled probes that are sufficiently complementary to, and hybridize to, the amplified nucleic acid sequence. Thus, the presence, amount, and/or identity of the amplified product can be detected by hybridizing a labeled probe, such as a fluorescently labeled probe, complementary to the amplified product. In one embodiment, the detection of a target nucleic acid sequence of interest, such as an *Acinetobacter baumannii* oxa-51 nucleic acid, a *Pseudomonas aeruginosa* gyrB nucleic acid, a *Klebsiella pneumoniae* nifA nucleic acid, a *Klebsiella pneumoniae* diguanylate cyclase nucleic acid, a *Toxoplasma gondii* ssrRNA nucleic acid, a *Moraxella catarrhalis* purH nucleic acid, an *Escherichia coli* and/or *Shigella* uidA nucleic acid, a *Staphylococcus aureus* gsf nucleic acid, a *Pneumocystis jirovecii* dhps nucleic acid, a *Chlamydia trachomatis* tmRNA nucleic acid, a *Ureaplasma urealyticum* mba nucleic acid, a *Ureaplasma parvum* ure nucleic acid, a *Ureaplasma* spp. ure nucleic acid, a *Bartonella* spp. ssrA nucleic acid, a *Streptococcus agalactiae* cfb nucleic acid, or a *Neisseria meningitidis* sodC nucleic acid includes the combined use of PCR amplification and a labeled probe such that the product is measured using real-time PCR (such as TAQMAN® real-time PCR). In another embodiment, the detection of an amplified target nucleic acid sequence of interest includes the transfer of the amplified target nucleic acid to a solid support, such as a blot, for example a Northern blot, and probing the blot with a probe, for example a labeled probe, that is complementary to the amplified target nucleic acid. In still further embodiments, the detection of amplified target nucleic acid of interest includes the hybridization of a labeled amplified target nucleic acid to probes disclosed herein that are arrayed in a predetermined array with an addressable location and that are complementary to the amplified target nucleic acid.

Any nucleic acid amplification method can be used to detect the presence of one or more of *Acinetobacter baumannii, Pseudomonas aeruginosa, Klebsiella pneumoniae, Toxoplasma gondii, Moraxella catarrhalis, Escherichia coli, Shigella, Staphylococcus aureus, Pneumocystis jirovecii, Chlamydia trachomatis, Ureaplasma urealyticum, Ureaplasma parvum, Ureaplasma* spp., *Bartonella* spp., *Streptococcus agalactiae,* or *Neisseria meningitidis* nucleic acids in a sample. In one specific, non-limiting example, polymerase chain reaction (PCR) is used to amplify the pathogen-specific nucleic acid sequences. In other specific, non-limiting examples, real-time PCR, reverse transcriptase-polymerase chain reaction (RT-PCR), real-time reverse transcriptase-polymerase chain reaction (rt RT-PCR), ligase chain reaction, or transcription-mediated amplification (TMA) is used to amplify the nucleic acids. In a specific example, one or more (such as 1, 2, 3, 4, 5, 6, 7, 8, 9, 10, 11, 12, 13, 14, or 15) of an *Acinetobacter baumannii* oxa-51 nucleic acid, a *Pseudomonas aeruginosa* gyrB nucleic acid, a *Klebsiella pneumoniae* nifA nucleic acid, a *Klebsiella pneumoniae* diguanylate cyclase nucleic acid, a *Toxoplasma gondii* ssrRNA nucleic acid, a *Moraxella catarrhalis* purH nucleic acid, an *Escherichia coli/Shigella* uidA nucleic acid, a *Staphylococcus aureus* gsf nucleic acid, a *Pneumocystis jirovecii* dhps nucleic acid, a *Chlamydia trachomatis* tmRNA nucleic acid, a *Ureaplasma urealyticum* mba nucleic acid, a *Ureaplasma parvum* ure nucleic acid, a *Ureaplasma* spp. ure nucleic acid, a *Bartonella* spp. ssrA nucleic acid, a *Streptococcus agalactiae* cfb nucleic acid, a *Neisseria meningitidis* sodC nucleic acid, or any combination of two or more thereof are amplified by real-time PCR, for example real-time TAQMAN® PCR. Techniques for nucleic acid amplification are well-known to those of ordinary skill in the art.

Typically, at least two primers are utilized in the amplification reaction. In some examples, amplification of an *Acinetobacter baumannii* nucleic acid involves contacting the *Acinetobacter baumannii* nucleic acid with one or more primers (such as two or more primers) that are capable of hybridizing to and directing the amplification of an *Acinetobacter baumannii* nucleic acid, such as a primer capable of hybridizing under high or very high stringency conditions to an *Acinetobacter baumannii* nucleic acid sequence set forth as SEQ NO: 1, for example a primer that is least 90% identical (such as 91%, 92%, 93%, 94%, 95%, 96%, 97%, 98%, 99%, or 100% identical) to the nucleotide sequence set forth as one of SEQ ID NOs: 12 or 13. In one example, an *Acinetobacter baumannii* oxa-51 nucleic acid is amplified utilizing a pair of primers, such as a forward primer at least 90% identical to SEQ ID NO: 12 and a reverse primer at least 90% identical to SEQ ID NO: 13, such as a forward primer comprising or consisting essentially of SEQ ID NO: 12 and a reverse primer comprising or consisting essentially of SEQ ID NO: 13.

In other examples, amplification of a *Chlamydia trachomatis* nucleic acid involves contacting the *Chlamydia trachomatis* nucleic acid with one or more primers (such as two or more primers) that are capable of hybridizing to and directing the amplification of a *Chlamydia trachomatis* nucleic acid, such as a primer capable of hybridizing under high or very high stringency conditions to a *Chlamydia trachomatis* nucleic acid sequence set forth as SEQ NO: 2, for example a primer that is least 90% identical (such as 91%, 92%, 93%, 94%, 95%, 96%, 97%, 98%, 99%, or 100% identical) to the nucleotide sequence set forth as one of SEQ ID NOs: 36 or 37. In one example, a *Chlamydia trachomatis* tmRNA nucleic acid is amplified utilizing a pair of primers, such as a forward primer at least 90% identical to SEQ ID NO: 36 and a reverse primer at least 90% identical to SEQ ID NO: 37, such as a forward primer comprising or consisting essentially of SEQ ID NO: 36 and a reverse primer comprising or consisting essentially of SEQ ID NO: 37.

In further examples, amplification of an *Escherichia coli* and/or *Shigella* nucleic acid involves contacting the *Escherichia coli* and/or *Shigella* nucleic acid with one or more primers (such as two or more primers) that are capable of hybridizing to and directing the amplification of an *Escherichia coli* and/or *Shigella* nucleic acid, such as a primer capable of hybridizing under high or very high stringency conditions to an *Escherichia coli* and/or *Shigella* nucleic acid sequence set forth as SEQ NO: 3, for example a primer that is least 90% identical (such as 91%, 92%, 93%, 94%, 95%, 96%, 97%, 98%, 99%, or 100% identical) to the nucleotide sequence set forth as one of SEQ ID NOs: 27 or 28. In one example, an *Escherichia coli* uidA nucleic acid is amplified utilizing a pair of primers, such as a forward primer at least 90% identical to SEQ ID NO: 27 and a reverse primer at least 90% identical to SEQ ID NO: 28, such as a forward primer comprising or consisting essentially of SEQ ID NO: 27 and a reverse primer comprising or consisting essentially of SEQ ID NO: 28.

In some examples, amplification of a *Klebsiella pneumoniae* nucleic acid involves contacting the *Klebsiella pneumoniae* nucleic acid with one or more primers (such as two or more primers) that are capable of hybridizing to and directing the amplification of a *Klebsiella pneumoniae* nucleic acid, such as a primer capable of hybridizing under high or very high stringency conditions to a *Klebsiella pneumoniae* nucleic acid sequence set forth as SEQ NO: 4, for example a primer that is least 90% identical (such as 91%, 92%, 93%, 94%, 95%, 96%, 97%, 98%, 99%, or 100% identical) to the nucleotide sequence set forth as one of SEQ ID NOs: 18 or 19. In one example, a *Klebsiella pneumoniae* nifA nucleic acid is amplified utilizing a pair of primers, such as a forward primer at least 90% identical to SEQ ID NO: 18 and a reverse primer at least 90% identical to SEQ ID NO: 19, such as a forward primer comprising or consisting essentially of SEQ ID NO: 18 and a reverse primer comprising or consisting essentially of SEQ ID NO: 19. In other examples, amplification of a *Klebsiella pneumoniae* nucleic acid involves contacting the *Klebsiella pneumoniae* nucleic acid with one or more primers (such as two or more primers) that are capable of hybridizing to and directing the amplification of a *Klebsiella pneumoniae* nucleic acid, such as a primer capable of hybridizing under high or very high stringency conditions to a *Klebsiella pneumoniae* nucleic acid sequence set forth as SEQ NO: 57, for example a primer that is least 90% identical (such as 91%, 92%, 93%, 94%, 95%, 96%, 97%, 98%, 99%, or 100% identical) to the nucleotide sequence set forth as one of SEQ ID NOs: 58 or 59. In one example, a *Klebsiella pneumoniae* diguanylate cyclase nucleic acid is amplified utilizing a pair of primers, such as a forward primer at least 90% identical to SEQ ID NO: 58 and a reverse primer at least 90% identical to SEQ ID NO: 59, such as a forward primer comprising or consisting essentially of SEQ ID NO: 58 and a reverse primer comprising or consisting essentially of SEQ ID NO: 59.

In additional examples, amplification of a *Moraxella catarrhalis* nucleic acid involves contacting the *Moraxella* catarrhalis nucleic acid with one or more primers (such as two or more primers) that are capable of hybridizing to and directing the amplification of a *Moraxella catarrhalis* nucleic acid, such as a primer capable of hybridizing under high or very high stringency conditions to a *Moraxella catarrhalis* nucleic acid sequence set forth as SEQ NO: 5, for example a primer that is least 90% identical (such as 91%, 92%, 93%, 94%, 95%, 96%, 97%, 98%, 99%, or 100% identical) to the nucleotide sequence set forth as one of SEQ ID NOs: 24 or 25. In one example, a *Moraxella catarrhalis* purH nucleic acid is amplified utilizing a pair of primers, such as a forward primer at least 90% identical to SEQ ID NO: 24 and a reverse primer at least 90% identical to SEQ ID NO: 25, such as a forward primer comprising or consisting essentially of SEQ ID NO: 24 and a reverse primer comprising or consisting essentially of SEQ ID NO: 25.

In additional examples, amplification of a *Pneumocystis jirovecii* nucleic acid involves contacting the *Pneumocystis jirovecii* nucleic acid with one or more primers (such as two or more primers) that are capable of hybridizing to and directing the amplification of a *Pneumocystis jirovecii* nucleic acid, such as a primer capable of hybridizing under high or very high stringency conditions to a *Pneumocystis jirovecii* nucleic acid sequence set forth as SEQ NO: 6, for example a primer that is least 90% identical (such as 91%, 92%, 93%, 94%, 95%, 96%, 97%, 98%, 99%, or 100% identical) to the nucleotide sequence set forth as one of SEQ ID NOs: 33 or 34. In one example, a *P. jirovecii* dhps nucleic acid is amplified utilizing a pair of primers, such as a forward primer at least 90% identical to SEQ ID NO: 33 and a reverse primer at least 90% identical to SEQ ID NO: 34, such as a forward primer comprising or consisting essentially of SEQ ID NO: 33 and a reverse primer comprising or consisting essentially of SEQ ID NO: 34.

In further examples, amplification of a *Pseudomonas aeruginosa* nucleic acid involves contacting the *Pseudomonas aeruginosa* nucleic acid with one or more primers (such as two or more primers) that are capable of hybridizing to and directing the amplification of a *Pseudomonas aeruginosa* nucleic acid, such as a primer capable of hybridizing under high or very high stringency conditions to a *Pseudomonas aeruginosa* nucleic acid sequence set forth as SEQ NO: 7, for example a primer that is least 90% identical (such as 91%, 92%, 93%, 94%, 95%, 96%, 97%, 98%, 99%, or 100% identical) to the nucleotide sequence set forth as one of SEQ ID NOs: 15 or 16. In one example, a *Pseudomonas aeruginosa* gyrB nucleic acid is amplified utilizing a pair of primers, such as a forward primer at least 90% identical to SEQ ID NO: 15 and a reverse primer at least 90% identical to SEQ ID NO: 16, such as a forward primer comprising or consisting essentially of SEQ ID NO: 15 and a reverse primer comprising or consisting essentially of SEQ ID NO: 16.

In still further examples, amplification of a *Staphylococcus aureus* nucleic acid involves contacting the *Staphylococcus aureus* nucleic acid with one or more primers (such as two or more primers) that are capable of hybridizing to and directing the amplification of a *Staphylococcus aureus* nucleic acid, such as a primer capable of hybridizing under high or very high stringency conditions to a *Staphylococcus aureus* nucleic acid sequence set forth as SEQ NO: 8, for example a primer that is least 90% identical (such as 91%, 92%, 93%, 94%, 95%, 96%, 97%, 98%, 99%, or 100% identical) to the nucleotide sequence set forth as one of SEQ ID NOs: 30 or 31. In one example, a *Staphylococcus aureus* gsf nucleic acid is amplified utilizing a pair of primers, such as a forward primer at least 90% identical to SEQ ID NO: 30 and a reverse primer at least 90% identical to SEQ ID NO: 31, such as a forward primer comprising or consisting essentially of SEQ ID NO: 30 and a reverse primer comprising or consisting essentially of SEQ ID NO: 31.

In other examples, amplification of a *Toxoplasma gondii* nucleic acid involves contacting the *Toxoplasma gondii* nucleic acid with one or more primers (such as two or more primers) that are capable of hybridizing to and directing the amplification of a *Toxoplasma gondii* nucleic acid, such as a primer capable of hybridizing under high or very high stringency conditions to a *Toxoplasma gondii* nucleic acid sequence set forth as SEQ NO: 9, for example a primer that is least 90% identical (such as 91%, 92%, 93%, 94%, 95%, 96%, 97%, 98%, 99%, or 100% identical) to the nucleotide sequence set forth as one of SEQ ID NOs: 21 or 22. In one example, a *Toxoplasma gondii* ssrRNA nucleic acid is amplified utilizing a pair of primers, such as a forward primer at least 90% identical to SEQ ID NO: 21 and a reverse primer at least 90% identical to SEQ ID NO: 22, such as a forward primer comprising or consisting essentially of SEQ ID NO: 21 and a reverse primer comprising or consisting essentially of SEQ ID NO: 22.

In additional examples, amplification of a *Ureaplasma parvum* nucleic acid involves contacting the *Ureaplasma parvum* nucleic acid with one or more primers (such as two or more primers) that are capable of hybridizing to and directing the amplification of a *Ureaplasma parvum* nucleic acid, such as a primer capable of hybridizing under high or very high stringency conditions to a *Ureaplasma parvum* nucleic acid sequence set forth as SEQ NO: 10, for example a primer that is least 90% identical (such as 91%, 92%, 93%, 94%, 95%, 96%, 97%, 98%, 99%, or 100% identical) to the nucleotide sequence set forth as one of SEQ ID NOs: 42 or 43. In one example, a *Ureaplasma parvum* ure nucleic acid is amplified utilizing a pair of primers, such as a forward primer at least 90% identical to SEQ ID NO: 42 and a reverse primer at least 90% identical to SEQ ID NO: 43, such as a forward primer comprising or consisting essentially of SEQ ID NO: 42 and a reverse primer comprising or consisting essentially of SEQ ID NO: 43.

In further examples, amplification of a *Ureaplasma urealyticum* nucleic acid involves contacting the *Ureaplasma urealyticum* nucleic acid with one or more primers (such as two or more primers) that are capable of hybridizing to and directing the amplification of a *Ureaplasma urealyticum* nucleic acid, such as a primer capable of hybridizing under high or very high stringency conditions to a *Ureaplasma urealyticum* nucleic acid sequence set forth as SEQ NO: 11, for example a primer that is least 90% identical (such as 91%, 92%, 93%, 94%, 95%, 96%, 97%, 98%, 99%, or 100% identical) to the nucleotide sequence set forth as one of SEQ ID NOs: 39 or 40. In one example, a *Ureaplasma urealyticum* mba nucleic acid is amplified utilizing a pair of primers, such as a forward primer at least 90% identical to SEQ ID NO: 39 and a reverse primer at least 90% identical to SEQ ID NO: 40, such as a forward primer comprising or consisting essentially of SEQ ID NO: 39 and a reverse primer comprising or consisting essentially of SEQ ID NO: 40.

In additional examples, amplification of a *Ureaplasma* spp. nucleic acid involves contacting the *Ureaplasma* spp. nucleic acid with one or more primers (such as two or more primers) that are capable of hybridizing to and directing the amplification of a *Ureaplasma* spp. nucleic acid, such as a primer capable of hybridizing under very high stringency conditions to a *Ureaplasma* spp. nucleic acid sequence set forth as SEQ NO: 10, for example a primer that is least 90% identical (such as 91%, 92%, 93%, 94%, 95%, 96%, 97%, 98%, 99%, or 100% identical) to the nucleotide sequence set forth as one of SEQ ID NOs: 45 or 46. In one example, a *Ureaplasma* spp. ure nucleic acid is amplified utilizing a pair of primers, such as a forward primer at least 90% identical to SEQ ID NO: 45 and a reverse primer at least 90% identical to SEQ ID NO: 46, such as a forward primer comprising or consisting essentially of SEQ ID NO: 45 and a reverse primer comprising or consisting essentially of SEQ ID NO: 46.

In further examples, amplification of a *Bartonella* spp. nucleic acid involves contacting the *Bartonella* spp. nucleic acid with one or more primers (such as two or more primers) that are capable of hybridizing to and directing the amplification of a *Bartonella* spp. nucleic acid, such as a primer capable of hybridizing under high or very high stringency conditions to a *Bartonella* spp. ssrA nucleic acid sequence (such as SEQ ID NO: 52), for example a primer that is least 90% identical (such as 91%, 92%, 93%, 94%, 95%, 96%, 97%, 98%, 99%, or 100% identical) to the nucleotide sequence set forth as one of SEQ ID NOs: 48, 49, or 51. In one example, a *Bartonella* spp. ssrA nucleic acid is amplified utilizing a pair of primers, such as a forward primer at least 90% identical to SEQ ID NO: 48 and a reverse primer at least 90% identical to SEQ ID NO: 49, such as a forward primer comprising or consisting essentially of SEQ ID NO: 48 and a reverse primer comprising or consisting essentially of SEQ ID NO: 49. In other examples, a *Bartonella* spp. ssrA nucleic acid is amplified utilizing a pair of primers, such as a forward primer at least 90% identical to SEQ ID NO: 51 and a reverse primer at least 90% identical to SEQ ID NO: 49, such as a forward primer comprising or consisting essentially of SEQ ID NO: 51 and a reverse primer comprising or consisting essentially of SEQ ID NO: 49.

In other examples, amplification of a *Streptococcus agalactiae* nucleic acid involves contacting the *Streptococcus agalactiae* nucleic acid with one or more primers (such as two or more primers) that are capable of hybridizing to and directing the amplification of a *Streptococcus agalactiae* nucleic acid, such as a primer capable of hybridizing under high or very high stringency conditions to a *Streptococcus agalactiae* nucleic acid sequence set forth as SEQ NO: 53, for example a primer that is least 90% identical (such as 91%, 92%, 93%, 94%, 95%, 96%, 97%, 98%, 99%, or 100% identical) to the nucleotide sequence set forth as one of SEQ ID NOs: 54 or 55. In one example, a *Streptococcus agalactiae* cfb nucleic acid is amplified utilizing a pair of primers, such as a forward primer at least 90% identical to SEQ ID NO: 54 and a reverse primer at least 90% identical to SEQ ID NO: 55, such as a forward primer comprising or consisting essentially of SEQ ID NO: 54 and a reverse primer comprising or consisting essentially of SEQ ID NO: 55.

In other examples, amplification of a *Neisseria meningitidis* nucleic acid involves contacting the *Neisseria meningitidis* nucleic acid with one or more primers (such as two or more primers) that are capable of hybridizing to and directing the amplification of a *Neisseria meningitidis* nucleic acid, such as a primer capable of hybridizing under high or very high stringency conditions to a *Neisseria meningitidis* nucleic acid sequence set forth as SEQ NO: 61, for example a primer that is least 90% identical (such as 91%, 92%, 93%, 94%, 95%, 96%, 97%, 98%, 99%, or 100% identical) to the nucleotide sequence set forth as one of SEQ ID NOs: 62 or 63. In one example, a *Neisseria meningitidis* sodC nucleic acid is amplified utilizing a pair of primers, such as a forward primer at least 90% identical to SEQ ID NO: 62 and a reverse primer at least 90% identical to SEQ ID NO: 63, such as a forward primer comprising or consisting essentially of SEQ ID NO: 62 and a reverse primer comprising or consisting essentially of SEQ ID NO: 63.

The amplified *Acinetobacter baumannii*, *Pseudomonas aeruginosa*, *Klebsiella pneumooniae*, *Toxoplasma gondii*, *Moraxella catarrhalis*, *Escherichia coli/Shigella*, *Staphylococcus aureus*, *Pneumocystis jirovecii*, *Chlamydia trachomatis*, *Ureaplasma urealyticum*, *Ureaplasma parvum* ure, *Ureaplasma* spp. *Bartonella* spp., *Streptococcus agalactiae*, or *Neisseria meningitidis* nucleic acid can be detected in real-time, for example by real-time PCR, in order to determine the presence and/or the amount of a pathogen nucleic acid in a sample. In this manner, an amplified nucleic acid sequence can be detected using a probe specific for the product amplified from the target sequence of interest. Suitable probes for real-time PCR include those described herein, such as a probe having a nucleic acid sequence at least 90% identical to SEQ ID NO: 14, 17, 20, 23, 26, 29, 32, 35, 38, 41, 44, 47, 50, 56, 60, or 64. In particular examples of the disclosed methods, multiplex real-time PCR is utilized to detect one or more (for example, at least 2, 3, 4, 5, 6, 7, 8, 9, 10, 11, 12, 13, 14, or 15) of an *Acinetobacter baumannii*, *Pseudomonas aeruginosa*, *Klebsiella pneumooniae*, *Toxoplasma gondii*, *Moraxella catarrhalis*, *Escherichia coli/Shigella*, *Staphylococcus aureus*, *Pneumocystis jirovecii*, *Chlamydia trachomatis*, *Ureaplasma urealyticum*, *Ureaplasma parvum*, *Ureaplasma* spp. *Bartonella* spp., *Streptococcus agalactiae*, or *Neisseria meningitidis* nucleic acid present in the sample. In other examples of the disclosed methods, simultaneous multipathogen detection (such as multiple singleplex real-time PCR reactions, for example on a single array or card) is utilized to detect one or more (for example, at least 2, 3, 4, 5, 6, 7, 8, 9, 10, 11, 12, 13, 14, or 15) of an *Acinetobacter baumannii*, *Pseudomonas aeruginosa*, *Klebsiella pneumooniae*, *Toxoplasma gondii*, *Moraxella catarrhalis*, *Escherichia coli/Shigella*, *Staphylococcus aureus*, *Pneumocystis jirovecii*, *Chlamydia trachomatis*, *Ureaplasma urealyticum*, *Ureaplasma parvum*, *Ureaplasma* spp. *Bartonella* spp., *Streptococcus agalactiae*, or *Neisseria meningitidis* nucleic acid present in the sample.

Real-time PCR monitors the fluorescence emitted during the reaction as an indicator of amplicon production during each PCR cycle, as opposed to endpoint detection. The real-time progress of the reaction can be viewed in some systems. Typically, real-time PCR uses the detection of a fluorescent reporter. Typically, the fluorescent reporter's signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

In one embodiment, the fluorescently-labeled probes (such as probes disclosed herein) rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a donor fluorophore and an acceptor or quencher fluorophore on the same probe (for example, using a molecular beacon or a TAQMAN® probe) can identify a probe that specifically hybridizes to the nucleic acid of interest and in this way, using an *Acinetobacter baumannii* oxa-51 probe, a *Pseudomonas aeruginosa* gyrB probe, a *Klebsiella pneumoniae* nifA probe or a *Klebsiella pneumoniae* diguanylate cyclase probe, a *Toxoplasma gondii* ssrRNA probe, a *Moraxella catarrhalis* purH probe, an *Escherichia coli/Shigella* uidA probe, a *Staphylococcus aureus* gsf probe, a *Pneumocystis jirovecii* dhps probe, a *Chlamydia trachomatis* tmRNA probe, a *Ureaplasma urealyticum* mba probe, a *Ureaplasma parvum* ure probe, a *Ureaplasma* spp. ure probe, a *Bartonella* spp. ssrA probe, a *Streptococcus agalactiae* cfb probe, or a *Neisseria meningitidis* sodC probe can detect the presence and/or amount of the respective pathogen in a sample.

In some embodiments, the fluorescently-labeled DNA probes used to identify amplification products have spectrally distinct emission wavelengths, thus allowing them to be distinguished within the same reaction tube, for example in multiplex PCR, such as a multiplex real-time PCR. In some embodiments, the probes and primers disclosed herein are used in multiplex real-time PCR. For example, multiplex PCR permits the simultaneous detection of one or more (for example, at least 2, 3, 4, 5, 6, 7, 8, 9, 10, 11, 12, 13, 14, or 15) of the amplification products of *Acinetobacter baumannii* oxa-51 nucleic acid, a *Pseudomonas aeruginosa* gyrB nucleic acid, a *Klebsiella pneumoniae* nifA nucleic acid, a *Klebsiella pneumoniae* diguanylate cyclase nucleic acid, a *Toxoplasma gondii* ssrRNA nucleic acid, a *Moraxella catarrhalis* purH nucleic acid, an *Escherichia coli/Shigella* uidA nucleic acid, a *Staphylococcus aureus* gsf nucleic acid, a *Pneumocystis jirovecii* dhps nucleic acid, a *Chlamydia trachomatis* tmRNA nucleic acid, a *Ureaplasma urealyticum* mba nucleic acid, a *Ureaplasma parvum* ure nucleic acid, a *Ureaplasma* spp. ure nucleic acid, a *Bartonella* spp. ssrA nucleic acid, a *Streptococcus agalactiae* cfb nucleic acid, and a *Neisseria meningitidis* sodC nucleic acid. Using the disclosed primers and probes, any combination of *Acinetobacter baumannii, Pseudomonas aeruginosa, Klebsiella pneumoniae, Toxoplasma gondii, Moraxella catarrhalis, Escherichia coli/Shigella, Staphylococcus aureus, Pneumocystis jirovecii, Chlamydia trachomatis, Ureaplasma urealyticum, Ureaplasma parvum* ure, *Ureaplasma* spp., *Bartonella* spp. *Streptococcus agalactiae*, and *Neisseria meningitidis* nucleic acids can be detected. In some examples, the multiplex reaction may include one or more of the primers and probes disclosed herein and primers and probes for detection of additional pathogens.

In other examples, the probes and primers disclosed herein are used in a bead-based multiplex assay (see, e.g., U.S. Pat. No. 6,939,720). For example, probes specific for each pathogen (such as the probes disclosed herein) are attached to different fluorescently labeled beads and are hybridized to amplified DNA from the sample. The probes will only significantly hybridize if the particular pathogen is present in the sample. The hybridized beads are then captured, for example with a biotinylated detector molecule, and the relative fluorescence of the beads for each label is measured.

In another embodiment, a melting curve analysis of the amplified target nucleic acid can be performed subsequent to the amplification process. The $T_m$ of a nucleic acid sequence depends on the length of the sequence and its G/C content. Thus, the identification of the $T_m$ for a nucleic acid sequence can be used to identify the amplified nucleic acid, for example by using double-stranded DNA binding dye chemistry, which quantitates the amplicon production by the use of a non-sequence specific fluorescent intercalating agent (such as SYBR® Green or ethidium bromide). SYBR® Green is a fluorogenic minor groove binding dye that exhibits little fluorescence when in solution but emits a strong fluorescent signal upon binding to double-stranded DNA. Typically, SYBR® Green is used in singleplex reactions, however when coupled with melting point analysis, it can be used for multiplex reactions.

Any type of thermal cycler apparatus can be used for the amplification of pathogen or control nucleic acids and/or the determination of hybridization. Examples of suitable apparatuses include PTC-100® Peltier Thermal Cycler (MJ Research, Inc.; San Francisco, CA), ROBOCYCLER® 40 Temperature Cycler (Agilent/Stratagene; Santa Clara, CA), or GENEAMP® PCR System 9700 (Applied Biosystems; Foster City, CA). For real-time PCR, any type of real-time thermocycler apparatus can be used. For example, iCYCLER iQ™ or CFX96™ real-time detection systems (Bio-Rad, Hercules, CA), LightCycler® systems (Roche, Mannheim, Germany), ABI™ systems such as the 7000, 7300, 7500, 7700, or 7900 systems or the VIIA™ 7 real-time PCR system (Applied Biosystems; Foster City, CA), MX4000™, MX3000™ or MX3005™ qPCR systems (Agilent/Stratagene; Santa Clara, CA), DNA Engine OPTICON® Continuous Fluorescence Detection System (Bio-Rad, Hercules, CA), ROTOR-GENE® Q real-time cycler (Qiagen, Valencia, CA), or SMARTCYCLER® system (Cepheid, Sunnyvale, CA) can be used to amplify nucleic acid sequences in real-time. In some embodiments, real-time PCR is performed using a TAQMAN® array format, for example, a microfluidic card in which each well is pre-loaded with primers and probes for a particular target. The reaction is initiated by adding a sample including nucleic acids and assay reagents (such as a PCR master mix) and running the reactions in a real-time thermocycler apparatus.

In some embodiments, a microfluidic card includes at least one well containing primers and probes for at least one of *Acinetobacter baumannii, Pseudomonas aeruginosa, Klebsiella pneumooniae, Toxoplasma gondii, Moraxella catarrhalis, Escherichia coli/Shigella, Staphylococcus aureus, Pneumocystis jirovecii, Chlamydia trachomatis, Ureaplasma urealyticum, Ureaplasma parvum* ure, *Ureaplasma* spp. ure, *Bartonella* spp. ssrA nucleic acid, *Streptococcus agalactiae, Neisseria meningitidis*, or any combination or two or more thereof (such as 2, 3, 4, 5, 6, 7, 8, 9, 10, 11, 12, 13, 14, or 15 thereof). In one non-limiting example, the card includes at least one well containing *Acinetobacter baumannii* primers and probe (e.g., SEQ ID NOs: 12-14), at least one well containing *Pseudomonas aeruginosa* primers and probe (e.g., SEQ ID NOs: 15-17), at least one well containing *Klebsiella pneumoniae* primers and probe (e.g., SEQ ID NOs: 18-20 or SEQ ID NOs: 58-60), at least one well containing *Toxoplasma gondii* primers and probe (e.g., SEQ ID NOs: 21-23), at least one well containing *Moraxella catarrhalis* primers and probe (e.g., SEQ ID NOs: 24-26), at least one well containing *E. coli/Shigella* primers and probe (e.g., SEQ ID NOs: 27-29), at least one well containing *Staphylococcus aureus* primers and probe (e.g., SEQ ID NOs: 30-32), at least one well containing *Pneumocystis jirovecii* primers and probe (e.g., SEQ ID NOs: 33-35), at least one well containing *Chlamydia trachomatis* primers and probe (e.g., SEQ ID NOs: 36-38), at least one well containing *Ureaplasma urealyticum* primers and probe (e.g., SEQ ID NOs: 39-41), at least one well containing *Ureaplasma parvum* primers and probe (e.g., SEQ ID NOs: 42-44), at least one well containing *Ureaplasma* spp. primers and probe (e.g., SEQ ID NOs: 45-47), at least one well containing *Bartonella* spp. primers and probe (e.g., SEQ ID NOs: 48-50 and/or SEQ ID NOs: 49-51), at least one well containing *Streptococcus agalactiae* primers and probe (e.g., SEQ ID NOs: 54-56), and at least one well containing *Neisseria meningitidis* primers and probe (e.g., SEQ ID NOs: 62-64).

In another non-limiting example, the card includes at least one well containing *Chlamydia trachomatis* primers and probe (e.g., SEQ ID NOs: 36-38) and at least one well containing *Ureaplasma* spp. primers and probe (e.g., SEQ ID NOs: 45-47). In yet another non-limiting example, the card includes at least one well containing *Staphylococcus aureus* primers and probe (e.g., SEQ ID NOs: 30-32), at least one well containing *Pseudomonas aeruginosa* primers and probe (e.g., SEQ ID NOs: 15-17), at least one well containing *E. coli/Shigella* primers and probe (e.g., SEQ ID NOs: 27-29), at least one well containing *Klebsiella pneumoniae* primers and probe (e.g., SEQ ID NOs: 18-20), at least one well containing *Acinetobacter baumannii* primers and probe (e.g., SEQ ID NOs: 12-14), at least one well containing *Toxoplasma gondii* primers and probe (e.g., SEQ ID NOs: 21-23), at least one well containing *Ureaplasma* spp. primers and probe (e.g., SEQ ID NOs: 45-47), at least one well containing *Chlamydia trachomatis* primers and probe (e.g., SEQ ID NOs: 36-38), and at least one well containing *Streptococcus agalactiae* primers and probe (e.g., SEQ ID NOs: 54-56). In some examples, this card may also include at least one well containing *Neisseria meningitidis* primers and probe (e.g., SEQ ID NOs: 62-64) and/or at least one well containing *Salmonella* spp. primers and probe (e.g., SEQ ID NOs: 65-67). The card may include additional primers and probes in additional wells, such as positive control primers and probes, or primers and probes for additional pathogens or other nucleic acids of interest. In some examples, a card may additionally include wells containing primers and probes for one or more of *Mycoplasma pneumoniae*, *Chlamydophila pneumoniae*, *Bordetella pertussis*, adenovirus, influenza virus (A or B), parainfluenza virus (type 1, 2, or 3), respiratory syncytial virus, parechovirus, enterovirus, human metapneumovirus, rubella, *Streptococcus pneumoniae*, *Streptococcus pyogenes*, rhinovirus, Group B *Streptococcus*, Herpes simplex virus (1 or 2), pan-*Haemophilus influenzae*, pan-*Salmonella*, *Neisseria meningitidis*, cytomegalovirus, or any combination of two or more thereof. Additional combinations of assays can be selected and included on a TAC, as will be understood by one of ordinary skill in the art.

In some embodiments, the probe is detectably labeled, either with an isotopic or non-isotopic label; in alternative embodiments, the target nucleic acid is labeled. Non-isotopic labels can, for instance, comprise a fluorescent or luminescent molecule, or an enzyme, co-factor, enzyme substrate, or hapten. The probe is incubated with a single-stranded or double-stranded preparation of RNA, DNA, or a mixture of both, and hybridization is determined. In some examples, the hybridization results in a detectable change in signal such as in increase or decrease in signal, for example from the labeled probe. Thus, detecting hybridization comprises detecting a change in signal from the labeled probe during or after hybridization relative to signal from the label before hybridization.

In some examples, the disclosed methods can predict with a sensitivity of at least 90% and a specificity of at least 90% for presence of an *Acinetobacter baumannii*, *Pseudomonas aeruginosa*, *Klebsiella pneumooniae*, *Toxoplasma gondii*, *Moraxella catarrhalis*, *Escherichia coli*, *Shigella*, *Staphylococcus aureus*, *Pneumocystis jirovecii*, *Chlamydia trachomatis*, *Ureaplasma urealyticum*, *Ureaplasma parvum*, *Ureaplasma* spp., *Bartonella* spp., *Streptococcus agalactiae*, and/or *Neisseria meningitidis* nucleic acid, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%.

IV. Probes and Primers

Probes and primers suitable for use in the disclosed methods are described herein. Such probes and primers include nucleic acid molecules capable of hybridizing to the disclosed nucleic acid molecules, such as SEQ ID NOs: 1-11 or 52.

A. Probes

Probes capable of hybridizing to and detecting the presence of *Acinetobacter baumannii*, *Pseudomonas aeruginosa*, *Klebsiella pneumooniae*, *Toxoplasma gondii*, *Moraxella catarrhalis*, *Escherichia coli*, *Shigella*, *Staphylococcus aureus*, *Pneumocystis jirovecii*, *Chlamydia trachomatis*, *Ureaplasma urealyticum*, *Ureaplasma parvum*, *Ureaplasma* spp., *Bartonella* spp., *Streptococcus agalactiae*, or *Neisseria meningitidis* nucleic acid molecules are disclosed. In some embodiments, the disclosed probes are between 10 and 40 nucleotides in length, such as 10, 11, 12, 13, 14, 15, 16, 17, 18, 19, 20, 21, 22, 23, 24, 25, 26, 27, 28, 29, 30, 31, 32, 32, 34, 35, 36, 37, 38, 39, or 40 nucleotides in length and are capable of hybridizing to the disclosed nucleic acid molecules. In some examples, the probes are at least 10, 15, 20, 25, 30, 35, or 40 nucleotides in length. In other examples, the probes may be no more than 10, 15, 20, 25, 30, 35, or 40 nucleotides in length. The disclosed probes may also include a 3' C6 CpG in some examples.

In several embodiments, a probe is capable of hybridizing under high or very high stringency conditions to an *Acinetobacter baumannii* nucleic acid sequence set forth as SEQ ID NO: 1. In some examples, a probe capable of hybridizing to an *Acinetobacter baumannii* oxa-51 nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as TGACTGCTAATCCAAAT-CACAGCGCTTCA (SEQ ID NO: 14). In several embodiments, a probe capable of hybridizing to an *Acinetobacter baumannii* oxa-51 nucleic acid molecule consists essentially of, or consists of, a nucleic acid sequence set forth as SEQ ID NO: 14.

In some embodiments, a probe is capable of hybridizing under high or very high stringency conditions to a *Chlamydia trachomatis* nucleic acid sequence set forth as SEQ ID NO: 2. In some examples, a probe capable of hybridizing to a *Chlamydia trachomatis* tmRNA nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as ATGCGGAGGGCGTTGGCTGG (SEQ ID NO: 38). In several embodiments, a probe capable of hybridizing to a *Chlamydia trachomatis* tmRNA nucleic acid molecule consists essentially of, or consists of, a nucleic acid sequence set forth as SEQ ID NO: 38.

In other embodiments, a probe is capable of hybridizing under high or very high stringency conditions to an *Escherichia coli* and/or *Shigella* spp. nucleic acid sequence set forth as SEQ ID NO: 3. In some examples, a probe capable of hybridizing to an *Escherichia coli* and/or *Shigella* spp. nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as TACGGCGTGA-CATCGGCTTCAAATG (SEQ ID NO: 29). In several embodiments, a probe capable of hybridizing to an *Escherichia coli* uidA nucleic acid molecule consists essentially of, or consists of, a nucleic acid sequence set forth as SEQ ID NO: 29. In particular embodiments, the probe capable of hybridizing to an *Escherichia coli* uidA nucleic acid molecule is capable of hybridizing to a uidA nucleic acid molecule from any an *Escherichia coli* and/or *Shigella* species or serogroup.

In additional embodiments, a probe is capable of hybridizing under high or very high stringency conditions to a *Klebsiella pneumoniae* nucleic acid sequence set forth as SEQ ID NO: 4. In some examples, a probe capable of hybridizing to a *Klebsiella pneumoniae* nifA nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as ACGCTGAGCACCTCCTGCAACGT (SEQ ID NO: 20). In several embodiments, a probe capable of hybridizing to a *Klebsiella pneumoniae* nifA nucleic acid molecule consists essentially of, or consists of, a nucleic acid sequence set forth as SEQ ID NO: 20. In other embodiments, a probe is capable of hybridizing under high or very high stringency conditions to a *Klebsiella pneumoniae* nucleic acid sequence set forth as SEQ ID NO: 57. In some examples, a probe capable of hybridizing to a *Klebsiella pneumoniae* diguanylate cyclase nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as CCACCACGCTCATCTGTTTCGCC (SEQ ID NO: 60). In several embodiments, a probe capable of hybridizing to a *Klebsiella pneumoniae* diguanylate cyclase nucleic acid molecule consists essentially of, or consists of, a nucleic acid sequence set forth as SEQ ID NO: 60.

In further embodiments, a probe is capable of hybridizing under high or very high stringency conditions to a *Moraxella catarrhalis* nucleic acid sequence set forth as SEQ ID NO: 5. In some examples, a probe capable of hybridizing to a *Moraxella catarrhalis* purH nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as CACAGCGGGCAGCTCAATTTGACCTA (SEQ ID NO: 26). In several embodiments, a probe capable of hybridizing to a *Moraxella catarrhalis* purH nucleic acid molecule consists essentially of, or consists of, a nucleic acid sequence set forth as SEQ ID NO: 26.

In still further embodiments, a probe is capable of hybridizing under high or very high stringency conditions to a *Pneumocystis jirovecii* nucleic acid sequence set forth as SEQ ID NO: 6. In some examples, a probe capable of hybridizing to a *Pneumocystis jirovecii* dhps nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as ACAGGGTGTCTTACAGGTGATGTTATGCCAAAAG (SEQ ID NO: 35). In several embodiments, a probe capable of hybridizing to a *Pneumocystis jirovecii* dhps nucleic acid molecule consists essentially of, or consists of, a nucleic acid sequence set forth as SEQ ID NO: 35. In one example, a probe capable of hybridizing to a *Pneumocystis jirovecii* dhps nucleic acid molecule includes or consists of a nucleic acid sequence set forth as ACAGGGTGTCT"T"ACAGGTGATGTTATGCCAAAAG (SEQ ID NO: 35), where "T" is BHQ1.

In additional embodiments, a probe is capable of hybridizing under high or very high stringency conditions to a *Pseudomonas aeruginosa* nucleic acid sequence set forth as SEQ ID NO: 7. In some examples, a probe capable of hybridizing to a *Pseudomonas aeruginosa* gyrB nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as TCCGTCGCCACAACAAGGTCTGGGAA (SEQ ID NO: 17). In several embodiments, a probe capable of hybridizing to a *Pseudomonas aeruginosa* gyrB nucleic acid molecule consists essentially of, or consists of, a nucleic acid sequence set forth as SEQ ID NO: 17.

In other embodiments, a probe is capable of hybridizing under high or very high stringency conditions to a *Staphylococcus aureus* nucleic acid sequence set forth as SEQ ID NO: 8. In some examples, a probe capable of hybridizing to a *Staphylococcus aureus* gsf nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as TTCCATATGACCACCACGAGTCTTAGCACC (SEQ ID NO: 32). In several embodiments, a probe capable of hybridizing to a *Staphylococcus aureus* gsf nucleic acid molecule consists essentially of, or consists of, a nucleic acid sequence set forth as SEQ ID NO: 32.

In some embodiments, a probe is capable of hybridizing under high or very high stringency conditions to a *Toxoplasma gondii* nucleic acid sequence set forth as SEQ ID NO: 9. In some examples, a probe capable of hybridizing to a *Toxoplasma gondii* ssrRNA nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as ATCGCGTTGACTTCGGTCTGCGAC (SEQ ID NO: 23). In several embodiments, a probe capable of hybridizing to a *Toxoplasma gondii* ssrRNA nucleic acid molecule consists essentially of, or consists of, a nucleic acid sequence set forth as SEQ ID NO: 23.

In some embodiments, a probe is capable of hybridizing under high or very high stringency conditions to a *Ureaplasma parvum* nucleic acid sequence set forth as SEQ ID NO: 10. In some examples, a probe capable of hybridizing to a *Ureaplasma parvum* ure nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as TCAGTGAACGTGAGTATCTAAACCACCAGC (SEQ ID NO: 44). In several embodiments, a probe capable of hybridizing to a *Ureaplasma parvum* ure nucleic acid molecule consists essentially of, or consists of, a nucleic acid sequence set forth as SEQ ID NO: 44. In some examples, a probe capable of hybridizing to a *Ureaplasma parvum* ure nucleic acid molecule includes or consists of a nucleic acid sequence set forth as TCAGTGAACG"T"GAGTATCTAAACCACCAGC (SEQ ID NO: 44), where "T" is BHQ1.

In additional embodiments, a probe is capable of hybridizing under high or very high stringency conditions to a *Ureaplasma urealyticum* nucleic acid sequence set forth as SEQ ID NO: 11. In some examples, a probe capable of hybridizing to a *Ureaplasma urealyticum* mba nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as CACAGCAACTACCCCTGCTCCCACTAA (SEQ ID NO: 41). In several embodiments, a probe capable of hybridizing to a *Ureaplasma urealyticum* mba nucleic acid molecule consists essentially of, or consists of, a nucleic acid sequence set forth as SEQ ID NO: 41.

In several embodiments, a probe capable of hybridizing to a *Ureaplasma* spp. ure nucleic acid molecule contains a nucleic acid sequence that is at least 90% identical, such as at least 91%, 92%, 93%, 94%, 95%, 96%, 97%, 98%, 99% or even 100% identical, to the nucleotide sequence set forth as CCACCAGCAATAACAGTTGTAATACCACCATC (SEQ ID NO: 47). In several embodiments, a probe capable of hybridizing to a *Ureaplasma* spp. ure nucleic acid molecule consists essentially of, or consists of, a nucleic acid sequence set forth as SEQ ID NO: 47. In several examples, a probe capable of hybridizing to a *Ureaplasma* spp. ure nucleic acid molecule includes or consists of a nucleic acid sequence set forth as CCACCAGCAA"T"AACAGTTGTAATACCACCATC (SEQ ID NO: 47), where "T" is BHQ1. In particular embodiments, the probe capable of hybridizing to a *Ureaplasma* spp. ure nucleic acid molecule is capable of hybridizing to a ure nucleic acid molecule from any *Ureaplasma* species or serogroup (for example, *Ureaplasma parvum* or *Ureaplasma urealyticum*).

In additional embodiments, a probe is capable of hybridizing under high or very high stringency conditions to a *Bartonella* spp. nucleic acid sequence set forth as SEQ ID NO: 52. In several embodiments, a probe capable of hybridizing to a *Bartonella* spp. ssrA nucleic molecule contains a nucleic acid sequence that is at least 90% identical, such as at least 91%, 92%, 93%, 94%, 95%, 96%, 97%, 98%, 99% or even 100% identical, to the nucleotide sequence set forth as ACCCCGCTTAAACCTGCGACG (SEQ ID NO: 50). In several embodiments, a probe capable of hybridizing to a *Bartonella* spp. ssrA nucleic acid molecule consists essentially of, or consists of, a nucleic acid sequence set forth as SEQ ID NO: 50. In particular embodiments, the probe capable of hybridizing to a *Bartonella* spp. ssrA nucleic acid molecule is capable of hybridizing to a ssrA nucleic acid molecule from any *Bartonella* species or serogroup (for example, *B. alsatica, B. bacilliformis, B. birtlesii, B. bovis, B capreoli, B. chomelii, B. clarridgeiae, B. doshiae, B. elizabethae, B. henselae, B. grahamii, B. japonica, B. koehlerae, B. melophagi, B. phoceensis, B. quintana, B. rochalimae, B. schoenbuchensis, B. silvatica, B. taeniae, B. taylorii, B. tribocorum, B. vinsonii, and/or B. washoensis*).

In some embodiments, a probe is capable of hybridizing under high or very high stringency conditions to a *Streptococcus agalactiae* nucleic acid sequence set forth as SEQ ID NO: 53. In some examples, a probe capable of hybridizing to a *Streptococcus agalactiae* cfb nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as AGACTTCATTGCGTGCCAACCCTGAGAC (SEQ ID NO: 56). In several embodiments, a probe capable of hybridizing to a *Streptococcus agalactiae* cfb nucleic acid molecule consists essentially of, or consists of, a nucleic acid sequence set forth as SEQ ID NO: 56.

In further embodiments, a probe is capable of hybridizing under high or very high stringency conditions to a *Neisseria meningitidis* nucleic acid sequence set forth as SEQ ID NO: 61. In some examples, a probe capable of hybridizing to a *Neisseria meningitidis* sodC nucleic molecule includes a nucleic acid sequence that is at least 90% identical, such as at least 91%, 92%, 93%, 94%, 95%, 96%, 97%, 98%, 99%, or even 100% identical, to the nucleotide sequence set forth as CGCAGGCGGTCACTGGGATC (SEQ ID NO: 64). In several embodiments, a probe capable of hybridizing to a *Neisseria meningitidis* sodC nucleic acid molecule consists essentially of, or consists of, a nucleic acid sequence set forth as SEQ ID NO: 64.

In some examples, the probe is labeled with one or more fluorophores. Examples of suitable fluorophore labels are provided above. In some examples, the fluorophore is a donor fluorophore. In particular, non-limiting examples, the probes disclosed herein are labeled with FAM, although one of ordinary skill in the art can select other fluorophore labels for use in the disclosed methods. In other examples, the fluorophore is an accepter fluorophore, such as a fluorescence quencher. In some examples, the probe includes both a donor fluorophore and an accepter or quencher fluorophore, for example a donor fluorophore such as a FAM and an acceptor fluorophore such as a BLACK HOLE® quencher (such as BHQ1, BHQ2, or BHQ3) or TAMRA. Appropriate donor/acceptor fluorophore pairs can be selected using routine methods. In one example, the donor emission wavelength is one that can significantly excite the acceptor, thereby generating a detectable emission from the acceptor. In some examples, the probe is modified at the 3'-end to prevent extension of the probe by a polymerase.

In some examples, the acceptor fluorophore (such as a fluorescence quencher) is attached to the 3' end of the probe and the donor fluorophore is attached to a 5' end of the probe. In other examples, the acceptor fluorophore (such as a fluorescence quencher) is attached to the 5' end of the probe and the donor fluorophore is attached to a 3' end of the probe. In another particular example, the acceptor fluorophore (such as a fluorescence quencher) is attached to a modified nucleotide (such as a T) and the donor fluorophore is attached to a 5' end of the probe. In some examples, the donor fluorophore is FAM and the acceptor fluorophore is BHQ1. In particular embodiments, the probes disclosed herein include a donor fluorophore attached to the 5' end and an acceptor fluorophore attached to the 3' end.

B. Primers

Primers capable of hybridizing to and directing the amplification of *Acinetobacter baumannii, Pseudomonas aeruginosa, Klebsiella pneumoniae, Toxoplasma gondii, Moraxella catarrhalis, Escherichia coli, Shigella, Staphylococcus aureus, Pneumocystis jirovecii, Chlamydia trachomatis, Ureaplasma urealyticum, Ureaplasma parvum, Ureaplasma* spp., *Bartonella* spp., *Streptococcus agalactiae*, or *Neisseria meningitidis* nucleic acid molecules are also disclosed. The primers disclosed herein are between 10 to 40 nucleotides in length, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or even 40 nucleotides in length. In some examples, the primers are at least 10, 15, 20, 25, 30, 35, or 40 nucleotides in length. In other examples, the primers may be no more than 10, 15, 20, 25, 30, 35, or 40 nucleotides in length.

In several embodiments, a primer is capable of hybridizing to and directing the amplification of an *Acinetobacter baumannii* oxa-51 nucleic acid molecule (such as SEQ ID NO: 1) and includes a nucleic acid sequence that is at least 90% identical, such as at least 91%, 92%, 93%, 94%, 95%, 96%, 97%, 98%, 99%, or even 100% identical, to the nucleic acid sequence set forth as TATTTTATTTCAGCCTGCTCACCTT (SEQ ID NO: 12) or AAATACTTCTGTGGTGGTTGCCTTA (SEQ ID NO: 13). In several embodiments, a primer capable of hybridizing to and directing the amplification of an *Acinetobacter baumannii* oxa-51 nucleic acid molecule consists essentially of, or consists of a nucleic acid sequence set forth as SEQ ID NO: 12 or SEQ ID NO: 13.

In some embodiments, a primer is capable of hybridizing to and directing the amplification of a *Chlamydia trachomatis* tmRNA nucleic acid molecule (such as SEQ ID NO: 2) and includes a nucleic acid sequence that is at least 90% identical, such as at least 91%, 92%, 93%, 94%, 95%, 96%, 97%, 98%, 99%, or even 100% identical, to the nucleic acid sequence set forth as GGTGTAAAGGTTTCGACTTAGAA (SEQ ID NO: 36) or CGAACACCGGGTCACC (SEQ ID NO: 37). In several embodiments, a primer capable of hybridizing to and directing the amplification of a *Chlamydia trachomatis* tmRNA nucleic acid molecule consists essentially of, or consists of a nucleic acid sequence set forth as SEQ ID NO: 36 or SEQ ID NO: 37.

In other embodiments, a primer is capable of hybridizing to and directing the amplification of an *Escherichia coli* and/or *Shigella* spp. nucleic acid molecule (such as SEQ ID NO: 3) and includes a nucleic acid sequence that is at least 90% identical, such as at least 91%, 92%, 93%, 94%, 95%, 96%, 97%, 98%, 99%, or even 100% identical, to the nucleic acid sequence set forth as GAGCATCAGGGTGGC-TATACG (SEQ ID NO: 27) or ATAGTCTGCCAGTTCAGTTC (SEQ ID NO: 28). In several embodiments, a primer capable of hybridizing to and directing the amplification of an *Escherichia coli* and/or *Shigella* spp. nucleic acid molecule consists essentially of, or consists of a nucleic acid sequence set forth as SEQ ID NO: 27 or SEQ ID NO: 28.

In additional embodiments, a primer is capable of hybridizing to and directing the amplification of a *Klebsiella pneumoniae* nifA nucleic acid molecule (such as SEQ ID NO: 4) and includes a nucleic acid sequence that is at least 90% identical, such as at least 91%, 92%, 93%, 94%, 95%, 96%, 97%, 98%, 99%, or even 100% identical, to the nucleic acid sequence set forth as TGCTGCATAAAGGCATCGTT (SEQ ID NO: 18) or CCACCGAGGCCAGCAA (SEQ ID NO: 19). In several embodiments, a primer capable of hybridizing to and directing the amplification of a *Klebsiella pneumoniae* nifA nucleic acid molecule consists essentially of, or consists of a nucleic acid sequence set forth as SEQ ID NO: 18 or SEQ ID NO: 19. In further embodiments, a primer is capable of hybridizing to and directing the amplification of a *Klebsiella pneumoniae* diguanylate cyclase nucleic acid molecule (such as SEQ ID NO: 57) and includes a nucleic acid sequence that is at least 90% identical, such as at least 91%, 92%, 93%, 94%, 95%, 96%, 97%, 98%, 99%, or even 100% identical, to the nucleic acid sequence set forth as TGCAGATAATTCACGCCCAG (SEQ ID NO: 58) or ACCCGCTGGACGCCAT (SEQ ID NO: 59). In several embodiments, a primer capable of hybridizing to and directing the amplification of a *Klebsiella pneumoniae* diguanylate cyclase nucleic acid molecule consists essentially of, or consists of a nucleic acid sequence set forth as SEQ ID NO: 58 or SEQ ID NO: 59.

In further embodiments, a primer is capable of hybridizing to and directing the amplification of a *Moraxella catarrhalis* purH nucleic acid molecule (such as SEQ ID NO: 5) and includes a nucleic acid sequence that is at least 90% identical, such as at least 91%, 92%, 93%, 94%, 95%, 96%, 97%, 98%, 99%, or even 100% identical, to the nucleic acid sequence set forth as GGTGAGTTGCCACAGC (SEQ ID NO: 24) or AGTAGACCGCCATTGACTC (SEQ ID NO: 25). In several embodiments, a primer capable of hybridizing to and directing the amplification of a *Moraxella catarrhalis* purH nucleic acid molecule consists essentially of, or consists of a nucleic acid sequence set forth as SEQ ID NO: 24 or SEQ ID NO: 25.

In still further embodiments, a primer is capable of hybridizing to and directing the amplification of a *Pneumocystis jirovecii* dhps nucleic acid molecule (such as SEQ ID NO: 6) and includes a nucleic acid sequence that is at least 90% identical, such as at least 91%, 92%, 93%, 94%, 95%, 96%, 97%, 98%, 99%, or even 100% identical, to the nucleic acid sequence set forth as TAATGGTTTGCCTTGGTTGCTT (SEQ ID NO: 33) or CACAGCCTCCTAAAACAGAT (SEQ ID NO: 34). In several embodiments, a primer capable of hybridizing to and directing the amplification of a *Pneumocystis jirovecii* dhps nucleic acid molecule consists essentially of, or consists of a nucleic acid sequence set forth as SEQ ID NO: 33 or SEQ ID NO: 34.

In other embodiments, a primer is capable of hybridizing to and directing the amplification of a *Pseudomonas aeruginosa* gyrB nucleic acid molecule (such as SEQ ID NO: 7) and includes a nucleic acid sequence that is at least 90% identical, such as at least 91%, 92%, 93%, 94%, 95%, 96%, 97%, 98%, 99%, or even 100% identical, to the nucleic acid sequence set forth as GTCTCGGTGGTGAACG (SEQ ID NO: 15) or TGGATGTTGCTGAAGGTCTC (SEQ ID NO: 16). In several embodiments, a primer capable of hybridizing to and directing the amplification of a *Pseudomonas aeruginosa* gyrB nucleic acid molecule consists essentially of, or consists of a nucleic acid sequence set forth as SEQ ID NO: 15 or SEQ ID NO: 16.

In additional embodiments, a primer is capable of hybridizing to and directing the amplification of a *Staphylococcus aureus* gsf nucleic acid molecule (such as SEQ ID NO: 8) and includes a nucleic acid sequence that is at least 90% identical, such as at least 91%, 92%, 93%, 94%, 95%, 96%, 97%, 98%, 99%, or even 100% identical, to the nucleic acid sequence set forth as CGGGTTAGGTGAATTGATTGTTT-TAT (SEQ ID NO: 30) or CGCATTTGAGCTGAAGTTG (SEQ ID NO: 31). In several embodiments, a primer capable of hybridizing to and directing the amplification of a *Staphylococcus aureus* gsf nucleic acid molecule consists essentially of, or consists of a nucleic acid sequence set forth as SEQ ID NO: 30 or SEQ ID NO: 31.

In other embodiments, a primer is capable of hybridizing to and directing the amplification of a *Toxoplasma gondii* ssrRNA nucleic acid molecule (such as SEQ ID NO: 9) and includes a nucleic acid sequence that is at least 90% identical, such as at least 91%, 92%, 93%, 94%, 95%, 96%, 97%, 98%, 99%, or even 100% identical, to the nucleic acid sequence set forth as GGTGGTCCTCAGGTGAT (SEQ ID NO: 21) or CCACGGTAGTCCAATACAGTA (SEQ ID NO: 22). In several embodiments, a primer capable of hybridizing to and directing the amplification of a *Toxoplasma gondii* ssrRNA nucleic acid molecule consists essentially of, or consists of a nucleic acid sequence set forth as SEQ ID NO: 21 or SEQ ID NO: 22.

In further embodiments, a primer is capable of hybridizing to and directing the amplification of a *Ureaplasma parvum* ure nucleic acid molecule (such as SEQ ID NO: 10) and includes a nucleic acid sequence that is at least 90% identical, such as at least 91%, 92%, 93%, 94%, 95%, 96%, 97%, 98%, 99%, or even 100% identical, to the nucleic acid sequence set forth as ACAGATAATGTTGATATGAT-TGTGGGTAT (SEQ ID NO: 42) or CTAATGCAACAG-GAACTATTTCTG (SEQ ID NO: 43). In several embodiments, a primer capable of hybridizing to and directing the amplification of a *Ureaplasma parvum* ure nucleic acid molecule consists essentially of, or consists of a nucleic acid sequence set forth as SEQ ID NO: 42 or SEQ ID NO: 43.

In still further embodiments, a primer is capable of hybridizing to and directing the amplification of a *Ureaplasma urealyticum* mba nucleic acid molecule (such as SEQ ID NO: 11) and includes a nucleic acid sequence that is at least 90% identical, such as at least 91%, 92%, 93%, 94%, 95%, 96%, 97%, 98%, 99%, or even 100% identical, to the nucleic acid sequence set forth as ATTTCATATT-TAGTTTATTAGGAGATCGTTAT (SEQ ID NO: 39) or AGATTTAACATTTGAGCTAGAACAT (SEQ ID NO: 40). In several embodiments, a primer capable of hybridizing to and directing the amplification of a *Ureaplasma urealyticum* mba nucleic acid molecule consists essentially of, or consists of a nucleic acid sequence set forth as SEQ ID NO: 39 or SEQ ID NO: 40.

In additional embodiments, a primer is capable of hybridizing to and directing the amplification of a *Ureaplasma* spp. ure nucleic acid molecule (such as SEQ ID NO: 10) and includes a nucleic acid sequence that is at least 90% identical, such as at least 91%, 92%, 93%, 94%, 95%, 96%, 97%, 98%, 99%, or even 100% identical, to the nucleic acid sequence set forth as GGTTTAGATACTCACGTT-CACTGA (SEQ ID NO: 45) or GCTTTTGTACCATCAT-TCATACCTGT (SEQ ID NO: 46). In several embodiments, a primer capable of hybridizing to and directing the amplification of a *Ureaplasma* spp. ure nucleic acid molecule consists essentially of, or consists of a nucleic acid sequence set forth as SEQ ID NO: 45 or SEQ ID NO: 46.

In additional embodiments, a primer is capable of hybridizing to and directing the amplification of a *Bartonella* spp. ssrA nucleic acid molecule (such as SEQ ID NO: 52) and includes a nucleic acid sequence that is at least 90% identical, such as at least 91%, 92%, 93%, 94%, 95%, 96%, 97%, 98%, 99%, or even 100% identical, to the nucleic acid sequence set forth as GCTATGGTAATAAATGGACAAT-GAAATAA (SEQ ID NO: 48), GCTTCTGTTGCCAGGTG (SEQ ID NO: 49), or CTAAAT-GAGTAGTTGCAAATGACAAC (SEQ ID NO: 51). In several embodiments, a primer capable of hybridizing to and directing the amplification of a *Bartonella* spp. ssrA nucleic acid molecule consists essentially of, or consists of a nucleic acid sequence set forth as SEQ ID NO: 48, SEQ ID NO: 49, or SEQ ID NO: 51. In particular embodiments, the primer capable of hybridizing to and directing amplification of a *Bartonella* spp. ssrA nucleic acid molecule is capable of hybridizing to a ssrA nucleic acid molecule from any *Bartonella* species or serogroup (for example, *B. alsatica*, *B. bacilliformis*, *B. birtlesii*, *B. bovis*, *B capreoli*, *B. chomelii*, *B. clarridgeiae*, *B. doshiae*, *B. elizabethae*, *B. henselae*, *B. grahamii*, *B. japonica*, *B. koehlerae*, *B. melophagi*, *B. phoceensis*, *B. quintana*, *B. rochalimae*, *B. schoenbuchensis*, *B. silvatica*, *B. taeniae*, *B. taylorii*, *B. tribocorum*, *B. vinsonii*, and/or *B. washoensis*).

In additional embodiments, a primer is capable of hybridizing to and directing the amplification of a *Streptococcus agalactiae* cfb nucleic acid molecule (such as SEQ ID NO: 53) and includes a nucleic acid sequence that is at least 90% identical, such as at least 91%, 92%, 93%, 94%, 95%, 96%, 97%, 98%, 99%, or even 100% identical, to the nucleic acid sequence set forth as GGGAACAGATTATGAAAAACCG (SEQ ID NO: 54) or AAGGCTTCTACACGACTACCAA (SEQ ID NO: 55). In several embodiments, a primer capable of hybridizing to and directing the amplification of a *Streptococcus agalactiae* cfb nucleic acid molecule consists essentially of, or consists of a nucleic acid sequence set forth as SEQ ID NO: 54 or SEQ ID NO: 55.

In additional embodiments, a primer is capable of hybridizing to and directing the amplification of a *Neisseria meningitidis* sodC nucleic acid molecule (such as SEQ ID NO: 61) and includes a nucleic acid sequence that is at least 90% identical, such as at least 91%, 92%, 93%, 94%, 95%, 96%, 97%, 98%, 99%, or even 100% identical, to the nucleic acid sequence set forth as CTGTGAGC-CAAAAGAAAAAGAAG (SEQ ID NO: 62) or GAT-TTGTTGCTGTGCCATCAT (SEQ ID NO: 63). In several embodiments, a primer capable of hybridizing to and directing the amplification of a *Neisseria meningitidis* sodC nucleic acid molecule consists essentially of, or consists of a nucleic acid sequence set forth as SEQ ID NO: 62 or SEQ ID NO: 63.

In certain embodiments, the primers are utilized or provided as a set of primers, such as a pair of primers, capable of hybridizing to and amplifying a disclosed nucleic acid, such as one of SEQ ID NOs: 1-11, 52-53, 57, or 60. In some examples, the set of primers includes a pair of primers including SEQ ID NOs: 12 and 13, a pair of primers including SEQ ID NOs: 15 and 16, a pair of primers including SEQ ID NOs: 18 and 19, a pair of primers including SEQ ID NOs: 21 and 22, a pair of primers including SEQ ID NOs: 24 and 25, a pair of primers including SEQ ID NOs: 27 and 28, a pair of primers including SEQ ID NOs: 30 and 31, a pair of primers including SEQ ID NOs: 33 and 34, a pair of primers including SEQ ID NOs: 36 and 37, a pair of primers including SEQ ID NOs: 39 and 40, a pair of primers including SEQ ID NOs: 42 and 43, a pair of primers including SEQ ID NOs: 45 and 46, a pair of primers including SEQ ID NOs: 48 and 49, a pair of primers including SEQ ID NOs: 51 and 49, a pair of primers including SEQ ID NO: 54 and SEQ ID NO: 55, a pair of primers including SEQ ID NO: 58 and SEQ ID NO: 59, or a pair of primers including SEQ ID NO: 62 and SEQ IDNO: 63.

C. Probe and Primer Variants

Although exemplary probe and primer sequences are provided in SEQ ID NOs: 12-51, 54-56, 58-60, and 62-64, the primer and/or probe sequences can be varied slightly by moving the probe or primer a few nucleotides upstream or downstream from the nucleotide positions that they hybridize to on the target nucleic molecule acid, provided that the probe and/or primer is still specific for the target nucleic acid sequence, for example specific for one of SEQ ID NOs: 1-11, 52-53, 57, or 60. For example, variations of the probes and primers disclosed as SEQ ID NOs: 12-51, 54-56, 58-60, and 62-64 can be made by "sliding" the probes and/or primers a few nucleotides 5' or 3' from their positions, and such variation will still be specific for the respective target nucleic acid sequence.

Also provided by the present disclosure are probes and primers that include variations to the nucleotide sequences shown in any of SEQ ID NOs: 12-51, 54-56, 58-60, and 62-64, as long as such variations permit detection of the target nucleic acid molecule. For example, a probe or primer can have at least 90% sequence identity such as at least 91%, 92%, 93%, 94%, 95%, 96%, 97%, 98%, or 99% identity to a nucleic acid including of the sequence shown in any of SEQ ID NOs: 12-51, 54-56, 58-60, and 62-64. In such examples, the number of nucleotides does not change, but the nucleic acid sequence shown in any of SEQ ID NOs: 12-51, 54-56, 58-60, and 62-64 can vary at a few nucleotides, such as changes at 1, 2, 3, or 4 nucleotides.

The present application also provides probes and primers that are slightly longer or shorter than the nucleotide sequences shown in any of SEQ ID NOs: 12-51, 54-56, 58-60, and 62-64, as long as such deletions or additions permit detection of the desired target nucleic acid molecule, such as one of SEQ ID NOs: 1-11, 52-53, 57, or 60. For example, a probe or primer can include a few nucleotide deletions or additions at the 5'- or 3'-end of the probe or primers shown in any of SEQ ID NOs: 12-51, 54-56, 58-60, and 62-64, such as addition or deletion of 1, 2, 3, or 4 nucleotides from the 5'- or 3'-end, or combinations thereof (such as a deletion from one end and an addition to the other end). In such examples, the number of nucleotides changes.

Also provided are probes and primers that are degenerate at one or more positions (such as 1, 2, 3, 4, 5, or more positions), for example, a probe or primer that includes a mixture of nucleotides (such as 2, 3, or 4 nucleotides) at a specified position in the probe or primer. In some examples, the probes and primers disclosed herein include one or more synthetic bases or alternative bases (such as inosine). In other examples, the probes and primers disclosed herein include one or more modified nucleotides or nucleic acid analogues, such as one or more locked nucleic acids (see, e.g., U.S. Pat. No. 6,794,499) or one or more superbases (Nanogen, Inc., Bothell, WA). In other examples, the probes and primers disclosed herein include a minor groove binder conjugated to the 5' or 3' end of the oligonucleotide (see, e.g., U.S. Pat. No. 6,486,308).

V. Kits

The nucleic acid primers and probes disclosed herein can be supplied in the form of a kit for use in the detection of one or more of *Acinetobacter baumannii, Pseudomonas aeruginosa, Klebsiella pneumooniae, Toxoplasma gondii, Moraxella catarrhalis, Escherichia coli, Shigella, Staphylococcus aureus, Pneumocystis jirovecii, Chlamydia trachomatis, Ureaplasma urealyticum, Ureaplasma parvum, Ureaplasma* spp., *Bartonella* spp., *Streptococcus agalactiae,* or *Neisseria meningitidis* in a sample. In such a kit, an appropriate amount of one or more of the nucleic acid probes and/or primers (such as one or more of SEQ ID NOs: 12-51, 54-56, 58-60, and 62-64) are provided in one or more containers or in one or more individual wells of a multiwall plate or card. A nucleic acid probe and/or primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. The kits can include either labeled or unlabeled nucleic acid probes (for example, 1, 2, 3, 4, 5, 6, 7, 8, 9, 10, 11, 12, 13, 14, or 15 probes) for use in detection of *Acinetobacter baumannii, Pseudomonas aeruginosa, Klebsiella pneumoniae, Toxoplasma gondii, Moraxella catarrhalis, Escherichia coli, Shigella, Staphylococcus aureus, Pneumocystis jirovecii, Chlamydia trachomatis, Ureaplasma urealyticum, Ureaplasma parvum, Ureaplasma* spp., *Bartonella* spp., *Streptococcus agalactiae,* or *Neisseria meningitidis* nucleic acids. One or more control probes and/or primers for use in the PCR reactions also may be supplied in the kit. In some examples, the probes are detectably labeled.

In some examples, one or more sets of primers (such as the primers described above), such as pairs of primers (for example, 1, 2, 3, 4, 5, 6, 7, 8, 9, 10, 11, 12, 13, 14, or 15 pairs of primers), may be provided in pre-measured single use amounts in individual, typically disposable, tubes, wells, or equivalent containers. With such an arrangement, the sample to be tested for the presence of the target nucleic acids can be added to the individual tube(s) or well(s) and amplification carried out directly.

The amount of nucleic acid primer supplied in the kit can be any appropriate amount, and may depend on the target market to which the product is directed. For instance, if the kit is adapted for research or clinical use, the amount of each nucleic acid primer provided would likely be an amount sufficient to prime several PCR amplification reactions. General guidelines for determining appropriate amounts may be found in Innis et al., Sambrook et al., and Ausubel et al. A kit may include more than two primers in order to facilitate the PCR amplification of a larger number of target nucleic acid molecules, such as *Acinetobacter baumannii, Pseudomonas aeruginosa, Klebsiella pneumooniae, Toxoplasma gondii, Moraxella catarrhalis, Escherichia coli/Shigella, Staphylococcus aureus, Pneumocystis jirovecii, Chlamydia trachomatis, Ureaplasma urealyticum, Ureaplasma parvum, Ureaplasma* spp., *Bartonella* spp., *Streptococcus agalactiae,* or *Neisseria meningitidis* nucleic acids, or any combination of two or more thereof.

In some embodiments, kits also may include the reagents necessary to carry out PCR amplification reactions, including DNA sample preparation reagents, appropriate buffers (such as polymerase buffer), salts (for example, magnesium chloride), deoxyribonucleotides (dNTPs), and polymerases.

In particular embodiments, the kits include prepackaged probes, such as probes suspended in suitable medium in individual containers (for example, individually sealed tubes or wells). In some examples, the probes include those provided herein. In other particular embodiments, the kit includes equipment, reagents, and instructions for extracting and/or purifying nucleotides from a sample.

The present disclosure is illustrated by the following non-limiting Examples.

EXAMPLE 1

Primers and Probes

Primers and probes were designed for detection of *Acinetobacter baumannii, Pseudomonas aeruginosa, Klebsiella pneumooniae, Toxoplasma gondii, Moraxella catarrhalis, Escherichia coli/Shigella, Staphylococcus aureus, Pneumocystis jirovecii, Chlamydia trachomatis, Ureaplasma urealyticum, Ureaplasma parvum, Ureaplasma* spp., *Bartonella* spp., and *Streptococcus agalactiae.* In most cases, oligonucleotides were designed using Primer Express 3.0 software (Applied Biosystems, Foster City, CA) with slight modifications to optimize melting temperatures (Tm) and minimize intra- and inter-molecular interactions. Specificity of each set of oligonucleotides for the intended genus and/or species was assessed by sequence comparison using Basic Local Alignment Search Tool (BLAST) within the National Center for Biotechnology Information (NCBI) database (available on the world wide web at blast.ncbi.nlm.nih.gov/Blast.cgi). Primers and hydrolysis probes used for analytical validation were manufactured by the Biotechnology Core Facility at the Centers for Disease Control and Prevention (Atlanta, GA, USA).

The target genes and primer and probe sequences are shown in Table 1. Some probes (such as the *P. jirovecii, U. parvum,* and *Ureaplasma* spp. probes) include a BHQ1 internal quencher linked to a "T" nucleotide. Probes including an internal quencher include C6 CpG at the 3' end to prevent extension. In some examples, each probe includes 5' FAM label and a 3' BHQ1 label, except where indicated otherwise.

TABLE 1

Primers and probes for detection of pathogens

| Organism | Target | Oligo | Sequence | SEQ ID NO: | Final Conc. (nM) |
|---|---|---|---|---|---|
| Acinetobacter baumannii | oxa-51 | ABF1 | TATTTTTATTTCAGCCTGCTCACCTT | 12 | 1000 |
| | | ABR3 | AAATACTTCTGTGGTGGTTGCCTTA | 13 | 1000 |
| | | ABP1 | TGACTGCTAATCCAAATCACAGCGCTTCA | 14 | 200 |
| Pseudomonas aeruginosa | gyrB | PAF2 | GTCTCGGTGGTGAACG | 15 | 500 |
| | | PAR | TGGATGTTGCTGAAGGTCTC | 16 | 500 |
| | | PAP2 | TCCGTCGCCACAACAAGGTCTGGGAA | 17 | 100 |
| Klebsiella pneumoniae | nifA | KPF1 | TGCTGCATAAAGGCATCGTT | 18 | 1000 |
| | | KPR1 | CCACCGAGGCCAGCAA | 19 | 1000 |
| | | KPP1 | ACGCTGAGCACCTCCTGCAACGT | 20 | 200 |
| | diguanylate cyclase | For | TGCAGATAATTCACGCCCAG | 58 | 1000 |
| | | Rev | ACCCGCTGGACGCCAT | 59 | 1000 |
| | | Probe | CCACCACGCTCATCTGTTTCGCC | 60 | 200 |
| Toxoplasma gondii | ssrRNA | TGF2 | GGTGGTCCTCAGGTGAT | 21 | 1000 |
| | | TGR2 | CCACGGTAGTCCAATACAGTA | 22 | 1000 |
| | | TGP2 | ATCGCGTTGACTTCGGTCTGCGAC | 23 | 200 |
| Moraxella catarrhalis | purH | MCF2 | GGTGAGTTGCCACAGC | 24 | 1000 |
| | | MCR2 | AGTAGACCGCCATTGACTC | 25 | 1000 |
| | | MCP1 | CACAGCGGGCAGCTCAATTTGACCTA | 26 | 200 |
| Escherichia coli/ Shigella | uidA | ECSF1A | GAGCATCAGGGTGGCTATACG | 27 | 500 |
| | | ECSR1A | ATAGTCTGCCAGTTCAGTTC | 28 | 500 |
| | | ECSP1 | TACGGCGTGACATCGGCTTCAAATG | 29 | 100 |
| Staphylococcus aureus | gsf | SAF2 | CGGGTTAGGTGAATTGATTGTTTTAT | 30 | 1000 |
| | | SAR2 | CGCATTTGAGCTGAAGTTG | 31 | 1000 |
| | | SAP2 | TTCCATATGACCACCACGAGTCTTAGCACC | 32 | 200 |
| Pneumocystis jirovecii | dhps | PJF1 | TAATGGTTTGCCTTGGTTGCTT | 33 | 1000 |
| | | PJR2A | CACAGCCTCCTAAAACAGAT | 34 | 1000 |
| | | PJP2A | ACAGGGTGTCT"T"ACAGGTGATGTTATGCCAAAAG | 35 | 200 |
| Chlamydia trachomatis | tmRNA | CTF1 | GGTGTAAAGGTTTCGACTTAGAA | 36 | 1000 |
| | | CTR3 | CGAACACCGGGTCACC | 37 | 1000 |
| | | CTP1 | ATGCGGAGGGCGTTGGCTGG | 38 | 200 |
| Ureaplasma urealyticum | mba | UUF1 | ATTTCATATTTAGTTTATTAGGGAGATCGTTAT | 39 | 1000 |
| | | UUR1 | AGATTTAACATTTGAGCTAGAACAT | 40 | 1000 |
| | | UUP2 | CACAGCAACTACCCCTGCTCCCACTAA | 41 | 200 |
| Ureaplasma parvum | ure | PARVUMF3 | ACAGATAATGTTGATATGATTGTGGGTAT | 42 | 1000 |
| | | PARVUMR3 | CTAATGCAACAGGAACTATTTCTG | 43 | 1000 |

TABLE 1-continued

Primers and probes for detection of pathogens

| Organism | Target | Oligo | Sequence | SEQ ID NO: | Final Conc. (nM) |
|---|---|---|---|---|---|
| | | PARVUMP3i | TCAGTGAACG"T"GAGTATCTAAACCACCAGC | 44 | 200 |
| Ureaplasma spp. | ure | UPANF1 | GGTTTAGATACTCACGTTCACTGA | 45 | 500 |
| | | UPANR1 | GCTTTTGTACCATCATTCATACCTGT | 46 | 500 |
| | | UPANP1i | CCACCAGCAA"T"AACAGTTGTAATACCACCATC | 47 | 100 |
| Bartonella spp. | ssrA | ssrA-F | GCTATGGTAATAAATGGACAATGAAATAA | 48 | 500 |
| | | ssrA-R | GCTTCTGTTGCCAGGTG | 49 | 500 |
| | | ssrA-P | ACCCCGCTTAAACCTGCGACG | 50 | 100 |
| | | ssrA-F2 | CTAAATGAGTAGTTGCAAATGACAAC | 51 | |
| Streptococcus agalactiae | cfb | For | GGGAACAGATTATGAAAAACCG | 54 | 1000 |
| | | Rev | AAGGCTTCTACACGACTACCAA | 55 | 1000 |
| | | Probe | AGACTTCATTGCGTGCCAACCCTGAGAC | 56 | 200 |
| Neisseria meningitidis | sodC | For | CTGTGAGCCAAAAGAAAAAGAAG | 62 | 1000 |
| | | Rev | GATTTGTTGCTGTGCCATCAT | 63 | 1000 |
| | | Probe | CGCAGGCGGTCACTGGGATC | 64 | 200 |
| Salmonella spp. | ttrRSBCA | For | CTCACCAGGAGATTACAACATGG | 65 | 500 |
| | | Rev | AGCTCAGACCAAAAGTGACCATC | 66 | 500 |
| | | Probe | CACCGACGGCGAGACCGACTTT | 67 | 100 |

"T" = BHQ1 modification

EXAMPLE 2

Detection and Differentiation of *Bartonella* Species and Genotypes

Bacterial strains and DNA extraction: All bacterial strains were obtained from collections at the Centers for Disease Control and Prevention in Fort Collins, CO and Atlanta, GA. Nucleic acid was extracted from 33 *Bartonella* strains, including 25 defined species or subspecies using the QIAAMP DNA mini kit (Qiagen, Valencia, CA). *Bartonella* strains included in this study were: *B. alsatica* (IBS 382), *B. bacilliformis* (KC584), *B. birtlesii* (IBS 325), *B. bovis* (91-4), *B. capreoli* (WY-Elk), *B. chomelii* (A828), *B. clarridgeiae* (Houston-2), *B. doshiae* (R18), *B. elizabethae* (F9251), *B. henselae* (Houston-1), *B. grahamii* (V2), *B. japonica* (Fuji 18-1T), *B. koehlerae* (C-29), *B. melophagi* (K-2C), *B. phoceensis* (16120), *B. quintana* (Fuller), *B. rochalimae* (BMGH), *B. schoenbuchensis* (R1), *B. silvatica* (Fuji 23-1T), *B. tamiae* (Th307, Th239, and Th339), *B. taylorii* (M16), *B. tribocorum* (IBS 506), *B. vinsonii* subsp. *arupensis* (OK 94-513), *B. vinsonii* subsp. *vinsonii* (Baker), *B. washoensis* (Sb944nv), and *Bartonella* isolates (Sh6397ga, Sh6396ga, Sh6537ga, Sh8784ga, Sh8200ga, and Sh8776ga). Using the MAGNA PURE® Compact instrument with Total Nucleic Acid Isolation Kit I (Roche Applied Science, Indianapolis, IN), nucleic acid was extracted from 61 microorganisms that are closely related genetically to *Bartonella* or may occupy a similar ecological niche, including *Afipia broomii*, *Afipia clevelandensis*, *Afipia felis*, *Agrobacterium radiobacter*, *Agrobacterium tumefaciens*, *Babesia microti*, *Bordetella pertussis*, *Bordetella parapertussis*, *Bradyrhizobium*, *Brucella abortus*, *Brucella canis*, *Brucella melitensis*, *Brucella neotomae*, *Brucella ovis*, *Brucella suis*, *Campylobacter coli*, *Campylobacter fetus*, *Campylobacter jejuni*, *Citrobacter freundii*, *Enterobacter aerogenes*, *Enterobacter cloacae*, *Erwinia*, *Escherichia albertii* (2 strains), *Escherichia blattae*, *Escherichia coli* (4 strains), *Escherichia fergusonii*, *Escherichia hermanii*, *Escherichia vulneris*, *Haemophilus influenzae*, *Klebsiella oxytoca*, *Klebsiella pneumoniae*, *Kluyvera intermedia*, *Legionella pneumophila*, *Methylobacterium organophilum*, *Ochrobactrum anthropi* (3 strains), *Ochrobactrum intermedium*, *Oligella urethralis* (4 strains), *Psychrobacter phenylpyruvicus* (2 strains), *Raoultella planticola*, *Salmonella bongori*, *Salmonella enterica* (serovar Enteriditis, serovar Typhi, serovar Typhimurium), *Shigella boydii*, *Shigella dysenteriae*, *Shigella flexneri*, *Shigella sonnei*, *Toxoplasma gondii*, and *Vibrio cholerae*. Human genomic DNA was also tested for cross-reactivity. All nucleic acid extracts were normalized to 1 ng/μL in Tris-EDTA buffer.

Real-time PCR: Sequences of the ssrA (tmRNA) gene of five representative *Bartonella* species were obtained from the tmRNA Website (indiana.edu/~tmrna/) and GenBank (accession numbers: NC_005955.1, NC_005956.1, NC_010161.1, NC_012846.1, NC_008783.1). Sequences were aligned using the Clustal W method (ebi.ac.uk/Tools/msa/clustalw2/). Primers and probes were designed using Primer Express 3.0 software (Applied Biosystems, Foster City, CA) with some modification for amplification of a 301 bp region of ssrA. The reaction mix (25 µL) contained the following components: 12.5 µL 2× PerfeCta® MultiPlex qPCR SuperMix (Quanta Biosciences, Gaithersburg, MD), forward and reverse primers (ssrA-F: 5'-GCTATGGTAATAAATGGACAATGAAATAA-3' (SEQ ID NO: 48), ssrA-R: 5'-GCTTCTGTTGCCAGGTG-3' (SEQ ID NO: 49)) at a final concentration of 500 nM, FAM-labeled probe (5'FAM-ACCCCGCTTAAACCTGCGACG-3'BHQ1 (SEQ ID NO: 50)) at a final concentration of 100 nM, and 5 µL of extracted nucleic acid. Real-time PCR was performed on the Applied Biosystems 7500 real-time PCR instrument with the following thermocycling parameters: 1 cycle of 95° C. for 2 min followed by 45 cycles of 95° C. for 15 sec and 60° C. for 60 sec with data collection in the FAM channel. Primers and probe were tested using nuclease-free water (n=95) to ensure no signal in the absence of nucleic acid template. The limit of detection was independently determined and verified for four species (*B. quintana, B. henselae, B. bovis,* and *B. elizabethae*) by testing 10 replicates each of 10-fold serial dilutions of genomic DNA ranging from 1 ng/µL to 0.1 fg/µL. The limit of detection was identified as the lowest dilution at which amplification was observed in at least 50% of replicates. Specificity was assessed by performing the assay using 15 ng of nucleic acid from 61 different microorganisms representing 24 genera and 48 species.

Sequencing: Amplicons for sequencing were generated by conventional PCR with forward and reverse primers at 400 nM each using the Bio-Rad Dyad® thermal cycler (Bio-Rad, Hercules, Calif.) with the following thermocycling conditions: 95° for 2 min, 30 cycles of 95° for 15 sec, 60° for 60 sec, and 72° for 30 sec followed by 72° for 3 min. Amplicons were visualized by electrophoresis in a 1% agarose gel followed by staining with 0.05% methylene blue solution and purification using the Geneclean® Turbo kit (MP Biomedicals, Solon, OH). Sequencing reactions were performed in both directions using BigDye® Terminator 3.1 cycle sequencing kit (Applied Biosystems) according to the manufacturer's instructions with the same primers for the real-time PCR assay at a final concentration of 165 nM. Sequencing was performed on the Applied Biosystems 3130×L genetic analyzer.

Phylogenetic analysis: A 253 bp region of each amplified sequence (excluding forward and reverse primers) was used for alignment and phylogenetic comparison of *Bartonella* species and genotypes using Lasergene® version 8 software suite (DNASTAR, Madison, WI). All ssrA sequences were aligned using the Clustal V method. Phylogenetic trees were constructed using the neighbor-joining method and bootstrapping analysis with 1,000 replicates.

Testing of animal blood: Blood specimens collected from elk (*Cervus elaphus*) in Wyoming (n=56) and cattle (*Bos primigenius*) in the country of Georgia (n=89) between 2008-2009 were tested for *Bartonella* by bacterial culture using previously described methods (Bai et al., *Vet. Microbiol.* 148:329-332, 2011). The culture results from this cohort of elk have been reported previously (Bai et al., 2011). All specimens were extracted using the DNEASY® Blood and Tissue kit (Qiagen) or MAGNA PURE® Compact with Total Nucleic Acid Isolation Kit I (Roche Applied Science). Five or 10 µL of nucleic acid extract was used in each real-time PCR reaction.

Nucleotide sequence accession numbers: Thirty-four unique ssrA sequences obtained from *Bartonella* strains and isolates were submitted to GenBank and assigned the following accession numbers: JN029776 (*B. alsatica* IBS 382), JN029794 (*B. bacilliformis* KC584), JN029775 (*B. birtlesii* IBS325), JN029767 (*B. bovis* 91-4), JN029798 (*B. capreoli* WY-Elk), JN029773 (*B. chomelii* A828), JN029768 (*B. doshiae* R18), JN029774 (*B. elizabethae* F9251), JN029785 (*B. henselae* Houston-1), JN029795 (*B. grahamii* V2), JN029784 (*B. japonica* Fuji 18-1T), JN029769 (*B. koehlerae* C-29), JN029771 (*B. melophagi* K-2C), JN029770 (*B. phoceensis* 16120), JN029766 (*B. quintana* Fuller), JN029797 (*B. rochalimae* BMGH), JN029772 (*B. schoenbuchensis* R1), JN029782 (*B. silvatica* Fuji 23-1T), JN029778 (*B. taeniae* Th307), JN029779 (*B. taeniae* Th239), JN029780 (*B. taeniae* Th339), JN029781 (*B. taylorii* M16), JN029796 (*B. tribocorum* IBS 506), JN029783 (*B. vinsonii* subsp. *arupensis* OK 94-513), JN029777 (*B. vinsonii* subsp. *vinsonii* Baker), JN029786 (*B. washoensis* Sb944nv), JN029787 (*Bartonella* sp. Sh6397ga), JN029791 (*Bartonella* sp. Sh8200ga), JN029793 (*Bartonella* sp. Sh8776ga), JN029788 (*Bartonella* sp. Sh6396ga), JN029790 (*Bartonella* sp. Sh8784ga), JN029792 (*Bartonella* sp. Sh9282ga), JN029789 (*Bartonella* sp. Sh6537ga), JN982716 (*B. clarridgeiae* Houston-2). The ssrA sequence amplified from elk blood was assigned accession number JN982717, and the sequence identified in cattle blood was identical to *B. bovis* (JN029767).

Real-time PCR for detection of *Bartonella* ssrA: Amplification of the target sequence occurred with all *Bartonella* species (n=24) and unclassified *Bartonella* strains (n=7) tested (data not shown). Amplification curves demonstrated sigmoidal shape and had crossing threshold (Ct) values between 15 and 21 with 5 ng of DNA per reaction. No amplification was observed in no-template control (NTC) reactions (n=95) or with DNA from other microorganisms listed above (n=61) or human genomic DNA. The limit of detection was independently determined for four species (*B. quintana, B. henselae, B. bovis,* and *B. elizabethae*) and found to be ≤5 fg of nucleic acid per reaction.

*Bartonella* phylogeny based on ssrA genotypes: Phylogenetic analysis of ssrA sequences from each *Bartonella* strain or isolate showed that this region was sufficient to discriminate all *Bartonella* species and that separation of clades based on ssrA sequences was consistent with phylogeny based on gltA, which is considered a reliable tool for distinguishing closely related *Bartonella* genotypes (LaScola et al., *Trends Microbiol.* 11:318-321, 2003). First, the ssrA sequences from ruminant-associated *Bartonella*, including *B. chomelii*, 163 *B. capreoli, B. bovis, B. melophagi,* and *B. schoenbuchensis* formed an independent clade; sequence identity between these species was ≥94%. Further, both subspecies of *B. vinsonii* (*vinsonii* and *arupensis*) included in this study formed a separate grouping in the tree with 98% identity, as did three strains of the recently identified pathogenic *Bartonella* species *B. taeniae* (≥97.2% identity) (Kosoy et al., *J. Clin. Microbiol.* 46:772-775, 2008). Among all ssrA sequences, the lowest percent identity (75.3 to 84.1%) was observed for strains of *B. taeniae* relative to other *Bartonella* species, thus supporting the separation of *B. taeniae* as a novel species (Kosoy et al., 2008). The division of two additional clades which are similarly separated by gltA comparison, one consisting of *B.*

*elizabethae* and *B. tribocorum* and the other including *B. henselae* and *B. koehlerae*, were also supported by the phylogenetic analysis of ssrA. Overall, the separation of major *Bartonella* clades based on ssrA sequences was consistent with phylogeny based on gltA (Kosoy et al., *Am. J. Trop. Med. Hyg.* 82:1140-1145, 2010; Maillard et al., *Int. Syst. Evol. Microbiol.* 54:215-220, 2004).

Detection and identification of *Bartonella* in animal blood: This assay was used to screen elk and cattle blood specimens for the presence of *Bartonella* and compared to bacterial culture results. *Bartonella* DNA was detected in 16 of 55 (29.1%) and 42 of 89 (47.2%) specimens from elk and cattle, respectively. The appropriate amplicon size was confirmed for positive samples. Using traditional culturing methods, *Bartonella* was recovered from only 4 of 55 (7.3%) elk and 34 of 89 (38.2%) cattle specimens. Since comparison of ssrA genotypes from *Bartonella* reference strains showed that this sequence provides sufficient information to discriminate *Bartonella* genotypes, we performed sequencing analysis of a subset of ssrA sequences amplified from elk (n=3) and cattle (n=5) specimens in order to identify the *Bartonella* species present. Analysis of ssrA sequences from elk blood revealed one genotype which clustered most closely with *B. capreoli*, a *Bartonella* species found in wild and domestic ruminants (Bai et al., *Vet. Microbiol.* 148:329-332, 2011). These results were consistent with previous identification of *B. capreoli* isolated from these samples using sequencing analysis of gltA (Bai et al., 2011). Similarly, a single ssrA genotype present in cattle blood was found to be identical to *B. bovis* (99.7% similarity). This result corroborated previous identification of *B. bovis* from these cattle specimens by analysis of gltA.

Samples from four patients in Thailand presenting with headache, myalgia, dizziness, fatigues, and rat exposure and animal ownership were analyzed for *Bartonella* infection. Blood clots from each patient were inoculated into *Bartonella* alpha-Proteobacteria growth medium and incubated aerobically at 35° C. with 5% $CO_2$ for seven days. DNA was extracted from this pre-enrichment using the QIAAMP® DNA mini kit (Qiagen, Chasworth, CA) according to manufacturer's instruction, and analyzed using real-time PCR targeting ssrA, as described above. PCR assays were performed using a CFX96™ Real-Time System (Bio-Rad, Hercules, CA). Amplicons were recovered from PCR reactions by gel-purification and sequenced in both directions using an Applied Biosystems Model 3130 Genetic Analyzer (Applied Biosystems, Foster City, CA).

Sequences obtained from the patients were very similar to the type strain of *B. vinsonii* subsp. *arupensis*. The ssrA sequences revealed two similar variants. One variant was identical to the type strain of *B. vinsonii*. subsp. *arupensis* (JN029783) and was identified in three of the patients (45-00250, 45-01217, and 45-01239). The other variant (JN394654), from patient 45-00025, was 2.8% divergent from the type strain of *B. vinsonii*. subsp. *arupensis*.

EXAMPLE 3

Multiple Pathogen Detection in Population-Based Study of Neonatal Infection

Materials and Methods

Real-time PCR assay design and analytical validation: A panel of neonatologists with expertise in neonatal infection and South Asia was convened, and the Delphi method (Dalkey and Helmer, *Management Sci.* 9:458-467, 1963) was used to identify organisms of the highest priority for testing in nasopharyngeal (NP) and oropharyngeal (OP) swabs and blood specimens from neonates. Primers and hydrolysis probes were designed as described in Example 1.

All newly developed real-time PCR assays were evaluated using individual RT-qPCR reactions prior to use on the TAQMAN array card (TAC) format. Each assay was tested using nuclease-free water as template (n≥95) to ensure no fluorescence amplification signal was observed in the absence of nucleic acid. The limit of detection was independently determined for each assay by testing at least 3 replicates each of a 10-fold dilution series of specific total nucleic acid ranging from 0.1 fg/μL to 1 ng/μL. Inclusivity was assessed by testing representative isolates, including various subspecies, serotypes, or clonal groups, as appropriate (Table 2). Specificity of each assay was assessed by testing 15 ng of nucleic acid from at least 200 different bacteria, viruses, and protozoa representing 36 genera and 143 species. In addition to the most closely related species to each target pathogen, this panel also included commensals of the respiratory tract and human nucleic acid.

Oligonucleotide preparation for TAC manufacturing: Oligonucleotides for TAC production were manufactured by Integrated DNA Technologies (Coralville, IA) or Biosearch Technologies (Novato, CA), diluted and combined to 20× reaction concentration, and provided to Life Technologies (Foster City, CA) for custom manufacturing of study-specific TACs. The 20× concentration corresponds to a 1× final reaction concentration in the 1 μL reaction within each TAC well on the finished card. Total nucleic acid was extracted from a series of 10-fold dilutions of each organism and tested to determine the potential impact of oligonucleotide concentration on assay sensitivity.

Clinical specimens: Clinical specimens, including whole blood and combined NP/OP swabs, were obtained from enrolled neonates at three ANISA study sites: Sylhet, Bangladesh; Karachi, Pakistan; and Matiari, Pakistan. NP/OP swabs were collected and placed together in 1 mL Universal Transport Media (UTM, Copan Diagnostics, Murrieta, CA) and stored at −70° C. prior to extraction. Blood specimens were collected in standard EDTA collection tubes and stored at 4° C. for short-term storage (≤72 h post-collection) or −70° C. for longer storage prior to nucleic acid extraction and testing by TAC. Additional respiratory clinical specimens (NP/OP swabs) from the historical collection at the Centers for Disease Control and Prevention (Atlanta, GA) were also used for some experiments.

Specimen processing and nucleic acid extraction: Total nucleic acid (TNA) was extracted from clinical specimens using the MAGNA PURE® Compact instrument (Roche Applied Sciences, Indianapolis, IN) with Nucleic Acid Isolation Kit I and Total NA Plasma protocol. For NP/OP swab specimens, 400 μL of UTM was extracted and eluted in 100 μL. For extraction of whole blood, 300 μL of blood in EDTA was mixed with 100 μL of a freshly-prepared solution of lytic enzymes consisting of 1.5 mg/mL lysostaphin, 2500 U/mL mutanolysin, and 200 mg/mL lysozyme (Sigma-Aldrich, St. Louis, MO) in Tris-EDTA (TE) buffer and incubated at 37° C. for 30-60 min. prior to extraction on the MAGNA PURE® Compact, with elution in 100 μL. To assess the potential impact of a pre-lysis step on recovery of TNA from a variety of pathogens, healthy donor blood was spiked with 10-fold serial dilutions of quantified culture stock of gram-positive bacteria (*S. aureus*), gram-negative bacterium (*K. pneumoniae*), or an RNA virus (enterovirus) and tested using individual RT-qPCR reactions. Spiked blood specimens were extracted directly or incubated with TE buffer or TE buffer containing lytic enzymes at 37° C. for 30 min. prior to extraction. Ct values for spiked blood experiments were compared using Student's two-tailed t test.

Individual real-time PCR assay performance: All individual real-time PCR assays were performed on the Applied Biosystems 7500 Real-Time PCR system (Life Technologies, Foster City, CA) with the following cycling conditions: 45° C. for 10 minutes, 94° C. for 10 minutes, 45 cycles of 94° C. for 30 seconds and 60° C. for 60 seconds, with data acquisition in the FAM channel during the 60° C. step. Each reaction consisted of 1× AGPATH-ID™ One-step RT-PCR buffer and 1× AGPATH-ID™ One-step RT-PCR enzyme mix (Applied Biosystems, Foster City, CA) or 1× QSCRIPT™ XLT One-step RT-qPCR TOUGHMIX®, low ROX (Quanta Biosciences, Gaithersburg, MD, USA), forward and reverse primers and FAM-labeled hydrolysis probe at the concentrations listed in Table 1, and nuclease-free water to final volume of 20 Five μL of TNA was used in each reaction.

TAC assay performance: Mastermix for each TAC consisted of the following: 1× AGPATH-ID™ One-step RT-PCR buffer and enzyme or 1× QSCRIPT™ XLT One-step RT-qPCR TOUGHMIX®. Reactions tested using AGPATH-ID™ enzyme system consisted of 50 μL 2× buffer, 4 μL 25× enzyme mix, and 46 μL of TNA. Reactions tested with the QSCRIPT™ enzyme system consisted of 50 μL 2× mastermix and 50 μL of TNA. Each card was centrifuged at 336×g for 1 min. twice, to distribute the fluid in the reaction wells, and sealed to sequester individual reactions. All TACs were run on the Applied Biosystems VIIA™ 7 Real-Time PCR system (Life Technologies, Foster City, CA) using the same cycling conditions as used for individual RT-qPCR reactions. A no template control (NTC) and a positive control consisting of combined RNA transcripts generated as previously described (Kodani and Winchell, *J. Clin. Microbiol.* 50:1057-1060, 2012) were included on each card.

Results

Analytical validation of new real-time PCR assays: For each new assay, no amplification was observed in no-template control (NTC) reactions (n≥95) or in reactions containing nucleic acid from other organisms (n≥200, data not shown). Each assay was also tested for inclusivity within the genus or species using representative isolates of each subspecies or serotype as appropriate (Table 2). The number of isolates used for inclusivity testing varied based on availability. The limit of detection was independently determined for each assay (Table 2).

TABLE 2

Analytical validation of newly developed real-time PCR assays for ANISA study

| Assay | Limit of Detection | No. of isolates tested | Notes |
|---|---|---|---|
| T. gondii | <1 fg | 1 | |
| S. aureus | 100 fg-10 fg/μL | 11 | Tested representative isolates from various MRSA clonal groups (USA 100, 200, 300, 400, 500, 800, 1000, Brazilian, EMRSA 15, and ST80) |
| K. pneumoniae | 100 fg/μL | 2 | |
| E. coli and Shigella spp. | 10 fg-1 fg/μL | 94 | Tested 21 Shigella isolates (4 different spp.) |
| P. aeruginosa | 100 fg-10 fg/μL | 7 | |
| Ureaplasma spp. | 1 pg/μL | 14 | Tested representative strain of all serotypes of U. urealyticum and U. parvum (1-14) |
| C. trachomatis | 15 copies/μL | 4 | Tested representative isolates of serovars D, E, H, and F |
| A. baumannii | 10 fg-1 fg/μL | 1 | |
| S. agalactiae (GBS) | 300 fg/μL | 30 | Tested representative isolates from all serotypes (1A, 1B, 2-7) and non-typeable isolates (n = 2) |

The target for real-time PCR detection of *E. coli* also reacts with the Shigellae. This *E. coli/Shigella* assay successfully detected all *E. coli* types tested, including representative isolates of each virotype (EHEC, EPEC, ETEC, EAEC, and EIEC), but did not amplify the closely related species *E. albertii*, *E. hermannii*, or *E. fergusonii*. This assay also detected all four *Shigella* species (*S. flexneri*, *S. sonnei*, *S. dysenteriae*, and *S. boydii*), with the exception of *S. dysenteriae* serotype I. During development and validation of this assay, sporadic amplification signal in NTC reactions was occasionally observed. This was determined to occur due to residual *E. coli* DNA present in the enzyme preparation from the manufacturers, which varied between production lots. Residual *E. coli* DNA in extraction reagents may also contribute to this phenomenon during testing of clinical specimens. Crossing threshold (Ct) values for this sporadic amplification were generally found to be >30. For this reason, a Ct cutoff value of 30 was implemented.

Figure 1C:
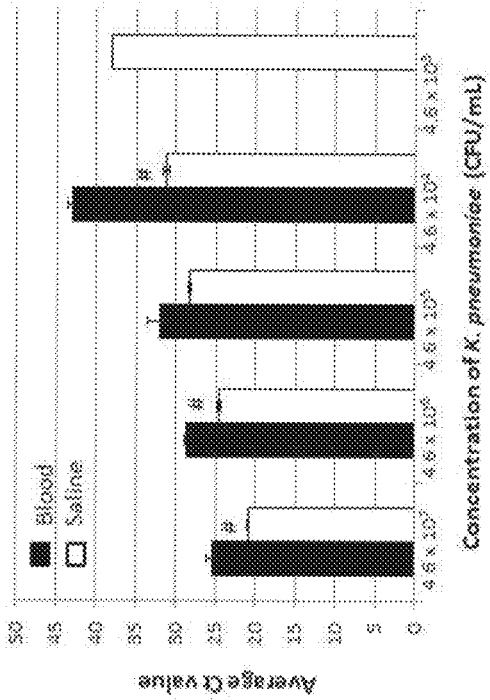
Figure 1B:
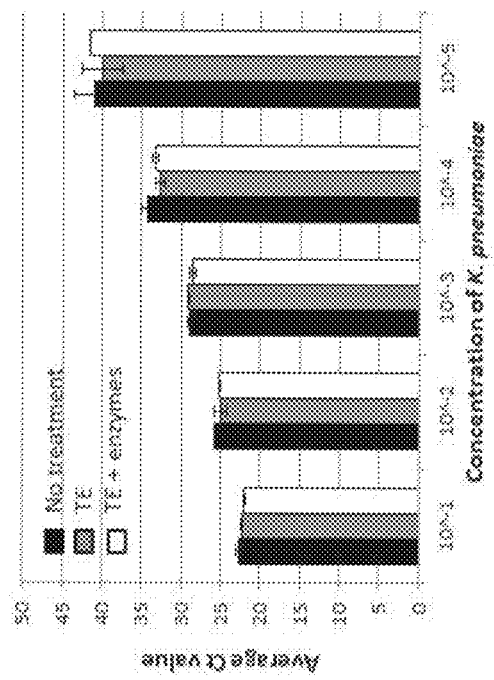

Extraction of TNA from blood and saline: Direct comparison of Ct values of TNA extracted from blood spiked with gram-positive bacteria (*S. aureus*) revealed that the average Ct value was approximately 5.5 cycles lower for TNA extracted after incubation with pre-lysis enzymes compared to identical preparations without this pre-treatment step (FIG. 1A). Incubation of spiked blood specimens with TE buffer alone did not result in lower Ct values, indicating that the observed improvement in Ct values was a result of the pre-lysis enzyme treatment instead of simply dilution and heating. Pre-treatment with lytic enzymes had no significant impact on Ct values of TNA from blood spiked with the gram-negative bacterium *K. pneumoniae* (FIG. 1B).

In addition, pre-lysis did not significantly impact target detection in saline spiked with the same serial dilutions. However, comparison of the Ct values for TNA extracted from blood and saline spiked with the same concentration of organisms revealed that detection in blood is significantly impaired relative to saline. The difference in Ct value for detection of the same number of bacteria in blood compared to saline ranged from 3.8 cycles at higher concentrations to 11.8 cycles at lower concentrations (mean difference in Ct value=6), including a complete lack of detection of the lowest concentration in blood (FIG. 1C).

TAC preparation: oligonucleotide concentration and assay replicates: The impact of oligonucleotide concentration on pathogen detection was briefly examined using the optimization TAC configuration. No significant difference in target amplification was observed at the limit of detection for any of the four targets examined. Additionally, testing of clinical specimens previously known to be positive for each of these pathogens did not reveal any oligonucleotide concentration-dependent difference in target detection.

Testing of serial dilutions of nucleic acid from *M. pneumoniae*, *S. pneumoniae*, *S. agalactiae*, and PIV2 revealed excellent concordance between replicates at higher TNA concentrations. In contrast, the number of replicate reactions in which amplification was observed decreased as the concentration approached the limit of detection for each assay. Testing five replicates allowed detection of less concentrated nucleic acid compared to two replicates. These results indicate that testing a higher number of replicates improves pathogen detection rates when the concentration of organisms is near the limit of detection.

Figures 2A, 2B:
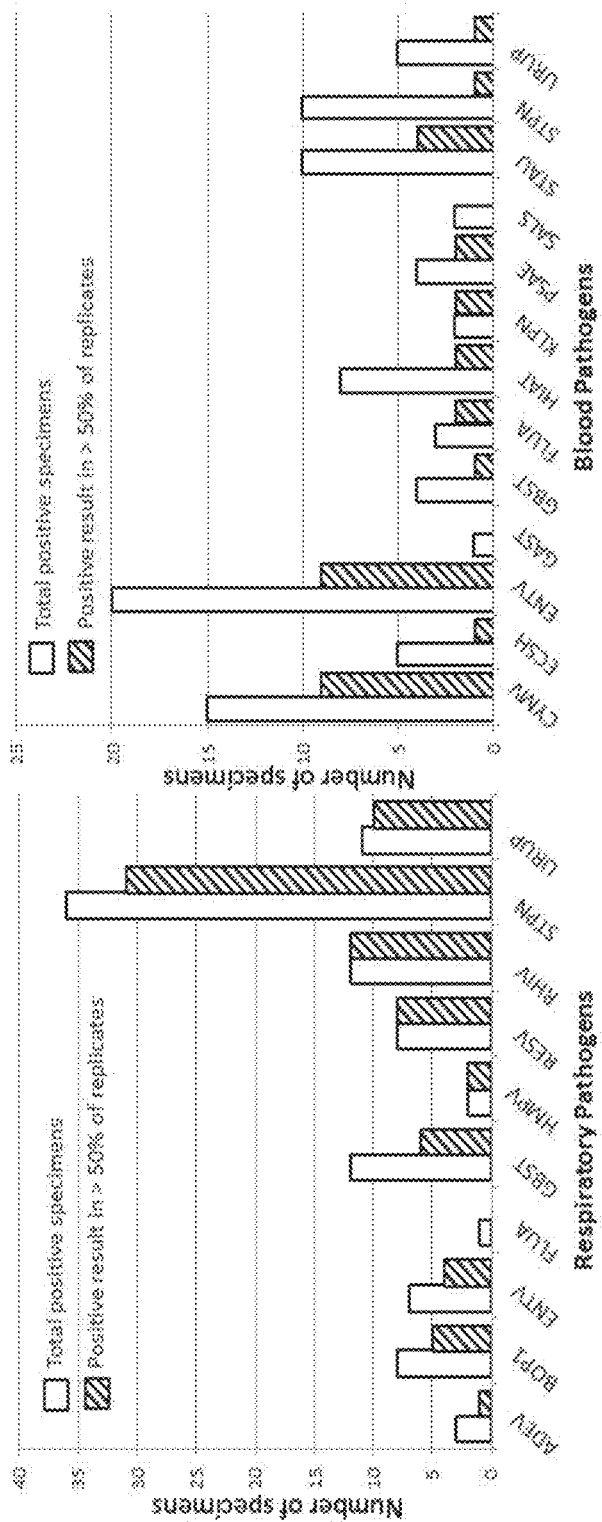
FIGS. 2A-2B are a pair of graphs showing concordance between replicates of primary clinical specimens tested on a TAQMAN® array card (TAC). Concordance between replicate results for nasopharyngeal/oropharyngeal (NP/OP) (FIG. 2A) and blood (FIG. 2B) specimens tested using TAC. Data shown are total number of specimens identified as positive in at least one replicate reaction (white bars) and proportion of positive specimens for which greater than 50% of replicates were positive (shaded bars). Number of replicates tested varied by target and specimen type; all targets were tested in ≥2 replicates. Total number of specimens tested, NP/OP (n=124), blood (n=661). ADEV, Adenovirus; BOP1, *Bordetella pertussis;* ENTV, Enterovirus; FLUA, Influenza A; GBST, Group B *Streptococcus;* HMPV, Human Metapneumovirus; RESV, Respiratory Syncytial Virus; RHIV, Rhinovirus; STPN, *Streptococcus pneumoniae;* URUP, *Ureaplasma* spp.; CYMV, Cytomegalovirus; ECSH, *Escherichia coli/Shigella* spp.; GAST, Group A *Streptococcus;* HIAT; *Haemophilus influenzae;* KLPN, *Klebsiella pneumoniae,* PSAE, *Pseudomonas aeruginosa,* SALS, *Salmonella* spp.; STAU, *Staphylococcus aureus.*

Positive results in clinical specimens were confirmed by repeat testing in individual RT-qPCR reactions followed by confirmation of the appropriate size amplicon. The proportion of NP/OP and blood specimens identified as positive in more than half of assay replicates varied by target (FIG. 2). Overall, this proportion was significantly higher in NP/OP specimens (FIG. 2A) compared to whole blood (FIG. 2B). In other words, while the majority of NP/OP specimens that were positive were identified as positive in more than half of assay replicates, amplification of pathogen-specific targets in whole blood extracts occurred in a much smaller proportion of total replicates tested. Furthermore, average Ct values were higher in positive reactions containing TNA extracted from blood compared to NP/OP swabs. Together these data suggest that a higher number of assay replicates may identify pathogens which otherwise would be missed, particularly in whole blood specimens.

Enzyme system performance with TAC: Newer generations of enzyme mixes may result in improved detection of pathogen targets, particularly in the presence of molecules known to have inhibitory effects on real-time PCR, such as some blood components. The performance of two enzyme formulations, Ambion AGPATH-ID™ One-step RT-PCR kit (Applied Biosystems) and Quanta QSCRIPT™ XLT One-step RT-qPCR TOUGHMIX®, low ROX (Quanta Biosciences), at detecting targets in NP/OP specimens (n=18) and blood specimens (n=12) (FIG. 3) were compared. The median difference in Ct value for positive results in NP/OP specimens tested with TOUGHMIX® compared to AGPATH-ID™ enzyme varied by target (range 0-4), but overall improved Ct values were observed in reactions using TOUGHMIX® enzyme (FIG. 3A). An even more dramatic improvement in Ct values was observed for blood specimens tested with TOUGHMIX® compared to AGPATH-ID™; the median difference in Ct value ranged from 0.46 to 10.5 for various targets (FIG. 3B). In addition, additional positive results (n=16) for pathogen-specific targets were detected using the TOUGHMIX® enzyme mix that were not detected when testing the same specimen extract using AGPATH-ID™. This phenomenon was not limited to a single pathogen target, but rather occurred with 12 unique assays. While a few instances (n=5) were also observed where the reactions using AGPATH-ID™ yielded a positive result while the TOUGHMIX® reaction was negative, this occurred only when the Ct value with AGPATH-ID™ was >33, at the threshold where reproducibility between replicates is most commonly discordant. Overall, improved pathogen detection was observed using the TOUGHMIX® enzyme system, particularly in primary blood specimens.

EXAMPLE 4

Diagnostic Multiplex PCR Assay

This example describes exemplary methods that can be used to detect one or more of *Acinetobacter baumannii*, *Pseudomonas aeruginosa*, *Klebsiella pneumoniae*, *Toxoplasma gondii*, *Moraxella catarrhalis*, *Escherichia coli/Shigella*, *Staphylococcus aureus*, *Pneumocystis jirovecii*, *Chlamydia trachomatis*, *Ureaplasma urealyticum*, *Ureaplasma parvum*, *Ureaplasma* spp., *Bartonella* spp., *Streptococcus agalactiae*, and/or *Neisseria meningitidis* nucleic acids in a sample from a subject, thereby diagnosing the subject with infection with the detected organism(s). The methods can also be used to detect presence of one or more of *Acinetobacter baumannii*, *Pseudomonas aeruginosa*, *Klebsiella pneumooniae*, *Toxoplasma gondii*, *Moraxella catarrhalis*, *Escherichia coli/Shigella*, *Staphylococcus aureus*, *Pneumocystis jirovecii*, *Chlamydia trachomatis*, *Ureaplasma urealyticum*, *Ureaplasma parvum*, *Ureaplasma* spp., *Bartonella* spp., *Streptococcus agalactiae*, and/or *Neisseria meningitidis* in an environmental sample. One of ordinary skill in the art will appreciate that methods that deviate from these specific methods can also be used to successfully detect *Acinetobacter baumannii*, *Pseudomonas aeruginosa*, *Klebsiella pneumoniae*, *Toxoplasma gondii*, *Moraxella catarrhalis*, *Escherichia coli/Shigella*, *Staphylococcus aureus*, *Pneumocystis jirovecii*, *Chlamydia trachomatis*, *Ureaplasma urealyticum*, *Ureaplasma parvum*, *Ureaplasma* spp., *Bartonella* spp., *Streptococcus agalactiae*, and/or *Neisseria meningitidis* nucleic acids in a sample.

Clinical samples are obtained from a subject (such as a subject suspected of having a CAP infection), such as a nasopharyngeal, oropharyngeal, or bronchial swab, bronchoalveolar lavage, or sputum, or an environmental sample is obtained, for example by swabbing a surface suspected of harboring one or more pathogens. DNA is extracted from the sample using routine methods (for example using a commercial kit).

Multiplex real-time PCR is performed in a reaction including a reaction mix (e.g., buffers, $MgCl_2$, dNTPs, and DNA polymerase), sample DNA (5 µl of nucleic acid extracted from the sample), and probes and primers (such as those in Table 1, above). The probes and primers are included in the reaction at concentrations of about 25 nM to 1 µM. The assay is performed using a real-time PCR system (such as the ABI 7500). Exemplary thermocycling conditions are 5 minutes at 95° C., followed by 45 cycles of 95° C. for 15 seconds and 60° C. for 1 minute. Positive samples are those with a positive $C_t$ value for one or more pathogen probes.

EXAMPLE 5

Diagnostic Microfluidic Card Assay

This example describes exemplary methods that can be used to simultaneously detect one or more of *Acinetobacter baumannii*, *Pseudomonas aeruginosa*, *Klebsiella pneumooniae*, *Toxoplasma gondii*, *Moraxella catarrhalis*, *Escherichia coli/Shigella*, *Staphylococcus aureus*, *Pneumocystis jirovecii*, *Chlamydia trachomatis*, *Ureaplasma urealyticum*, *Ureaplasma parvum*, *Ureaplasma* spp., *Bartonella* spp., *Streptococcus agalactiae*, and/or *Neisseria meningitidis* nucleic acids in a sample from a subject, thereby diagnosing the subject with infection with the detected organism(s), or presence of the detected organism(s) in an environmental sample. One of ordinary skill in the art will appreciate that methods that deviate from these specific methods can also be used to successfully detect one or more of *Acinetobacter baumannii*, *Pseudomonas aeruginosa*, *Klebsiella pneumooniae*, *Toxoplasma gondii*, *Moraxella catarrhalis*, *Escherichia coli/Shigella*, *Staphylococcus* aureus, *Pneumocystis jirovecii, Chlamydia trachomatis, Ureaplasma urealyticum, Ureaplasma parvum, Ureaplasma* spp., *Bartonella* spp., *Streptococcus agalactiae,* and/or *Neisseria meningitidis* nucleic acids in a sample.

Clinical samples are obtained from a subject (such as a subject suspected of having a pathogenic infection), such as a nasopharyngeal, oropharyngeal, or bronchial swab, bronchoalveolar lavage, or sputum, or an environmental sample is obtained, for example by swabbing a surface suspected of harboring one or more pathogens. Nucleic acids (such as DNA, RNA, or total nucleic acid) are extracted from the sample using routine methods (for example using a commercial kit).

A microfluidic card (such as a TAQMAN® Array card (also known as a TAQMAN® Low Density Array card); Applied Biosystems, Foster City, CA) including primers and probes for one or more of *Acinetobacter baumannii, Pseudomonas aeruginosa, Klebsiella pneumooniae, Toxoplasma gondii, Moraxella catarrhalis, Escherichia coli/ Shigella, Staphylococcus aureus, Pneumocystis jirovecii, Chlamydia trachomatis, Ureaplasma urealyticum, Ureaplasma parvum, Ureaplasma* spp., *Bartonella* spp., *Streptococcus agalactiae,* and/or *Neisseria meningitidis* is utilized. Individual wells of the card include primers and probe for a single pathogen, which are preloaded and dried onto the designated wells (for example in duplicate). The card may include at least one well containing *Acinetobacter baumannii* primers and probe (SEQ ID NOs: 12-14), at least one well containing *Pseudomonas aeruginosa* primers and probe (SEQ ID NOs: 15-17), at least one well containing *Klebsiella pneumoniae* primers and probe (SEQ ID NOs: 18-20 and/or SEQ ID NOs: 58-60), at least one well containing *Toxoplasma gondii* primers and probe (SEQ ID NOs: 21-23), at least one well containing *Moraxella catarrhalis* primers and probe (SEQ ID NOs: 24-26), at least one well containing *E. coli/Shigella* primers and probe (SEQ ID NOs: 27-29), at least one well containing *Staphylococcus aureus* primers and probe (SEQ ID NOs: 30-32), at least one well containing *Pneumocystis jirovecii* primers and probe (SEQ ID NOs: 33-35), at least one well containing *Chlamydia trachomatis* primers and probe (SEQ ID NOs: 36-38), at least one well containing *Ureaplasma urealyticum* primers and probe (SEQ ID NOs: 39-41), at least one well containing *Ureaplasma parvum* primers and probe (SEQ ID NOs: 42-44), at least one well containing *Ureaplasma* spp. primers and probe (SEQ ID NOs: 45-47), at least one well containing *Bartonella* spp. primers and probe (SEQ ID NOs: 48-50 or SEQ ID NOs: 49-51), at least one well containing *Streptococcus agalactiae* primers and probe (SEQ ID NOs: 54-56), or at least one well containing *Neisseria meningitidis* primers and probe (SEQ ID NOs: 62-64). Each probe includes a 5' FAM fluorophore. Unless otherwise noted, each probe also includes a 3' BHQ1 quencher. The *P. jirovecii* probe (SEQ ID NO: 35), the *U. parvum* probe (SEQ ID NO: 44), and the *Ureaplasma* spp. probe (SEQ ID NO: 47) each also include an internal BHQ1 quencher. One of ordinary skill in the art can select different labels and quenchers with only routine testing.

A master mix, including 1× RT-PCR buffer, 1×RT-PCR enzyme and nucleic acids isolated from a sample is applied to the microfluidic card utilizing the loading ports. The cards are centrifuged, sealed, and placed in a thermocycler (such as the Applied Biosystems VIIA™ 7 real-time PCR platform). Cycling conditions are 45° C. for 10 minutes, 94° for 10 minutes, and 45 cycles of 94° C. for 30 seconds and 60° C. for 1 minute (although these conditions can be adjusted by one of ordinary skill in the art to obtain optimal results, for example 55° C., instead of 60° C., in some examples). Positive samples are those with a positive $C_t$ value for one or more probes.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method for detecting presence of *Klebsiella pneumoniae* in a sample, comprising:
   contacting the sample with a nucleic acid probe comprising the nucleic acid sequence of SEQ ID NO: 60, or the reverse complement thereof, and a donor fluorophore, an acceptor fluorophore, or a combination thereof;
   amplifying a nucleic acid from *Klebsiella pneumoniae*, wherein the amplifying comprises contacting the sample with a pair of primers comprising the nucleic acid sequences of SEQ ID NOs: 58 and 59; and
   detecting hybridization between the nucleic acid probe and a nucleic acid in the sample, wherein detection of hybridization indicates the presence of *Klebsiella pneumoniae* in the sample.

2. The method of claim 1, further comprising detecting *Ureaplasma* spp., in the sample by:
   (a) contacting the sample with
   a probe comprising or consisting of the nucleic acid sequence set forth as SEQ ID NO: 47; and
   (b) detecting hybridization between the probe and a nucleic acid in the sample, wherein detection of hybridization in the sample indicates the presence of *Ureaplasma* spp. in the sample.

3. The method of claim 2, further comprising amplifying a nucleic acid from *Ureaplasma* spp. by contacting the nucleic acid with at least one primer, wherein the at least one primer comprises the nucleic acid sequence set forth in SEQ ID NO: 45 or SEQ ID NO: 46.

4. The method of claim 1, wherein the sample comprises a biological sample or environmental sample.

5. The method of claim 4, wherein the sample is a biological sample comprising tissue, blood, serum, cerebral spinal fluid, middle ear fluid, bronchoalveolar lavage, tracheal aspirate, sputum, nasopharyngeal aspirate, oropharyngeal aspirate, or saliva or the sample is an environmental sample comprising a food sample, a water sample, or a surface swab.

6. An isolated nucleic acid probe consisting of the nucleic acid sequence of SEQ ID NO: 60 and a donor fluorophore, an acceptor fluorophore, or a combination thereof.

7. A kit for detection of *Klebsiella pneumoniae*, comprising the isolated nucleic acid probe of claim 6 and a pair of primers comprising the nucleic acid sequences of SEQ ID NOs: 58 and 59.

8. The kit of claim 7, further comprising one or more primers comprising or consisting of the nucleic acid sequence of any one of SEQ ID NOs: 45 and 46.

9. The kit of claim 7, further comprising an isolated nucleic acid probe comprising the nucleic acid sequence of SEQ ID NO: 47, and a donor fluorophore, an acceptor fluorophore, or a combination thereof.

10. The method of claim 1, further comprising detecting *Acinetobacter baumannii* in the sample by:
(a) contacting the sample with a nucleic acid probe comprising or consisting of the nucleic acid sequence of SEQ ID NO: 14; and
(b) detecting hybridization between the probe and a nucleic acid in the sample, wherein detection of hybridization in the sample indicates the presence of *Acinetobacter baumannii* in the sample.

11. The method of claim 1, further comprising detecting *Pseudomonas aeruginosa* in the sample by:
(a) contacting the sample with a nucleic acid probe comprising or consisting of the nucleic acid sequence of SEQ ID NO: 17; and
(b) detecting hybridization between the probe and a nucleic acid in the sample, wherein detection of hybridization in the sample indicates the presence of *Pseudomonas aeruginosa* in the sample.

12. The method of claim 1, further comprising detecting *Staphylococcus aureus* in the sample by:
(a) contacting the sample with a nucleic acid probe comprising or consisting of the nucleic acid sequence of SEQ ID NO: 32; and
(b) detecting hybridization between the probe and a nucleic acid in the sample, wherein detection of hybridization in the sample indicates the presence of *Staphylococcus aureus* in the sample.

13. The method of claim 1, further comprising detecting *Toxoplasma gondii* in the sample by:
(a) contacting the sample with a nucleic acid probe comprising or consisting of the nucleic acid sequence of SEQ ID NO: 23; and
(b) detecting hybridization between the probe and a nucleic acid in the sample, wherein detection of hybridization in the sample indicates the presence of *Toxoplasma gondii* in the sample.

14. The method of claim 1, further comprising detecting *Moraxella catarrhalis* in the sample by:
(a) contacting the sample with a nucleic acid probe comprising or consisting of the nucleic acid sequence of SEQ ID NO: 26; and
(b) detecting hybridization between the probe and a nucleic acid in the sample, wherein detection of hybridization in the sample indicates the presence of *Moraxella catarrhalis* in the sample.

15. The method of claim 1, further comprising detecting *Escherichia coli* and/or *Shigella* in the sample by:
(a) contacting the sample with a nucleic acid probe comprising or consisting of the nucleic acid sequence of SEQ ID NO: 29; and
(b) detecting hybridization between the probe and a nucleic acid in the sample, wherein detection of hybridization in the sample indicates the presence of *Escherichia coli* and/or *Shigella* in the sample.

16. The method of claim 1, further comprising detecting *Chlamydia trachomatis* in the sample by:
(a) contacting the sample with a nucleic acid probe comprising or consisting of the nucleic acid sequence of SEQ ID NO: 38; and
(b) detecting hybridization between the probe and a nucleic acid in the sample, wherein detection of hybridization in the sample indicates the presence of *Chlamydia trachomatis* in the sample.

17. The method of claim 1, further comprising detecting *Ureaplasma urealyticum* in the sample by:
(a) contacting the sample with a nucleic acid probe comprising or consisting of the nucleic acid sequence of SEQ ID NO: 41; and
(b) detecting hybridization between the probe and a nucleic acid in the sample, wherein detection of hybridization in the sample indicates the presence of *Ureaplasma urealyticum* in the sample.

18. The method of claim 1, further comprising detecting *Ureaplasma parvum* in the sample by:
(a) contacting the sample with a nucleic acid probe comprising or consisting of the nucleic acid sequence of SEQ ID NO: 44; and
(b) detecting hybridization between the probe and a nucleic acid in the sample, wherein detection of hybridization in the sample indicates the presence of *Ureaplasma parvum* in the sample.

19. The method of claim 1, further comprising detecting *Streptococcus agalactiae* in the sample by:
(a) contacting the sample with a nucleic acid probe comprising or consisting of the nucleic acid sequence of SEQ ID NO: 56; and
(b) detecting hybridization between the probe and a nucleic acid in the sample, wherein detection of hybridization in the sample indicates the presence of *Streptococcus agalactiae* in the sample.

20. The method of claim 1, further comprising detecting *Bartonella* spp. in the sample by:
(a) contacting the sample with a nucleic acid probe comprising or consisting of the nucleic acid sequence of SEQ ID NO: 50; and
(b) detecting hybridization between the probe and a nucleic acid in the sample, wherein detection of hybridization in the sample indicates the presence of *Bartonella* spp. in the sample.

21. A method for detecting presence of *Klebsiella pneumoniae* in a sample, comprising:
contacting the sample with a nucleic acid probe comprising the nucleic acid sequence of SEQ ID NO: 20, or the reverse complement thereof, and a donor fluorophore, an acceptor fluorophore, or a combination thereof;
amplifying a nucleic acid from *Klebsiella pneumoniae*, wherein the amplifying comprises contacting the sample with a pair of primers comprising the nucleic acid sequences of SEQ ID NOs: 18 and 19; and
detecting hybridization between the nucleic acid probe and a nucleic acid in the sample, wherein detection of hybridization indicates the presence of *Klebsiella pneumoniae* in the sample.

22. An isolated nucleic acid probe consisting of the nucleic acid sequence of SEQ ID NO: 20 and a donor fluorophore, an acceptor fluorophore, or a combination thereof.

23. A kit for detection of Klebsiella pneumoniae, comprising the isolated nucleic acid probe of claim 22 and a pair of primers comprising the nucleic acid sequences of SEQ ID NOs: 18 and 19.

* * * * *